(12) United States Patent
Kong et al.

(10) Patent No.: US 7,262,223 B2
(45) Date of Patent: Aug. 28, 2007

(54) AMIDINE DERIVATIVES FOR TREATING AMYLOIDOSIS

(75) Inventors: Xianqi Kong, Dollard-des-Ormeaux (CA); Xinfu Wu, Laval (CA); David Migneault, Laval (CA)

(73) Assignee: Neurochem (International) Limited, Lausanne (CH)

( * ) Notice: Subject to any disclaimer, the term of this patent is extended or adjusted under 35 U.S.C. 154(b) by 0 days.

(21) Appl. No.: 10/763,953

(22) Filed: Jan. 23, 2004

(65) Prior Publication Data

US 2005/0182118 A1 Aug. 18, 2005

(51) Int. Cl.
A61K 31/155 (2006.01)
A61K 31/4164 (2006.01)
A61K 31/166 (2006.01)
A61K 31/18 (2006.01)
A61K 31/4168 (2006.01)

(52) U.S. Cl. ............... 514/637; 514/617; 514/633; 514/539; 514/636; 514/401; 514/616; 514/392; 514/603; 548/379.4; 548/371.4; 560/35; 564/246; 564/182; 564/229; 564/243; 564/153; 564/152; 564/82

(58) Field of Classification Search .......... 548/379.4, 548/371.4; 560/35; 564/246, 182, 229, 564/243, 153, 152, 82; 514/637, 617, 633, 514/539, 636, 401, 616, 392, 603
See application file for complete search history.

(56) References Cited

U.S. PATENT DOCUMENTS

| | | |
|---|---|---|
| 4,324,794 A | 4/1982 | Tidwell et al. |
| 4,397,863 A | 8/1983 | Tidwell et al. |
| 4,515,625 A | 5/1985 | Burow, Jr. |
| 4,522,811 A | 6/1985 | Eppstein et al. |
| 4,619,942 A | 10/1986 | Tidwell et al. |
| 4,933,347 A | 6/1990 | Tidwell et al. |
| 4,940,723 A | 7/1990 | Tidwell et al. |
| 4,963,589 A | 10/1990 | Tidwell et al. |
| 5,202,320 A | 4/1993 | Tidwell et al. |
| 5,206,236 A | 4/1993 | Tidwell et al. |
| 5,246,965 A | 9/1993 | Main |
| 5,374,548 A | 12/1994 | Caras |
| 5,387,742 A | 2/1995 | Cordell |
| 5,399,311 A | 3/1995 | Kasai et al. |
| 5,428,051 A | 6/1995 | Tidwell et al. |
| 5,441,870 A | 8/1995 | Seubert et al. |
| 5,451,700 A | 9/1995 | Morrissey et al. |
| 5,521,189 A | 5/1996 | Boykin et al. |
| 5,538,845 A | 7/1996 | Knops et al. |
| 5,547,841 A | 8/1996 | Marotta et al. |
| 5,552,426 A | 9/1996 | Lunn et al. |
| 5,574,059 A | 11/1996 | Regunathan et al. |
| 5,578,631 A | 11/1996 | Tidwell et al. |
| 5,594,138 A | 1/1997 | Dykstra et al. |
| 5,602,172 A | 2/1997 | Boykin et al. |
| 5,605,811 A | 2/1997 | Seubert et al. |
| 5,606,058 A | 2/1997 | Boykin et al. |
| 5,612,363 A | 3/1997 | Mohan et al. |
| 5,622,955 A | 4/1997 | Boykin et al. |
| 5,627,184 A | 5/1997 | Boykin et al. |
| 5,639,755 A | 6/1997 | Dykstra et al. |
| 5,643,562 A | 7/1997 | Kisilevsky et al. |
| 5,643,935 A | 7/1997 | Dykstra et al. |
| 5,667,975 A | 9/1997 | Dykstra et al. |
| 5,668,166 A | 9/1997 | Tidwell et al. |
| 5,668,167 A | 9/1997 | Tidwell et al. |
| 5,686,456 A | 11/1997 | Boykin et al. |
| 5,686,477 A | 11/1997 | Jarry et al. |
| 5,686,496 A | 11/1997 | Anderskewitz et al. |
| 5,720,936 A | 2/1998 | Wadsworth et al. |
| 5,721,106 A | 2/1998 | Maggio et al. |
| 5,723,288 A | 3/1998 | Dykstra et al. |
| 5,723,495 A | 3/1998 | Hall et al. |
| 5,726,197 A | 3/1998 | Clark et al. |
| 5,728,375 A | 3/1998 | Kisilevsky et al. |
| 5,731,332 A | 3/1998 | Anderskewitz et al. |
| 5,792,782 A | 8/1998 | Dykstra et al. |
| 5,811,633 A | 9/1998 | Wadsworth et al. |
| 5,817,686 A | 10/1998 | Dykstra et al. |
| 5,817,687 A | 10/1998 | Dykstra et al. |
| 5,840,294 A | 11/1998 | Kisilevsky et al. |

(Continued)

FOREIGN PATENT DOCUMENTS

EP 0518818 A2 12/1992

(Continued)

OTHER PUBLICATIONS

Citron, M. Nature Reviews Neuroscience 2004, 5, 677-685.*

(Continued)

*Primary Examiner*—Kamal A. Saeed
*Assistant Examiner*—Jason M. Nolan
(74) *Attorney, Agent, or Firm*—Lahive & Cockfield, LLP

(57) ABSTRACT

The present invention relates to the use of amidine compounds in the treatment of amyloid-related diseases. In particular, the invention relates to a method of treating or preventing an amyloid-related disease in a subject comprising administering to the subject a therapeutic amount of an amidine compound. Among the compounds for use according to the invention are those according to the following Formula, such that, when administered, amyloid fibril formation, neurodegeneration, or cellular toxicity is reduced or inhibited:

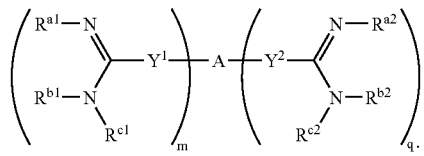

7 Claims, No Drawings

U.S. PATENT DOCUMENTS

| | | | |
|---|---|---|---|
| 5,843,980 | A | 12/1998 | Hall et al. |
| 5,871,924 | A | 2/1999 | Yarus et al. |
| 5,935,982 | A | 8/1999 | Dykstra et al. |
| 5,939,440 | A | 8/1999 | Dykstra et al. |
| 5,972,328 | A | 10/1999 | Kisilevsky et al. |
| 5,972,969 | A | 10/1999 | Dykstra et al. |
| 6,008,247 | A | 12/1999 | Boykin et al. |
| 6,017,941 | A | 1/2000 | Dykstra et al. |
| 6,025,398 | A | 2/2000 | Hall et al. |
| 6,037,377 | A | 3/2000 | Anderskewitz et al. |
| 6,046,226 | A | 4/2000 | Dykstra et al. |
| 6,127,423 | A | 10/2000 | Anderskewitz et al. |
| 6,127,554 | A | 10/2000 | Boykin et al. |
| 6,133,281 | A | 10/2000 | Gonzalez-Cadavid et al. |
| 6,156,779 | A | 12/2000 | Dykstra et al. |
| 6,172,104 | B1 | 1/2001 | Tidwell et al. |
| 6,197,824 | B1 | 3/2001 | Schromm et al. |
| 6,214,883 | B1 | 4/2001 | Hall et al. |
| 6,294,565 | B1 | 9/2001 | Dykstra et al. |
| 6,319,944 | B1 | 11/2001 | Claiborne et al. |
| 6,326,395 | B1 | 12/2001 | Tidwell et al. |
| 6,489,365 | B1 | 12/2002 | Anderskewitz et al. |
| 6,625,612 | B1 | 9/2003 | Tal et al. |
| 6,627,647 | B1 | 9/2003 | Betageri |
| 6,635,668 | B1 | 10/2003 | Tidwell et al. |
| 2001/0044468 | A1 | 11/2001 | Hall et al. |
| 2003/0083362 | A1 | 5/2003 | Boykin et al. |
| 2003/0130303 | A1 | 7/2003 | Coe et al. |
| 2003/0199521 | A1 | 10/2003 | Dykstra et al. |

FOREIGN PATENT DOCUMENTS

| | | |
|---|---|---|
| EP | 0601977 A1 | 6/1994 |
| EP | 0941991 B1 | 9/1999 |
| JP | 7-279092 | 10/1995 |
| WO | WO-93/16036 A1 | 8/1993 |
| WO | WO-94/11341 A1 | 5/1994 |
| WO | WO-95/19772 A1 | 7/1995 |
| WO | WO-96/15126 A1 | 5/1996 |
| WO | WO-96/28187 A1 | 9/1996 |
| WO | WO-98/13037 A1 | 4/1998 |
| WO | WO-98/40381 A1 | 9/1998 |
| WO | WO-98/55454 A2 | 12/1998 |
| WO | WO-00/04893 A2 | 2/2000 |
| WO | WO-01/03680 | 1/2001 |
| WO | WO-01/03685 A2 | 1/2001 |
| WO | WO-01/32159 A2 | 5/2001 |
| WO | WO-01/46175 A1 | 6/2001 |
| WO | WO-01/85093 A2 | 11/2001 |
| WO | WO-02/02516 A2 | 1/2002 |
| WO | WO-02/34715 A1 | 5/2002 |
| WO | WO-02/36588 A2 | 5/2002 |
| WO | WO-02/055025 A2 | 7/2002 |
| WO | WO-02/058684 A2 | 8/2002 |
| WO | WO-02/058697 A1 | 8/2002 |
| WO | WO-02/062785 A1 | 8/2002 |
| WO | WO-03/017994 A1 | 3/2003 |
| WO | WO 03017994 A1 * | 3/2003 |
| WO | WO-03/103598 A2 | 12/2003 |
| WO | WO 03103598 A2 * | 12/2003 |
| WO | WO-2005/033065 A1 | 4/2005 |
| WO | WO 2005033065 A1 * | 4/2005 |
| WO | WO-2005/079780 A1 | 9/2005 |

OTHER PUBLICATIONS

Tanzi, R.E. Nature Medicine 1996, 2(1), 31-32.*

Masters et al. Proc. Natl. Acad. Sci. USA 1985, 82, 4245-4249.*

Askanas V, et al., "New advances in the understanding of sporadic inclusion-body myositis and hereditary inclusion-body myopathies." Curr. Opin. Rheumatol. 7(6), 486-96 (Nov. 1995).

Askanas V, et al., "Transfer of beta-amyloid precursor protein gene using adenovirus vector causes mitochondrial abnormalities in cultured normal human muscle." Proc. Nat'l Acad. Sci. U.S.A. 93(3), 1314-19 (Feb. 1996).

Bailly, C, et al., "Sequence-selective binding to DNA of bis(amidinophenoxy)alkanes related to propamidine and pentamidine," Biochem J. Apr. 1, 1997;323 ( Pt 1):23-31.

Baldwin, et al., "Molecular Biology, Genetics and Protein Chemistry of Prion Diseases," Research Advances in Alzheimer's Disease and Related Disorders, John Wiley and Sons, New York, 757-773 (1995).

Bayer, TA, et al., "Key factors in Alzheimer's disease: β amyloid precursor protein processing, metabolism and intraneuronal transport," Brain Pathology 11, 111 (2001).

Beekes, M, et al., "Western blot mapping of disease-specific amyloid in various animal species and humans with transmissible spongiform encephalopathies using a high-yield purification method." J. Gen. Virol. 76(Pt 10), 2567-76 (Oct. 1995).

Benson, DA, et al., "GenBank," Nucl. Acids Res. 28(1):15-18 (2000).

Berge, et al., "Pharmaceutical salts." J. Pharm. Sci. 66(1), 1-19 (Jan. 1977).

Bilik P., et al., "Novel dications with unfused aromatic systems: trithiophene and trifuran derivatives of furimidazoline," CHEMBIOCHEM 2(78), 559-69 (2001).

Boado, R.J., et al., "Drug delivery of antisense molecules to the brain for treatment of Alzheimer's disease and cerebral AIDS," J. Pharm. Sci. 87(11), 1308-15 (Nov. 1998).

Bohmann, B., et al., "Self-assembly of β-amyloid 42 is retarded by small molecular ligands at the stage of structural intermediates," J. Struct. Biol. 130(2-3), 232-46 (Jun. 2000).

Boykin, D. W et al., "Anti-Pneumocystis carinii pneumonia activity of dicationic diaryl methylpyrimidines" European Journal of Medicinal Chemistry (1997), 32(12), 965-972.

Cardin, A.D, et al., "Molecular modeling of protein-glycosaminoglycan interactions," Arteriosclerosis. 9(1), 21-32 (Jan.-Feb. 1989).

Caughey, GH, et al., "Bis(5-amidino-2-benzimidazolyl)methane and related amidines are potent, reversible inhibitors of mast cell tryptases," J Pharmacol Exp Ther. Feb. 1993;264(2):676-82.

Chauhan, P.M.S. et al., "Antiparasitic Agents: Part VI—Synthesis of 1,2-,1-3- & 1,4-Bis(4-substituted aryloxy)benzenes & Their Biological Activities," *Indian Journal of Chemistry*, vol. 27B:38-42 (1988).

Chauhan, PM, et al., "Effect of new diamidines against *Leishmania donovani* infection," Indian J Exp Biol. Feb. 1993;31(2):196-8.

Chongprasert, S., et al., "Effects of freeze-dry processing conditions on the crystallization of pentamidine isethionate," J. Pharm. Sci. 87(9), 1155-60 (Sep. 1998).

Contreras, J.M., et al., "Aminopyridazines as acetylcholinesterase inhibitors." J. Med. Chem. 42(4), 730-41 (Feb. 1999).

Czamy A, et al., "Analysis of van der Waals and Electrostatic Contributions in the Interactions of Minor Groove Binding Benzimidazoles with DNA," J. Am. Chem. Soc.; 1995; 117(16); 4716-4717.

De Clercq, E., "Diaryl Amidine Derivatives as Oncornaviral DNA Polymerase Inhibitors," *J. Med. Chem.*, vol. 23:787-795 (1980).

de Koning, EJ, et al., "Diabetes mellitus in Macaca mulatta monkeys is characterised by islet amyloidosis and reduction in beta-cell population." Diabetologia 36(5), 378-84 (May 1993).

Donkor, IO, et al., "Pentamidine congeners: 2,2-butenebridged aromatic diamidines and diimidazolines as potential anti-Pneumocystis carinii pneumonia agents," J. Med. Chem. 37(26), 4554-57 (1994).

Dubovi, EJ, et al., "Inhibition of respiratory syncytial virus-host cell interactions by mono- and diamidines. Antimicrob Agents Chemother," Apr. 1981;19(4):649-56.

Dunbar PG, et al., "Design, synthesis, and neurochemical evaluation of 2-amino-5-(alkoxycarbonyl)-3,4,5,6-tetrahydropyridines and 2-amino-5-(alkoxycarbonyl)-1,4,5,6-tetrahydropyrimidines as M1 muscarinic receptor agonists," J Med Chem. Aug. 19, 1994;37(17):2774-82.

Fairley, TA, et al., "Structure, DNA minor groove binding, and base pair specificity of alkyl- and aryl-linked bis(amidinobenzimidazoles) and bis(amidinoindoles)," J Med Chem. Jun. 11, 1993;36(12):1746-53.

Frangione, B, et al., "Familial cerebral amyloid angiopathy related to stroke and dementia." Amyloid. 8(Suppl 1), 36-42, Review (Jul. 2001).

Garcia-Sevilla J, et al., "I2-imidazoline receptors in the healthy and pathologic human brain," Ann N Y Acad Sci. Jul. 12, 1995;763:178-93.

Garcia-Sevilla JA, "Imidazoline receptor proteins in brains of patients with Alzheimer's disease." Neurosci. Lett. 247(2-3), 95-98 (May 1998).

Geratz, JD, et al., "Amidino-substituted aromatic heterocycles as probes of the specificity pocket of trypsin-like proteases," Arch Biochem Biophys. Oct. 15, 1979;197(2):551-9.

Geratz, JD, et al., "Inhibitory effect of amidino-substituted heterocyclic compounds on the amidase activity of plasmin and of high and low molecular weight urokinase and on urokinase-induced plasminogen activation," Thromb Res. Oct. 1-15, 1981;24(1-2):73-83.

Geratz, JD, et al., "Novel bis(benzamidino) compounds with an aromatic central link. Inhibitors of thrombin, pancreatic kallikrein, trypsin, and complement," J Med Chem. May 1976; 19(5):634-9.

Gervais, F, "Amyloid—Those Deadly Fibrils." Eur. Biopham. Review, 40-42 (Autumn 2001).

Giamarellou, H, et al., 'Methicillin resistant' *Staphylococcus aureus* infections during 1978-79: clinical and bacteriologic observations, J. Antimicrob. Chemother. 1981 7: 649-655.

Glenner, GG, et al., "Alzheimer's disease and Down's syndrome: sharing of a unique cerebrovascular amyloid fibril protein." Biochem. Biophys. Res. Commun. 122(3), 1131-35 (Aug. 1984).

Glenner, GG, et al., "Alzheimer's disease: initial report of the purification and characterization of a novel cerebrovascular amyloid protein." Biochem. Biophys. Res. Commun. 120(3), 885-90 (May 1984).

Golde, TE, "Alzheimer disease therapy: Can the amyloid cascade be halted?" J. Clin. Invest. 111, 11-18 (2003).

Gouras, GK, "Current theories for the molecular and cellular pathogenesis of Alzheimer's disease," Exp. Rev. Mol. Med. (May 31, 2001), http://www-emm.cbcu.cam.ac.uk/01003167h.htm.

Hall, JE, et al., "Anti-Pneumocystis activities of aromatic diamidoxime prodrugs," Antimicrob Agents Chemother. Mar. 1998;42(3):666-74.

Hardy J, Selkoe DJ., "The amyloid hypothesis of Alzheimer's disease: progress and problems on the road to therapeutics." Science 297(5580), 353-56 (Jul. 2002).

Huang, T.L., et al., "Synthesis and anti-Pneumocystis carinii activity of piperidine-linked aromatic diimidazolines," Bioorg. Med. Chem. Lett. 6(17), 2087-90 (1996).

Jones SK, et al., "Novel pentamidine analogs in the treatment of experimental Pneumocystis carinii pneumonia." Antimicrob. Agents Chemother. 34(6), 1026-30 (Jun. 1990).

Lambert MP, et al., "Diffusible, nonfibrillar ligands derived from Abeta1-42 are potent central nervous system neurotoxins." Proc. Nat'l Acad. Sci. U.S.A. 95(11), 6448-53 (May 1998).

Lansiaux, A et al., "Distribution of furamidine analogues in tumor cells: influence of the number of positive charges," J Med Chem. May 9, 2002;45(10):1994-2002.

Lorenzo A, et al., "Pancreatic islet cell toxicity of amylin associated with type-2 diabetes mellitus," Nature 368(6473), 756-60 (Apr. 1994).

Mayeux, R, et al., "Drug Therapy. Treatment of Alzheimer's Disease," New Engl. J. Med. 341(22), 1670-79 (1999).

Messer WS Jr, et al., "Synthesis and biological characterization of 1,4,5,6-tetrahydropyrimidine and 2-amino-3,4,5,6-tetrahydropyridine derivatives as selective m1 agonists," J Med Chem. Apr. 11, 1997;40(8):1230-46.

Nandi G., et al., "Synthesis, spectroscopic properties and antileishmanial screening of some pentamidine analogs," J. Indian Chem. Soc. 70(6), 527-31 (1993).

Opie EL, "On the relation of chronic interstitial pancreatitis to the islands of Langerhans and to diabetes mellitus." J. Exp. Med. 5, 397-428 (Jan. 1900).

Parrish RF,et al., "Structure-activity relationships for the inhibition of acrosin by benzamidine derivatives," J Med Chem. Nov. 1978;21(11):1132-6.

Ren, J, et al., "Molecular recognition of a RNA:DNA hybrid structure," J Am Chem Soc. Jul. 11, 2001;123(27):6742-3.

Reynolds IJ, et al., "Pentamidine is an N-methyl-D-aspartate receptor antagonist and is neuroprotective in vitro," J Neurosci. Mar. 1992;12(3):970-5.

Reynolds IJ, et al., "Studies on the effects of several pentamidine analogues on the NMDA receptor," Eur J Pharmacol. Jan. 15, 1993;244(2):175-9.

Rupniak, N.M., et al., "Reversal of cognitive impairment by heptyl physostigmine, a long-lasting cholinesterase inhibitor, in primates." J. Neurol. Sci. 107(2), 246-49 (Feb. 1992).

Selkoe, DJ, "Alzheimer's Disease: Genes, Proteins, and Therapy," Physiol. Rev. 81(2), 741-66 (Apr. 2001).

Silverman, RB, "The Organic Chemistry of Drug Design and Drug Action," Academic Press, Chapter 8 (1992).

Soto J, et al., "Dissociation between I2-imidazoline receptors and MAO-B activity in platelets of patients with Alzheimer's type dementia." J. Psychiatr. Res. 33(3), 251-27 (May-Jun. 1999).

Steck, EA, et al., "*Leishmania donovani, Plasmodium berghei, Trypanosoma rhodesiense*: antiprotozoal effects of some amidine types," Exp Parasitol. Dec. 1981;52(3):404-13.

Tao Bin, et al., "Novel bisbenzamidines and bisbenzimidazolines as noncompetitive NMDA receptor antagonists," Bioorg. Med. Chem. Lett. 9(9), 1299-1304 (1999).

Tidwell, RR, et al "Strategies for anticoagulation with synthetic protease inhibitors. Xa inhibitors versus thrombin inhibitors," Thromb Res. Aug. 1, 1980;19(3):339-49.

Tidwell, RR, et al "Analogues of 1,5-bis(4-amidinophenoxy)pentane (pentamidine) in the treatment of experimental *Pneumocystis carinii* pneumonia," J Med Chem. Apr. 1990;33(4):1252-7.

Tidwell, RR, et al. "Aromatic amidines: comparison of their ability to block respiratory syncytial virus induced cell fusion and to inhibit plasmin, urokinase, thrombin, and trypsin," J Med Chem. Feb. 1983;26(2):294-8.

Tidwell, RR, et al. "Diarylamidine derivatives with one or both of the aryl moieties consisting of an indole or indole-like ring. Inhibitors of arginine-specific esteroproteases," J Med Chem. Jul. 1978;21(7):613-23.

Verner, E, et al., "Development of serine protease inhibitors displaying a multicentered short (<2.3 .ANG.) hydrogen bond binding mode: Inhibitors of urokinase-type plasminogen activator and factor Xa," Journal of Medicinal Chemistry (2001), 44(17), 2753-2771.

Wang, L et al., "Evaluation of the influence of compound structure on stacked-dimer formation in the DNA minor groove," Biochemistry. Feb. 27, 2001;40(8):2511-21.

Weidner-Wells, M. A., et al. "Amidino benzimidazole inhibitors of bacterial two-component systems," Bioorganic & Medicinal Chemistry Letters (2001), 11(12), 1545-1548.

Westermark, P., et al., "The pancreatic islet cells in insular amyloidosis in human diabetic and non-diabetic adults." Acta Pathol. Microbiol. Scand. [A] 81(3), 291-300 (May 1973).

Wilson, WD, et al., "The search for structure-specific nucleic acid-interactive drugs: effects of compound structure on RNA versus DNA interaction strength," Biochemistry. Apr. 20, 1993;32(15):4098-104.

Wood, DH, et al., "1,5-Bis(4-amidinophenoxy)pentane (pentamidine) is a potent inhibitor of [3H]idazoxan binding to imidazoline I2 binding sites." Eur. J. Pharmacol. 353(1), 97-103 (Jul. 1998).

Wood, DH, et al., "Pentamidine is a potent inhibitor of [3H]idazoxan binding to imidazoline I2 receptors." Ann. N.Y. Acad. Sci. 881, 110-13 (Jun. 1999).

Zhang, et al., "Biochemical characterization of the gamma-secretase activity that produces beta-amyloid peptides." Biochemistry 40(16), 5049-55 (Apr. 2001).

Zhang, et al., "Enantioselective synthesis of oxiranes by the reactions of dimethylsulfonium methylide and aromatic aldehydes and ketones in the presence of chiral micelles." Tetrahedron: Asymmetry 8(16), 2723-25 (1997).

Zhang, et al., "Calpain inhibitor I increases beta-amyloid peptide production by inhibiting the degradation of the substrate of gamma-secretase. Evidence that substrate availability limits beta-amyloid peptide production." J Biol Chem. 274(13):8966-72 Mar. 1999.

\* cited by examiner

AMIDINE DERIVATIVES FOR TREATING AMYLOIDOSIS

RELATED APPLICATIONS

This application is related to PCT patent application publication no. WO 2003/017,994.

BACKGROUND OF THE INVENTION

Amyloidosis refers to a pathological condition characterized by the presence of amyloid fibrils. Amyloid is a generic term referring to a group of diverse but specific protein deposits (intracellular or extracellular) which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common X-ray diffraction and infrared spectra.

Amyloid-related diseases can either be restricted to one organ or spread to several organs. The first instance is referred to as "localized amyloidosis" while the second is referred to as "systemic amyloidosis."

Some amyloidotic diseases can be idiopathic, but most of these diseases appear as a complication of a previously existing disorder. For example, primary amyloidosis can appear without any other pathology or can follow plasma cell dyscrasia or multiple myeloma.

Secondary amyloidosis is usually seen associated with chronic infection (such as tuberculosis) or chronic inflammation (such as rheumatoid arthritis). A familial form of secondary amyloidosis is also seen in Familial Mediterranean Fever (FMF). This familial type of amyloidosis, as one of the other types of familial amyloidosis, is genetically inherited and is found in specific population groups. In both primary and secondary amyloidosis, deposits are found in several organs and are thus considered systemic amyloid diseases.

Another type of systemic amyloidosis is found in long-term hemodialysis patients. In each of these cases, a different amyloidogenic protein is involved in amyloid deposition.

"Localized amyloidoses" are those that tend to involve a single organ system. Different amyloids are also characterized by the type of protein present in the deposit. For example, neurodegenerative diseases such as scrapie, bovine spongiform encephalitis, Creutzfeldt-Jakob disease, and the like are characterized by the appearance and accumulation of a protease-resistant form of a prion protein (referred to as AScr or PrP-27) in the central nervous system. Similarly, Alzheimer's disease, another neurodegenerative disorder, is characterized by neuritic plaques and neurofibrillary tangles. In this case, the plaque and blood vessel amyloid is formed by the deposition of fibrillary Aβ amyloid protein. Other diseases such as adult-onset diabetes (type II diabetes) are characterized by the localized accumulation of amyloid in the pancreas.

Once these amyloids have formed, there is no known, widely accepted therapy or treatment which significantly dissolves amyloid deposits in situ or that prevents further amyloid deposition. There is also no widely known or accepted therapy or treatment which prevents amyloid deposition from occuring.

Each amyloidogenic protein has the ability to organize into β-sheets and to form insoluble fibrils which may be deposited extracellularly or intracellularly. Each amyloidogenic protein, although different in amino acid sequence, has the same property of forming fibrils and binding to other elements such as proteoglycan, amyloid P and complement component. Moreover, each amyloidogenic protein has amino acid sequences which, although different, will show similarities such as regions with the ability to bind to the glycosaminoglycan (GAG) portion of proteoglycan (referred to as the GAG binding site) as well as other regions which will promote β-sheet formation.

In specific cases, amyloidotic fibrils, once deposited, can become toxic to the surrounding cells. For example, the Aβ fibrils organized as senile plaques have been shown to be associated with dead neuronal cells and microgliosis in patients with Alzheimer's disease. When tested in vitro, oligomeric as well as fibrillar Aβ peptide was shown to be capable of triggering an activation process of microglia (brain macrophages), which would explain the presence of microgliosis and brain inflammation found in the brain of patients with Alzheimer's disease. Both oligomeric and fibrillar Aβ peptide can also induce neuronal cell death in vitro.

In another type of amyloidosis seen in patients with type II diabetes, the amyloidogenic protein IAPP, when in its oligomeric form or when organized in fibrils, has been shown to induce β-islet cell toxicity in vitro. Hence, appearance of IAPP fibrils in the pancreas of type II diabetic patients contributes to the loss of the β islet cells (Langerhans) and organ dysfunction. Recent findings indicate that oligomeric IAPP can also be toxic.

People suffering from Alzheimer's disease develop a progressive dementia in adulthood, accompanied by three main structural changes in the brain: diffuse loss of neurons in multiple parts of the brain; accumulation of intracellular protein deposits termed neurofibrillary tangles; and accumulation of extracellular protein deposits termed amyloid or senile plaques, surrounded by misshapen nerve terminals (dystrophic neurites). A main constituent of these amyloid plaques is the amyloid-β peptide (Aβ), a 39-43 amino-acid protein that is produced through cleavage of the β-amyloid precursor protein (APP).

Extensive research has been conducted on the relevance of Aβ deposits in AD (D. J. Selkoe, *Trends in Cell Biology* 8, 447-53 (1998)). Aβ naturally arises from the metabolic processing of the amyloid precursor protein ("APP") in the endoplasmic reticulum ("ER"), the Golgi apparatus, or the endosomal-lysosomal pathway, and most is normally secreted as a 40 ("Aβ$_{1-40}$") or 42 ("Aβ$_{1-42}$") amino acid peptide (D. J. Selkoe, *Annu. Rev. Cell Biol.* 10, 373-403 (1994)). A role for Aβ as a primary cause for AD is supported by the presence of extracellular amyloid β peptide ("Aβ") deposits in senile plaques of Alzheimer's disease ("AD"), the increased production of Aβ in cells harboring mutant AD associated genes, e.g., amyloid precursor protein, presenilin I and presenilin II; the toxicity of extracellular fibrillar Aβ to cells in culture (reviewed by D. J. Selkoe, *Trends in Cell Biology* 8, 447-453 (1998)); and the toxicity of oligomeric non-fibrillar Aβ. See, e.g., F. Gervais, *European Biopharmaceutical Review*, 40-42, Autumn 2001; May, P. C., *DDT*, 6:459-462, 2001). Although symptomatic treatments exist for Alzheimer's disease, this disease cannot be prevented or cured at this time.

SUMMARY OF THE INVENTION

The present invention relates to the use of amidine compounds in the treatment of amyloid-related diseases. In particular, the invention relates to a method of treating or preventing an amyloid-related disease in a subject comprising administering to the subject a therapeutic amount of an amidine compound. Among the compounds for use in the invention are those according to the following Formula, such that, when administered, amyloid fibril formation, neurodegeneration, or cellular toxicity is reduced or inhibited:

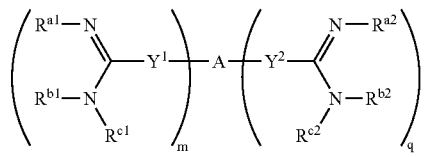

(Formula X)

In one embodiment, the amidine compounds disclosed herein prevent or inhibit amyloid protein assembly into insoluble fibrils which, in vivo, are deposited in various organs, or they reverse or slow deposition in subjects already having deposits. In another embodiment, the amidine compound may also prevent the amyloid protein from binding or adhering to a cell surface and causing cell damage or toxicity. In yet another embodiment, the compound may block amyloid-induced cellular toxicity or microglial activation. In another embodiment, the amidine compound may block amyloid-induced neurotoxicity.

The amidine compounds of the invention may be administered therapeutically or prophylactically to treat diseases associated with amyloid-β fibril formation, aggregation or deposition. The compounds of the invention may act to ameliorate the course of an amyloid-β related disease using any of the following mechanisms (this list is meant to be illustrative and not limiting): slowing the rate of amyloid-β fibril formation or deposition; lessening the degree of amyloid-β deposition; inhibiting, reducing, or preventing amyloid-β fibril formation; inhibiting neurodegeneration or cellular toxicity induced by amyloid-β; inhibiting amyloid-β induced inflammation; or enhancing the clearance of amyloid-β from the brain. The "amyloid-β disease" (or "amyloid-β related disease," which terms as used herein are synonymous) may be Mild Cognitive Impairment; vascular dementia; Alzheimer's disease, including sporadic (non-hereditary) Alzheimer's disease and familial (hereditary) Alzheimer's disease; cerebral amyloid angiopathy or hereditary cerebral hemorrhage; senile dementia; Down's syndrome; inclusion body myositis; or age-related macular degeneration.

Therapeutic compounds of the invention may be effective in controlling amyloid-β deposition either following their entry into the brain (following penetration of the blood brain barrier) or from the periphery. When acting from the periphery, a compound may alter the equilibrium of Aβ between the brain and the plasma so as to favor the exit of Aβ from the brain. An increase in the exit of Aβ from the brain would result in a decrease in Aβ brain concentration and therefore favor a decrease in Aβ deposition. Alternatively, compounds that penetrate the brain could control deposition by acting directly on brain Aβ, e.g., by maintaining it in a non-fibrillar form or favoring its clearance from the brain. These compounds could also prevent Aβ in the brain from interacting with a cell surface and therefore prevent neurotoxicity or inflammation.

In another embodiment, the method is used to treat Alzheimer's disease (e.g., sporadic or familial Alzheimer's disease).

Additionally, abnormal accumulation of APP and of amyloid-β protein in muscle fibers has been implicated in the pathology of sporadic inclusion body myositis (IBM) (Askanas, et al., Proc. Natl. Acad. Sci. USA 93, 1314-1319 (1996); Askanas, et al., Current Opinion in Rheumatology 7, 486-496 (1995)). Accordingly, the compounds of the invention can be used prophylactically or therapeutically in the treatment of disorders in which amyloid-beta protein is abnormally deposited at non-neurological locations, such as treatment of IBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration ("AMD"). AMD is a cause of irreversible vision loss in older individuals. It is believed that Aβ deposition could be an important component of the local inflammatory events that contribute to atrophy of the retinal pigmented epithelium, drusen biogenesis, and the pathogenesis of AMD (Johnson, et al., Proc. Natl. Acad. Sci. USA 99(18), 11830-5 (2002)).

The invention also pertains to new compounds and to pharmaceutical compositions comprising those compounds. The invention also pertains to pharmaceutical compositions for the treatment of amyloid-related diseases. In some embodiments, the pharmaceutical compositions comprise a compound as described herein that prevents or inhibits amyloid-β fibril formation, neurodegeneration, or cellular toxicity.

The present invention therefore relates to the use of amidine compounds in the prevention or treatment of amyloid-related diseases, including, inter alia, Alzheimer's disease, Mild Cognitive Impairment, cerebral amyloid angiopathy, inclusion body myositis, Down's syndrome, macular degeneration, and type II diabetes.

DETAILED DESCRIPTION OF THE INVENTION

The present invention relates to the use of amidine compounds in the treatment of amyloid-related diseases. For example, the invention relates to a method of treating or preventing an amyloid-related disease in a subject (for example, a human) comprising administering to the subject a therapeutic amount of a compound as described herein, such that amyloid fibril formation or deposition, neurodegeneration, or cellular toxicity is reduced or inhibited. In another embodiment, the invention relates to a method of treating or preventing an amyloid-related disease in a subject (for example, a human) comprising administering to the subject a therapeutic amount of a compound as described herein, such that cognitive function is improved or stabilized or further deterioration in cognitive function is prevented, slowed, or stopped in patients with brain amyloidosis, e.g., Alzheimer's disease or cerebral amyloid angiopathy. For convenience, some definitions of terms referred to herein are set forth below.

Amyloid-related Diseases

AA (Reactive) Amyloidosis

Generally, AA amyloidosis is a manifestation of a number of diseases that provoke a sustained acute phase response.

Such diseases include chronic inflammatory disorders, chronic local or systemic microbial infections, and malignant neoplasms.

AA fibrils are generally composed of 8,000 Dalton fragments (AA peptide or protein) formed by proteolytic cleavage of serum amyloid A protein (ApoSAA), a circulating apolipoprotein which once secreted is complexed with HDL and which is synthesized in hepatocytes in response to such cytokines as IL-1, IL-6 and TNF. Deposition can be widespread in the body, with a preference for parenchymal organs. The spleen is usually a deposition site, and the kidneys may also be affected. Deposition is also common in the heart and gastrointestinal tract.

AA amyloid diseases include, but are not limited to inflammatory diseases, such as rheumatoid arthritis, juvenile chronic arthritis, ankylosing spondylitis, psoriasis, psoriatic arthropathy, Reiter's syndrome, Adult Still's disease, Behcet's syndrome, and Crohn's disease. AA deposits are also produced as a result of chronic microbial infections, such as leprosy, tuberculosis, bronchiectasis, decubitus ulcers, chronic pyelonephritis, osteomyelitis, and Whipple's disease. Certain malignant neoplasms can also result in AA fibril amyloid deposits. These include such conditions as Hodgkin's lymphoma, renal carcinoma, carcinomas of gut, lung and urogenital tract, basal cell carcinoma, and hairy cell leukemia.

AL Amyloidoses

AL amyloid deposition is generally associated with almost any dyscrasia of the B lymphocyte lineage, ranging from malignancy of plasma cells (multiple myeloma) to benign monoclonal gammopathy. At times, the presence of amyloid deposits may be a primary indicator of the underlying dyscrasia.

Fibrils of AL amyloid deposits are composed of monoclonal immunoglobulin light chains or fragments thereof. More specifically, the fragments are derived from the N-terminal region of the light chain (kappa or lambda) and contain all or part of the variable ($V_L$) domain thereof. Deposits generally occur in the mesenchymal tissues, causing peripheral and autonomic neuropathy, carpal tunnel syndrome, macroglossia, restrictive cardiomyopathy, arthropathy of large joints, immune dyscrasias, myelomas, as well as occult dyscrasias. However, it should be noted that almost any tissue, particularly visceral organs such as the heart, may be involved.

Hereditary Systemic Amyloidoses

There are many forms of hereditary systemic amyloidoses. Although they are relatively rare conditions, adult onset of symptoms and their inheritance patterns (usually autosomal dominant) lead to persistence of such disorders in the general population. Generally, the syndromes are attributable to point mutations in the precursor protein leading to production of variant amyloidogenic peptides or proteins. Table 1 summarizes the fibril composition of exemplary forms of these disorders.

TABLE 1

Fibril Composition of Exemplary Amyloid-Related Diseases

| Fibril Peptide/Protein | Genetic Variant | Clinical Syndrome |
| --- | --- | --- |
| Transthyretin and fragments (ATTR) | Met30, many others | Familial amyloid polyneuropathy (FAP), (Mainly peripheral nerves) |
| Transthyretin and fragments (ATTR) | Thr45, Ala60, Ser84, Met111, Ile122 | Cardiac involvement predominant without neuropathy |
| N-terminal fragment of Apolipoprotein A1 (apoAI) | Arg26 | Familial amyloid polyneuropathy (FAP), (mainly peripheral nerves) |
| N-terminal fragment of Apoliproprotein A1(AapoAI) | Arg26, Arg50, Arg 60, others | Ostertag-type, non-neuropathic (predominantly visceral involvement) |
| Lysozyme (Alys) | Thr56, His67 | Ostertag-type, non-neuropathic (predominantly visceral involvement) |
| Fibrogen ∀ chain fragment | Leu554, Val 526 | Cranial neuropathy with lattic corneal dystrophy |
| Gelsolin fragment (Agel) | Asn187, Tyr187 | Cranial neuropathy with lattice corneal dystrophy |
| Cystatin C fragment | Glu68 | Hereditary cerebral hemorrhage (cerebral amyloid angiopathy) - Icelandic type |
| β-amyloid protein (Aβ) derived from Amyloid Precursor Protein (APP) | Gln693 | Hereditary cerebral hemorrhage (cerebral amyloid angiopathy) - Dutch type |
| β-amyloid protein (Aβ) derived from Amyloid Precursor | Ile717, Phe717, Gly717 | Familial Alzheimer's Disease |
| β-amyloid protein (Aβ) derived from Amyloid Precursor Protein (APP) | Asn670, Leu671 | Familial Dementia - probably Alzheimer's Disease |
| Prion Protein (PrP) derived from Prp precursor protein 51-91 insert | Leu102, Val167, Asn178, Lys200 | Familial Creutzfeldt-Jakob disease; Gerstmann-Sträussler-Scheinker syndrome (hereditary spongiform encephalopathies, prion diseases) |
| AA derived from Serum amyloid A protein (ApoSAA) | | Familial Mediterranean fever, predominant renal involvement (autosomal recessive) |
| AA derived from Serum amyloid A protein (ApoSAA) | | Muckle-Well's syndrome, nephropathy, deafness, urticaria, limb pain |
| Unknown | | Cardiomyopathy with persistent atrial standstill |
| Unknown | | Cutaneous deposits (bullous, papular, pustulodermal) |

Data derived from Tan SY, Pepys MB. Amyloidosis. Histopathology, 25(5), 403-414 (November 1994).

The data provided in Table 1 are exemplary and are not intended to limit the scope of the invention. For example, more than 40 separate point mutations in the transthyretin gene have been described, all of which give rise to clinically similar forms of familial amyloid polyneuropathy.

Transthyretin (TTR) is a 14 kiloDalton protein that is also sometimes referred to as prealbumin. It is produced by the liver and choroid plexus, and it functions in transporting thyroid hormones and vitamin A. At least 50 variant forms of the protein, each characterized by a single amino acid change, are responsible for various forms of familial amyloid polyneuropathy. For example, substitution of proline for leucine at position 55 results in a particularly progressive form of neuropathy; substitution of methionine for leucine at position 111 resulted in a severe cardiopathy in Danish patients.

Amyloid deposits isolated from heart tissue of patients with systemic amyloidosis have revealed that the deposits are composed of a heterogeneous mixture of TTR and fragments thereof, collectively referred to as ATTR, the full length sequences of which have been characterized. ATTR fibril components can be extracted from such plaques and their structure and sequence determined according to the methods known in the art (e.g., Gustavsson, A., et al., Laboratory Invest. 73: 703-708, 1995; Kametani, F., et al., Biochem. Biophys. Res. Commun. 125: 622-628, 1984; Pras, M., et al., PNAS 80: 539-42, 1983).

Persons having point mutations in the molecule apolipoprotein Al (e.g., Gly→Arg26; Trp→Arg50; Leu→Arg60) exhibit a form of amyloidosis ("Östertag type") characterized by deposits of the protein apolipoprotein AI or fragments thereof (AApoAI). These patients have low levels of high density lipoprotein (HDL) and present with a peripheral neuropathy or renal failure.

A mutation in the alpha chain of the enzyme lysozyme (e.g., Ile→Thr56 or Asp→His57) is the basis of another form of Östertag-type non-neuropathic hereditary amyloid reported in English families. Here, fibrils of the mutant lysozyme protein (Alys) are deposited, and patients generally exhibit impaired renal function. This protein, unlike most of the fibril-forming proteins described herein, is usually present in whole (unfragmented) form (Benson, M. D., et al. CIBA Fdn. Symp. 199: 104-131, 1996).

Amyloid-β peptide ("Aβ") is a 39-43 amino acid peptide derived by proteolysis from a large protein known as Beta Amyloid Precursor protein ("βAPP"). Mutations in βAPP result in familial forms of Alzheimer's disease, Down's syndrome or senile dementia, characterized by cerebral deposition of plaques composed of Aβ fibrils and other components, which are described in further detail below. Known mutations in APP associated with Alzheimer's disease occur proximate to the cleavage sites of β or gamma-secretase, or within Aβ. For example, position 717 is proximate to the site of gamma-secretase cleavage of APP in its processing to Aβ, and positions 670/671 are proximate to the site of β-secretase cleavage. Mutations at any of these residues may result in Alzheimer's disease, presumably by causing an increase in the amount of the 42/43 amino acid form of Aβ generated from APP. The structure and sequence of Aβ peptides of various lengths are well known in the art. Such peptides can be made according to methods known in the art, or extracted from the brain according to known methods (e.g., Glenner and Wong, Biochem Biophys. Res. Comm. 129: 885-890, 1984; Glenner and Wong, Biochem Biophys. Res. Comm. 122: 1131-1135, 1984). In addition, various forms of the peptides are commercially available.

As used herein, the term "β amyloid" or "amyloid-β" refer to amyloid β proteins or peptides, amyloid β precursor proteins or peptides, intermediates, and modifications and fragments thereof, unless otherwise specifically indicated. In particular, "Aβ" refers to any peptide produced by proteolytic processing of the APP gene product, especially peptides which are associated with amyloid pathologies, including $A\beta_{1-39}$, $A\beta_{1-40}$, $A\beta_{1-41}$, $A\beta_{1-42}$, and $A\beta_{1-43}$. For convenience of nomenclature, "$A\beta_{1-42}$" may be referred to herein as "Aβ(1-42) or simply as "$A\beta_{42}$" or "Aβ42" (and likewise for any other amyloid peptides discussed herein). As used herein, the terms "β amyloid," "amyloid-β," and "Aβ" are synonymous. Unless otherwise specified, the term "amyloid" refers to amyloidogenic proteins, peptides, or fragments thereof which can be soluble (e.g., monomeric or oligomeric) or insoluble (e.g., having fibrillary structure or in amyloid plaque). See, e.g., M P Lambert, et al., Proc. Nat'l Acad. Sci. USA 95, 6448-53 (1998).

According to certain aspects of the invention, amyloid-β is a peptide having 39-43 amino-acids, or amyloid-β is an amyloidogenic peptide produced from βAPP. The amyloid-β diseases that are the subject of the present invention include age-related cognitive decline, early Alzheimer's disease as seen in Mild Cognitive Impairment ("MCI"), vascular dementia, or Alzheimer's disease ("AD"), which may be sporadic (non-hereditary) Alzheimer's disease or familial (hereditary) Alzheimer's disease. The amyloid-β disease may also be cerebral amyloid angiopathy ("CAA") or hereditary cerebral hemorrhage. The amyloid-β disease may be senile dementia, Down's syndrome, inclusion body myositis ("IBM"), or age-related macular degeneration ("ARMD").

Gelsolin is a calcium binding protein that binds to fragments and actin filaments. Mutations at position 187 (e.g., Asp→Asn; Asp→Tyr) of the protein result in a form of hereditary systemic amyloidosis, usually found in patients from Finland, as well as persons of Dutch or Japanese origin. In afflicted individuals, fibrils formed from gelsolin fragments (Agel), usually consist of amino acids 173-243 (68 kDa carboxyterminal fragment) and are deposited in blood vessels and basement membranes, resulting in corneal dystrophy and cranial neuropathy which progresses to peripheral neuropathy, dystrophic skin changes and deposition in other organs. (Kangas, H., et al., Human Mol. Genet. 5(9): 1237-1243, 1996).

Other mutated proteins, such as mutant alpha chain of fibrinogen (AfibA) and mutant cystatin C (Acys) also form fibrils and produce characteristic hereditary disorders. AfibA fibrils form deposits characteristic of a normeuropathic hereditary amyloid with renal disease; Acys deposits are characteristic of a hereditary cerebral amyloid angiopathy reported in Iceland (Isselbacher, Harrison's Principles of Internal Medicine, McGraw-Hill, San Francisco, 1995; Benson, et al.). In at least some cases, patients with cerebral amyloid angiopathy (CAA) have been shown to have amyloid fibrils containing a non-mutant form of cystatin C in conjunction with amyloid beta protein (Nagai, A., et al., Molec. Chem. Neuropathol. 33: 63-78, 1998).

Certain forms of prion disease are now considered to be heritable, accounting for up to 15% of cases, which were previously thought to be predominantly infectious in nature. (Baldwin, et al., in Research Advances in Alzheimer's Disease and Related Disorders, John Wiley and Sons, New York, 1995). In such prion disorders, patients develop plaques composed of abnormal isoforms of the normal prion protein ($PrP^{Sc}$).

A predominant mutant isoform, $PrP^{Sc}$, also referred to as AScr, differs from the normal cellular protein in its resistance to protease degradation, insolubility after detergent extraction, deposition in secondary lysosomes, post-translational synthesis, and high β-pleated sheet content. Genetic linkage has been established for at least five mutations resulting in Creutzfeldt-Jacob disease (CJD), Gerstmann-Sträussler-Scheinker syndrome (GSS), and fatal familial insomnia (FH). (Baldwin, supra) Methods for extracting fibril peptides from scrapie fibrils, determining sequences and making such peptides are known in the art (e.g., Beekes, M., et al., J. Gen. Virol. 76: 2567-76, 1995).

For example, one form of GSS has been linked to a PrP mutation at codon 102, while telencephalic GSS segregates with a mutation at codon 117. Mutations at codons 198 and 217 result in a form of GSS in which neuritic plaques characteristic of Alzheimer's disease contain PrP instead of Aβ peptide. Certain forms of familial CJD have been associated with mutations at codons 200 and 210; mutations at codons 129 and 178 have been found in both familial CJD and FFI. (Baldwin, supra).

Senile Systemic Amyloidosis

Amyloid deposition, either systemic or focal, increases with age. For example, fibrils of wild type transthyretin (TTR) are commonly found in the heart tissue of elderly individuals. These may be asymptomatic, clinically silent, or may result in heart failure. Asymptomatic fibrillar focal deposits may also occur in the brain (Aβ), corpora amylacea of the prostate (Aβ$_2$ microglobulin), joints and seminal vesicles.

Cerebral Amyloidosis

Local deposition of amyloid is common in the brain, particularly in elderly individuals. The most frequent type of amyloid in the brain is composed primarily of Aβ peptide fibrils, resulting in dementia or sporadic (non-hereditary) Alzheimer's disease. In fact, the incidence of sporadic Alzheimer's disease greatly exceeds forms shown to be hereditary. Fibril peptides forming these plaques are very similar to those described above, with reference to hereditary forms of Alzheimer's disease ("AD").

Cerebral amyloid angiopathy ("CAA") refers to the specific deposition of amyloid fibrils in the walls of leptomingeal and cortical arteries, arterioles and in capillaries and veins. It is commonly associated with Alzheimer's disease, Down's syndrome and normal aging, as well as with a variety of familial conditions related to stroke or dementia (see Frangione et al., Amyloid: J. Protein Folding Disord. 8, Suppl. 1, 36-42 (2001)). CAA can occur sporadically or be hereditary. Multiple mutation sites in either Aβ or the APP gene have been identified and are clinically associated with either dementia or cerebral hemorrhage. Exemplary CAA disorders include, but are not limited to, hereditary cerebral hemorrhage with amyloidosis of Icelandic type (HCHWA-I); the Dutch variant of HCHWA (HCHWA-D; a mutation in Aβ); the Flemish mutation of Aβ; the Arctic mutation of Aβ; the Italian mutation of Aβ; the Iowa mutation of Aβ; familial British dementia; and familial Danish dementia.

Dialysis-Related Amyloidosis

Plaques composed of β$_2$ microglobulin (Aβ$_2$M) fibrils commonly develop in patients receiving long term hemodialysis or peritoneal dialysis. β$_2$ microglobulin is a 11.8 kiloDalton polypeptide and is the light chain of Class I MHC antigens, which are present on all nucleated cells. Under normal circumstances, it is continuously shed from cell membranes and is normally filtered by the kidney. Failure of clearance, such as in the case of impaired renal function, leads to deposition in the carpal tunnel and other sites (primarily in collagen-rich tissues of the joints). Unlike other fibril proteins, Aβ$_2$M molecules are generally present in unfragmented form in the fibrils. (Benson, supra).

Islet Amyloid Polypeptide and Diabetes

Islet hyalinosis (amyloid deposition) was first described over a century ago as the presence of fibrous protein aggregates in the pancreas of patients with severe hyperglycemia (Opie, E L., J Exp. Med. 5: 397-428, 1990). Today, islet amyloid, composed predominantly of islet amyloid polypeptide (IAPP), or amylin, is a characteristic histopathological marker in over 90% of all cases of type II diabetes (also known as Non-Insulin Dependent Diabetes, or NIDDM). These fibrillar accumulations result from the aggregation of the islet amyloid polypeptide (IAPP) or amylin, which is a 37 amino acid peptide, derived from a larger precursor peptide, called pro-IAPP.

IAPP co-localizes and is co-secreted with insulin in response to β-cell secretagogues. This pathological feature is not associated with insulin-dependent (type I) diabetes and is a unifying characteristic for the heterogeneous clinical phenotypes diagnosed as NIDDM (type II diabetes).

Longitudinal studies in cats and immunocytochemical investigations in monkeys have shown that a progressive increase in islet amyloid is associated with a dramatic decrease in the population of insulin-secreting β-cells and increased severity of the disease. More recently, transgenic studies have strengthened the relationship between IAPP plaque formation and β-cell dysfunction, indicating that amyloid deposition is a principal factor in Type-II diabetes.

IAPP has also been shown to induce β-islet cell toxicity in vitro, indicating that appearance of IAPP fibrils in the pancreas of type II or type I diabetic patients (post-transplantation) could contribute to the loss of the β islet cells (Langerhans) and organ dysfunction. In patients with Type-II diabetes, the accumulation of pancreatic IAPP leads to a buildup of IAPP-amyloid as insoluble fibrous deposits which eventually replace the insulin-producing β cells of the islet resulting in β cell depletion and failure (Westermark, P., Grimelius, L., *Acta Path. Microbiol. Scand., sect. A.* 81: 291-300, 1973; de Koning, E J P., et al., *Diabetologia* 36: 378-384, 1993; and Lorenzo, A., et al., *Nature* 368: 756-760, 1994).

Diseases caused by the death or malfunctioning of a particular type or types of cells can be treated by transplanting into the patient healthy cells of the relevant type of cell. This approach has been used for type I diabetes patients. Often pancreatic islet cells are cultured in vitro prior to transplantation to increase their numbers, to allow them to recover after the isolation procedure or to reduce their immunogenicity. However, in many instances islet cell transplantation is unsuccessful, due to death of the transplanted cells. One reason for this poor success rate is IAPP, which can form fibrils and become toxic to the cells in vitro. In addition, IAPP fibrils are likely to continue to grow after the cells are transplanted and cause death or dysfunction of the cells. This may occur even when the cells are from a healthy donor and the patient receiving the transplant does not have a disease that is characterized by the presence of fibrils. For example, compounds of the present invention may also be used in preparing tissues or cells for transplantation according to the methods described in International Patent Application (PCT) number WO 01/03,680.

Hormone-Derived Amyloidoses

Endocrine organs may harbor amyloid deposits, particularly in aged individuals. Hormone-secreting tumors may also contain hormone-derived amyloid plaques, the fibrils of which are made up of polypeptide hormones such as calcitonin (medullary carcinoma of the thyroid), islet amyloid polypeptide (amylin; occurring in most patients with type II diabetes), and atrial natriuretic peptide (isolated atrial amyloidosis). Sequences and structures of these proteins are well known in the art.

Miscellaneous Amyloidoses

There are a variety of other forms of amyloid disease that are normally manifest as localized deposits of amyloid. In general, these diseases are probably the result of the localized production or lack of catabolism of specific fibril precursors or a predisposition of a particular tissue (such as the joint) for fibril deposition. Examples of such idiopathic deposition include nodular AL amyloid, cutaneous amyloid, endocrine amyloid, and tumor-related amyloid.

The compounds of the invention may be administered therapeutically or prophylactically to treat diseases associated with amyloid-β fibril formation, aggregation or deposition. The compounds of the invention may act to ameliorate the course of an amyloid-β related disease using any of the following mechanisms (this list is meant to be illustrative and not limiting): slowing the rate of amyloid-β fibril formation or deposition; lessening the degree of amyloid-β deposition; inhibiting, reducing, or preventing amyloid-β fibril formation; inhibiting neurodegeneration or cellular toxicity induced by amyloid-β; inhibiting amyloid-β induced inflammation; or enhancing the clearance of amyloid-β from the brain.

Compounds of the invention may be effective in controlling amyloid-β deposition either following their entry into the brain (following penetration of the blood brain barrier) or from the periphery. When acting from the periphery, a compound may alter the equilibrium of Aβ between the brain and the plasma so as to favor the exit of Aβ from the brain. An increase in the exit of Aβ from the brain would result in a decrease in Aβ brain concentration and therefore favor a decrease in Aβ deposition. Alternatively, compounds that penetrate the brain could control deposition by acting directly on brain Aβ, e.g., by maintaining it in a non-fibrillar form or favoring its clearance from the brain.

In an embodiment, the method is used to treat Alzheimer's disease (e.g., sporadic or familial AD). The method can also be used prophylactically or therapeutically to treat other clinical occurrences of amyloid-β deposition, such as in Down's syndrome individuals, patients with Mild Cognitive Impairment, patients with cerebral amyloid angiopathy ("CAA"), or hereditary cerebral hemorrhage.

Additionally, abnormal accumulation of APP and of amyloid-β protein in muscle fibers has been implicated in the pathology of sporadic inclusion body myositis (IBM) (Askanas, V., et al. (1996) *Proc. Natl. Acad. Sci. USA* 93: 1314-1319; Askanas, V. et al. (1995) *Current Opinion in Rheumatology* 7: 486-496). Accordingly, the compounds of the invention can be used prophylactically or therapeutically in the treatment of disorders in which amyloid-beta protein is abnormally deposited at non-neurological locations, such as treatment of IBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration ("AMD"). AMD is a cause of irreversible vision loss in older individuals. It is believed that Aβ deposition could be an important component of the local inflammatory events that contribute to atrophy of the retinal pigmented epithelium, drusen biogenesis, and the pathogenesis of AMD (Johnson, et al., *Proc. Natl. Acad. Sci. USA* 99(18), 11830-5 (2002)).

The present invention therefore relates to the use of amidine compounds in the prevention or treatment of amyloid-related diseases, including, inter alia, Alzheimer's disease, Mild Cognitive Impairment, cerebral amyloid angiopathy, inclusion body myositis, Down's syndrome, and type II diabetes.

In one embodiment, compounds of the invention have at least two amidine moieties (for example, arylamidines or benzamidines).

In one particular embodiment, the present invention relates to the novel use of amidine compounds in the prevention or treatment of amyloid-related diseases, such as those disclosed in U.S. Pat. Nos. 5,428,051, 4,963,589, 5,202,320, 5,935,982, 5,521,189, 5,686,456, 5,627,184, 5,622,955, 5,606,058, 5,668,167, 5,667,975, 6,025,398, 6,214,883, 5,817,687, 5,792,782, 5,939,440, 6,017,941, 5,972,969, 6,046,226, 6,294,565 (B1), 6,156,779, 6,326, 395, 6,008,247, 6,127,554, 6,172,104, 4,940,723, 5,594,138, 5,602,172, 5,206,236, 5,843,980, 4,933,347, 5,668,166, 5,817,686, 5,723,495, 4,619,942, 5,792,782, 5,639,755, 5,643,935, and 5,578,631, each of which are hereby incorporated herein by reference in their entirety. Additional synthesis protocols may be found in PCT Patent Application Publication No. WO 2003/017,994. Still further additional examples and synthesis protocols may be found in U.S. Patent Application Publication No. 2002/0161043, incorporated herein by reference.

In another embodiment, the invention relates to a method of treating or preventing an amyloid-related disease in a subject (for example, a human) comprising administering to the subject a therapeutic amount of a compound according to the following Formula, such that amyloid fibril formation or deposition, neurodegeneration, or cellular toxicity is reduced or inhibited. In another embodiment, the invention relates to a method of treating or preventing an amyloid-related disease in a subject (for example, a human) comprising administering to the subject a therapeutic amount of a compound according to the following Formula, such that cognitive function is stabilized or further deterioration in cognitive function is prevented, slowed, or stopped in patients with brain amyloidosis, e.g., Alzheimer's disease or cerebral amyloid angiopathy:

(Formula X)

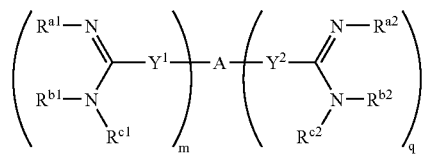

wherein
each of $R^{a1}$, $R^{b1}$, $R^{c1}$, $R^{a2}$, $R^{b2}$, and $R^{c2}$ is independently a hydrogen, a Z group, or $R^{a1}$ and $R^{b1}$ or $R^{a2}$ and $R^{b2}$ are both taken together along with the nitrogen atoms to which they are bound to form a ring structure;
each of $Y^1$ and $Y^2$ is independently a direct bond or a linking moiety;
m and q are each independently an integer selected from zero to five inclusive, such that $1 \leq m+q \leq 5$, or in another embodiment, $2 \leq m+q \leq 5$, or in another embodiment $1 \leq m+q \leq 10$, or in another embodiment, $2 \leq m+q \leq 10$; and
A is a carrier moiety selected from substituted or unsubstituted aliphatic and aromatic groups, and combinations thereof; for example, such that the $Y^1$ and $Y^2$ moieties are bonded to an aromatic group.

The A group may be a divalent group (i.e., m+q=2) such as an alkylene group (i.e., $-(CH_2)_k-$ and substituted analogs thereof (including groups in which a $-CH_2-$ moiety is substituted by an oxygen atom), where k is 1 to 12 (for example, 6 to 9, or 7 to 9), an alkenylene group (for example, 2 to 12 carbon atoms, or 6 to 9 carbon atoms, including groups with more than one double bond), an alkynylene group (for example, ably 2 to 12 carbon atoms, or 6 to 9 carbon atoms, including groups with more than one triple bond), an alkoxyalkylene group, an alkylaminoalkylene group, a thioalkoxyalkylene group, an arylenedialkylene group, a heteroarylenedialkylene group, an arylene group, a heteroarylene group, an oligoethereal group such as an oligo(alkyleneoxide) group, or an arylene-di(oligoalkyleneoxide) group, each of which may be substituted (with a Z group as defined below, e.g., a hydroxyalkylene group) or unsubstituted.

generation, or cellular toxicity is reduced or inhibited. In another embodiment, the invention relates to a method of treating or preventing an amyloid-related disease in a subject (for example, a human) comprising administering to the subject a therapeutic amount of a compound according to one of the following Formulae, such that cognitive function is stabilized or further deterioration in cognitive function is prevented, slowed, or stopped in patients with brain amyloidosis, e.g., Alzheimer's disease or cerebral amyloid angiopathy:

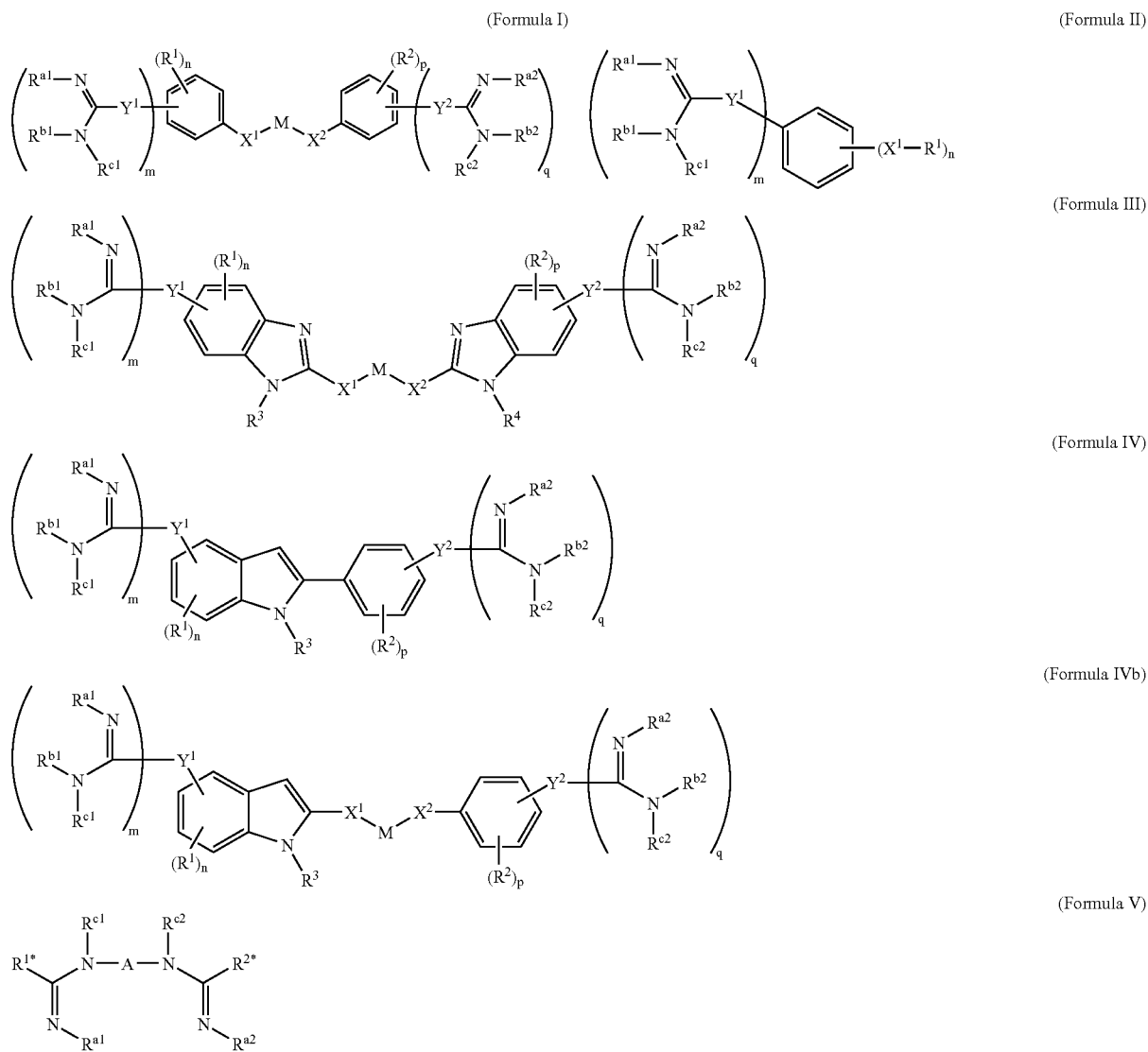

wherein each of $R^{a1}$, $R^{b1}$, $R^{c1}$, $R^{a2}$, $R^{b2}$, and $R^{c2}$ is independently a hydrogen, a Z group, or $R^{a1}$ and $R^{b1}$ or $R^{a2}$ and $R^{b2}$ are both taken together along with the nitrogen atoms to which they are bound to form a ring structure;

each of $Y^1$ and $Y^2$ is independently a direct bond or a joining moiety;

A is a carrier moiety selected from substituted or unsubstituted aliphatic and aromatic groups, and combina- The A group also includes the corresponding moieties of the Formulae I-IV herein as well as those moieties exemplified in by the compounds (and amyloid-targeting moieties) herein, including the groups in Table 2.

In some exemplary aspects of the invention, the invention relates to a method of treating or preventing an amyloid-related disease in a subject (for example, a human) comprising administering to the subject a therapeutic amount of a compound according to one of the following Formulae, such that amyloid fibril formation or deposition, neurodetions thereof; for example, such that the $Y^1$ and $Y^2$ moieties are bonded to an aromatic group;

each of $R^1$ and $R^2$ is independently a hydrogen or a Z group, or two adjacent or proximate $R^1$ and $R^2$ groups, along with the corresponding $X^1$ and $X^2$ groups, if present (e.g., in Formula II), taken together with the ring (e.g., phenyl ring) to which they are bound form a fused ring structure, e.g., an aromatic or heteroaromatic (e.g., benzofuran) structure, or a cycloalkyl or heterocylic structure;

each of $R^3$ and $R^4$ is independently selected from the group consisting of hydrogen, substituted or unsubstituted straight or branched alkyl (for example, $C_1$-$C_5$), cycloalkyl (for example, $C_3$-$C_8$), carbocyclic, aryl (e.g., phenyl), heterocyclic, and heteroaryl;

each of $R^{1*}$ and $R^{2*}$ is independently selected from the group consisting of substituted or unsubstituted straight or branched alkyl, cycloalkyl, heterocyclic, aryl (including phenyl), and heteroaryl;

each of $X^1$ and $X^2$ is independently a direct bond, or an oxygen, a NR' group (where R' is hydrogen (i.e., NH), a $C_1$-$C_5$ alkyl, $C_2$-$C_5$ alkenyl, $C_2$-$C_5$ alkynyl, or aryl group), a sulfonamide group (i.e., $NHSO_2$ or $SO_2NH$), a carbonyl, amide (i.e., NHCO or CONH), a $C_1$-$C_5$ alkylene group (e.g., —$CH_2$—), $C_2$-$C_5$ alkenylene group (e.g., E or Z —CH=CH—), $C_2$-$C_5$ alkynylene group, or a sulfur atom, or combinations thereof (e.g., —$OCH_2$—, —$CH_2O$—, E or Z —OCH=CH— or —CH=CHO—);

M is a divalent group such as an alkylene group, i.e., —$(CH_2)_k$— and substituted analogs thereof (including groups in which a —$CH_2$— moiety is substituted by an oxygen atom), where k is 1 to 12 (for example, 5 to 10, or 6 to 9, or even 7 to 8), an alkenylene group (for example, 2 to 12 carbon atoms, or 6 to 9 carbon atoms, including groups with more than one double bond), an alkynylene group (for example, 2 to 12 carbon atoms, or 6 to 9 carbon atoms, including groups with more than one triple bond), an alkoxyalkylene group, an alkylaminoalkylene group, a thioalkoxyalkylene group, an arylenedialkylene group, an alkylenediarylene group, a heteroarylenedialkylene group, an arylene group, a heteroarylene group, an oligoethereal group such as an oligo(alkyleneoxide) group, or an arylene-di(oligoalkyleneoxide) group, each of which may be substituted (with, for example, a Z group as defined herein, e.g., a hydroxyalkylene group such as —$(CH_2)_{0-6}(CHOH)(CH_2)_{0-6}$—; or other such substituted moieties, e.g., —$(CH_2)_{0-6}(CHZ)(CH_2)_{0-6}$—, including —$(CH_2)_{0-6}(CHCO_2alkyl)(CH_2)_{0-6}$—) or unsubstituted;

Z is a substituted or unsubstituted moiety selected from straight or branched alkyl (for example, $C_1$-$C_5$), cycloalkyl (for example, $C_3$-$C_8$), alkoxy (for example, $C_1$-$C_6$), thioalkyl (for example, $C_1$-$C_6$), alkenyl (for example, $C_2$-$C_6$), alkynyl (for example, $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{03}NR'R''$ (e.g., —$NH_2$), $(CR'R'')_{0-3}CN$ (e.g., —CN), $NO_2$, halogen (e.g., F, Cl, Br, or I), $(CR'R'')_{0-3}C(halogen)_3$ (e.g., —$CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., —$SO_3H$), $(CR'R'')_{0-3}O(CR'R'')_{0-3}H$ (e.g., —$CH_2OCH_3$ and —$OCH_3$), $(CR'R'')_{0-3}S(CR'R'')_{0-3}H$ (e.g., —SH and —$SCH_3$), $(CR'R'')_{0-3}OH$ (e.g., —OH), $(CR'R'')_{0-3}COR'$, $(CR'R'')_{0-3}$(substituted or unsubstituted phenyl), $(CR'R'')_{0-3}(C_3$-$C_8$ cycloalkyl), $(CR'R'')_{0-3}CO_2R'$ (e.g., —$CO_2H$), or $(CR'R'')_{0-3}OR'$ group, or the side chain of any naturally occurring amino acid;

m and q are each independently an integer selected from zero to five inclusive;

in Formula I, m and q are each independently an integer selected from zero to four inclusive, and n and p are each independently an integer selected from zero to four inclusive, such that m+n≦5 and p+q≦5, wherein either m or q is at least one; for example, m and q are one;

in Formula II, m is an integer selected from one to six inclusive, and n is an integer selected from zero to five inclusive, such that m+n≦6;

in Formula III, m, n, p, and q are each independently an integer selected from zero to three inclusive, m+n≦4, p+q≦4, and m+q≦1 (for example, m=q=1);

in Formula IV and IVb, m and n are each independently an integer selected from zero to three inclusive, p and q are each independently an integer selected from zero to four inclusive, m+n≦4, p+q≦5, and m+q≦1 (for example, m=q=1);

and pharmaceutically acceptable salts thereof.

In another embodiment, Z is a substituted or unsubstituted moiety selected from straight or branched alkyl (for example, $C_1$-$C_5$), cycloalkyl (for example, $C_3$-$C_8$), alkoxy (for example, $C_1$-$C_6$), thioalkyl (for example, $C_1$-$C_6$), alkenyl (for example, $C_2$-$C_6$), alkynyl (for example, $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-10}NR'R''$ (e.g., —$NH_2$), $(CR'R'')_{0-10}CN$ (e.g., —CN), $NO_2$, halogen (e.g., F, Cl, Br, or I), $(CR'R'')_{0-10}C(halogen)_3$ (e.g., —$CF_3$), $(CR'R'')_{0-10}CH(halogen)_2$, $(CR'R'')_{0-10}CH_2(halogen)$, $(CR'R'')_{0-10}CONR'R''$, $(CR'R'')_{0-10}(CNH)NR'R''$, $(CR'R'')_{0-10}S(O)_{1-2}NR'R''$, $(CR'R'')_{0-10}CHO$, $(CR'R'')_{0-10}O(CR'R'')_{0-10}H$, $(CR'R'')_{0-10}S(O)_{0-3}R'$ (e.g., —$SO_3H$), $(CR'R'')_{0-10}O(CR'R'')_{0-10}H$ (e.g., —$CH_2OCH_3$ and —$OCH_3$), $(CR'R'')_{0-10}S(CR'R'')_{0-3}H$ (e.g., —SH and —$SCH_3$), $(CR'R'')_{0-10}OH$ (e.g., —OH), $(CR'R'')_{0-10}COR'$, $(CR'R'')_{0-10}$ (substituted or unsubstituted phenyl), $(CR'R'')_{0-10}$ ($C_3$-$C_8$ cycloalkyl), $(CR'R'')_{0-10}CO_2R'$ (e.g., —$CO_2H$), or $(CR'R'')_{0-10}OR'$ group, or the side chain of any naturally occurring amino acid; wherein R' and R'' are each independently hydrogen, a $C_1$-$C_5$ alkyl, $C_2$-$C_5$ alkenyl, $C_2$-$C_5$ alkynyl, or aryl group, or R' and R'' taken together are a benzylidene group or a —$(CH_2)_2O(CH_2)_2$— group.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center may be of either (R)- or (S)-stereochemistry. Such isomers can be obtained in substantially pure form by classical separation techniques and by stereochemically-controlled synthesis. Furthermore, alkenes can include either the E- or Z-geometry, where appropriate. In addition, the compounds of the present invention may exist in unsolvated as well as solvated forms with acceptable solvents such as water, THF, ethanol, and the like. In general, the solvated forms are considered equivalent to the unsolvated forms for the purposes of the present invention. The compounds are typically synthetic and and may be isolated and purified to homogeneity.

In an alternate embodiment, the invention relates to novel compounds, and novel methods of their use as described herein, which are within the scope of the Formulae disclosed herein, and which are not disclosed in the above-referenced U.S. patents and patent applications.

The groups $R^{a1}$, $R^{b1}$, $R^{c1}$, $R^{a2}$, $R^{b2}$, and $R^{c2}$ in the above Formulae may be a hydrogen, or a substituted or unsubstituted $C_1$-$C_8$ alkyl or $C_1$-$C_8$ alkoxy group or a hydroxy group. Example $R^{a1}$ and $R^{a2}$ groups are hydrogen, hydroxyl, alkyloxy groups (especially lower alkyloxy groups, e.g. methoxy), aryloxy, acyloxy, and aroyloxy (i.e., R—(C=O)—O—, wherein R is aliphatic or aromatic).

The phrase "$R^a$ and $R^b$ both taken together along with the nitrogen atoms to which they are bound to form a ring structure" means that the two $R^a$ and $R^b$ groups are a moiety which joins the two nitrogen atoms in a heterocycle, such as the following ring structures:

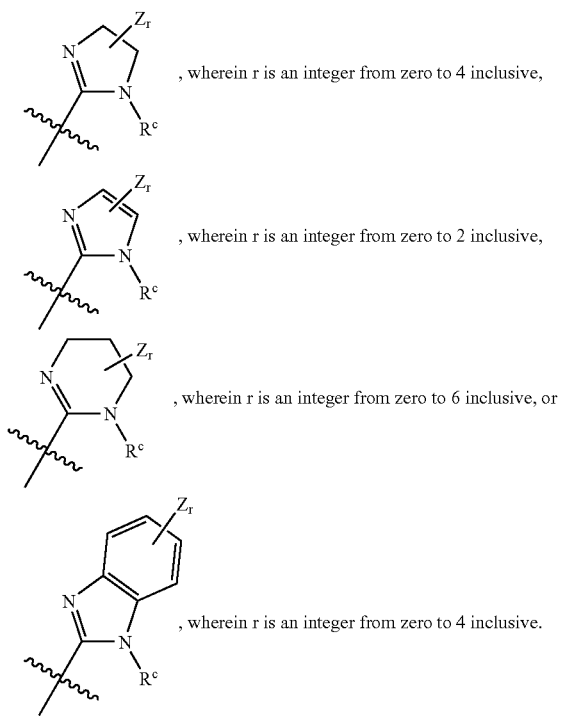

, wherein r is an integer from zero to 4 inclusive,

, wherein r is an integer from zero to 2 inclusive,

, wherein r is an integer from zero to 6 inclusive, or

, wherein r is an integer from zero to 4 inclusive.

"Pharmaceutically acceptable" denotes compounds, materials, compositions, or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" includes, for example, derivatives of compounds modified by making acid or base salts thereof, as described further below and elsewhere in the present application. Examples of pharmaceutically acceptable salts include mineral or organic acid salts of basic residues such as amines; and alkali or organic salts of acidic residues such as carboxylic acids. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic acid. Pharmaceutically acceptable salts may be synthesized from the parent compound which contains a basic or acidic moiety by conventional chemical methods. Generally, such salts may be prepared by reacting the free acid or base forms of these compounds with a stoichiometric amount of the appropriate base or acid in water or in an organic solvent, or in a mixture of the two.

In another embodiment of the invention, for example, in compounds of Formula II, $R^{a1}$ and $R^{b1}$ or $R^{a2}$ and $R^{b2}$ are both taken together along with the nitrogen atoms to which they are bound to form a ring structure which is a nonaromatic ring, or an alicyclic ring, or a monocyclic ring, or a non-fused ring.

In some embodiments of Formula II, e.g., $R^{a1}$, $R^{b1}$, $R^{c1}$, $R^{a2}$, $R^{b2}$, and $R^{c2}$ may be a hydrogen, or a substituted or unsubstituted $C_1$-$C_8$ alkyl group, wherein the alkyl substituent is any member of the group Z defined above, but not an aryl (e.g., phenyl) or alkyl group. Likewise, in certain embodiments of Formula II, $R^1$ is a moiety selected from the Z group defined above other than an substituted aryl (e.g., phenyl) or heteroaryl group.

The groups $R^1$ and $R^2$ may be a hydrogen, a substituted or unsubstituted $C_1$-$C_8$ alkyl group, a substituted or unsubstituted $C_2$-$C_8$ alkenyl group, a halogen (particularly bromine), a substituted or unsubstituted aryl or heteroaryl group, a substituted or unsubstituted amino group, a nitro group, or a substituted or unsubstituted $C_1$-$C_8$ alkoxy group (particularly methoxy).

Each Y group may be a direct bond, or a "linking moiety" (or "linking group") which is a group that is covalently bound to at least two other moieties and may be, for example, a single divalent atom or an oligomethylene group. A linking moiety which is a linear chain of carbon atoms may be optionally substituted or unsaturated.

A linking moiety is relatively small compared to the rest of the molecule, and may be less than about 250 molecular weight, and even less than about 75 molecular weight. Example linking moieties are —$(CH_2)_n$— (wherein n is 1, 2, or 3), —NR'— (where R' is hydrogen, a $C_1$-$C_5$ alkyl, $C_2$-$C_5$ alkenyl, $C_2$-$C_5$ alkynyl, or aryl group), —S—, —O—, —NH—$CH_2$—, and —CH=CH— (both E and Z configurations), or combinations thereof. The linking moiety may also be $(CR'R^w)_n$, $CR'OR^w(CR^xR^y)_n$, $CR'SH(CR^xR^y)_n$, $CR'NR^wR^x(CR^yR^z)_n$, $(CR'R^w)_nO(CR^xR^y)_n$, wherein each n is independently either 0, 1, 2, or 3, and $R^v$, $R^w$, $R^x$, $R^y$, and $R^z$ are each independently hydrogen, a substituted or unsubstituted $C_1$-$C_5$ branched or straight chain alkyl or alkoxy, $C_2$-$C_5$ branched or straight chain alkenyl, aryloxycarbonyl, arylaminocarbonyl, arylalkyl, acyl, aryl, or $C_3$-$C_8$ ring group.

In certain embodiments, $Y^1$ and $Y^2$ are each independently selected from the groups consisting of a direct bond, substituted or unsubstituted $C_1$-$C_8$ alkylene groups, and —NH—.

"Inhibition" of amyloid deposition includes preventing or stopping of amyloid formation, e.g., fibrillogenesis, inhibiting or slowing down of further amyloid deposition in a subject with amyloidosis, e.g., already having amyloid deposits, and reducing or reversing amyloid fibrillogenesis or deposits in a subject with ongoing amyloidosis. Inhibition of amyloid deposition is determined relative to an untreated subject, or relative to the treated subject prior to treatment, or, e.g., determined by clinically measurable improvement in pancreatic function in a diabetic patient, or in the case of a patient with brain amyloidosis, e.g., an Alzheimer's or cerebral amyloid angiopathy patient, stabilization of cognitive function or prevention of a further decrease in cognitive function or prevention of recurrence of hemorrhagic stroke due to CAA (i.e., preventing, slowing, or stopping disease progression). Inhibition of amyloid deposition may also be monitored by determining in a subject the relative levels of amyloid-β in the brain or CSF as well as in the plasma, before and after treatment.

"Modulation" of amyloid deposition includes both inhibition, as defined above, and enhancement of amyloid deposition or fibril formation. The term "modulating" is intended, therefore, to encompass prevention or stopping of amyloid formation or accumulation, inhibition or slowing down of further amyloid aggregation in a subject with ongoing amyloidosis, e.g., already having amyloid aggregates, and reducing or reversing of amyloid aggregates in a subject with ongoing amyloidosis; and enhancing amyloid deposition, e.g., increasing the rate or amount of amyloid deposition in vivo or in vitro. Amyloid-enhancing compounds may be useful in animal models of amyloidosis, for example, to make possible the development of amyloid deposits in animals in a shorter period of time or to increase amyloid deposits over a selected period of time. Amyloid-enhancing compounds may be useful in screening assays for compounds which inhibit amyloidosis in vivo, for example, in animal models, cellular assays and in vitro assays for amyloidosis. Such compounds may be used, for example, to provide faster or more sensitive assays for compounds. In some cases, amyloid enhancing compounds may also be administered for therapeutic purposes, e.g., to enhance the deposition of amyloid in the lumen rather than the wall of cerebral blood vessels to prevent CAA. Modulation of amyloid aggregation is determined relative to an untreated subject or relative to the treated subject prior to treatment.

The term "subject" includes living organisms in which amyloidosis can occur. Examples of subjects include humans, monkeys, cows, sheep, goats, dogs, cats, mice, rats, and transgenic species thereof. Administration of the compositions of the present invention to a subject to be treated can be carried out using known procedures, at dosages and for periods of time effective to modulate amyloid aggregation in the subject as further described herein. An effective amount of the therapeutic compound necessary to achieve a therapeutic effect may vary according to factors such as the amount of amyloid already deposited at the clinical site in the subject, the age, sex, and weight of the subject, and the ability of the therapeutic compound to modulate amyloid aggregation in the subject. Dosage regimens can be adjusted to provide the optimum therapeutic response. For example, several divided doses may be administered daily or the dose may be proportionally reduced as indicated by the exigencies of the therapeutic situation. The term "modulating" is intended to encompass prevention or stopping of amyloid formation or accumulation, inhibition or slowing down of further amyloid aggregation in a subject with ongoing amyloidosis, e.g., already having amyloid aggregates, and reducing or reversing of amyloid aggregates in a subject with ongoing amyloidosis. Modulation of amyloid aggregation is determined relative to an untreated subject or relative to the treated subject prior to treatment.

In an exemplary aspect of the invention, the subject is a human. For example, the subject may be a human over about 40 years old, or a human over about 50 years old, or a human over about 60 years old, or even a human over about 70 years old, or in some cases a human over about 80 years old. The subject may be a female human, including a postmenopausal female human, who may be on hormone (estrogen) replacement therapy. The subject may also be a male human. When the subject is a human with Down's syndrome, the age may be over about 20 years old; or in another embodiment, the age may be less than about 40 years old.

A subject may be a human at risk for Alzheimer's disease, e.g., being over the age of 40 or having a predisposition for Alzheimer's disease. Alzheimer's disease predisposing factors identified or proposed in the scientific literature include, among others, a genotype predisposing a subject to Alzheimer's disease; environmental factors predisposing a subject to Alzheimer's disease; past history of infection by viral and bacterial agents predisposing a subject to Alzheimer's disease; and vascular factors predisposing a subject to Alzheimer's disease. A subject may also have one or more risk factors for cardiovascular disease (e.g., atherosclerosis of the coronary arteries, angina pectoris, and myocardial infarction) or cerebrovascular disease (e.g., atherosclerosis of the intracranial or extracranial arteries, stroke, syncope, and transient ischemic attacks), such as hypercholesterolemia, hypertension, diabetes, cigarette smoking, familial or previous history of coronary artery disease, cerebrovascular disease, and cardiovascular disease. Hypercholesterolemia typically is defined as a serum total cholesterol concentration of greater than about 5.2 mmol/L (about 200 mg/dL).

Several genotypes are believed to predispose a subject to Alzheimer's disease. These include the genotypes such as presenilin-1, presenilin-2, and amyloid precursor protein (APP) missense mutations associated with familial Alzheimer's disease, and α-2-macroglobulin and LRP-1 genotypes, which are thought to increase the risk of acquiring sporadic (late-onset) Alzheimer's disease. E. van Uden, et al., *J. Neurosci.* 22(21), 9298-304 (2002); J. J. Goto, et al., *J. Mol. Neurosci.* 19(1-2), 37-41 (2002). Another genetic risk factor for the development of Alzheimer's disease are variants of ApoE, the gene that encodes apolipoprotein E (particularly the apoE4 genotype), a constituent of the low-density lipoprotein particle. W J Strittmatter, et al., *Annu. Rev. Neurosci.* 19, 53-77 (1996). The ApoE4 allele has been shown to influence the rate of amyloid-β deposition as well as to favor trapping of amyloid-β in the brain, which may increase the levels of amyloid-β that can become fibrillar. The molecular mechanisms by which the various ApoE alleles alter the likelihood of developing Alzheimer's disease are unknown, however the role of ApoE in cholesterol metabolism is consistent with the growing body of evidence linking cholesterol metabolism to Alzheimer's disease. Environmental factors have been proposed as predisposing a subject to Alzheimer's disease, including exposure to aluminum, although the epidemiological evidence is ambiguous. In addition, prior infection by certain viral or bacterial agents may predispose a subject to Alzheimer's disease, including the herpes simplex virus and *chlamydia*

*pneumoniae*. Finally, other predisposing factors for Alzheimer's disease can include risk factors for cardiovascular or cerebrovascular disease, including cigarette smoking, hypertension and diabetes. "At risk for Alzheimer's disease" also encompasses any other predisposing factors not listed above or as yet identified and includes an increased risk for Alzheimer's disease caused by head injury, medications, diet, or lifestyle.

The methods of the present invention can be used for one or more of the following: to prevent, to treat Alzheimer's disease, or ameliorate symptoms of Alzheimer's disease, to regulate production of or levels of amyloid-β (Aβ) peptides. In one alternative embodiment, the human carries one or more mutations in the genes that encode β-amyloid precursor protein, presenilin-1 or presenilin-2. In another alternative embodiment, the human carries the Apolipoprotein ε4 gene. In another alternative embodiment, the human has a family history of Alzheimer's Disease or dementia illness. In another alternative embodiment, the human has trisomy 21 (Down's Syndrome). In another alternative embodiment, the subject has a normal or low serum total blood cholesterol level. In another embodiment, the serum total blood cholesterol level is less than about 200 mg/dL, or less than about 180, and it can range from about 150 to about 200 mg/dL. In another embodiment, the total LDL cholesterol level is less than about 100 mg/dL, or less than about 90 mg/dL and can range from about 30 to about 100 mg/dL. Methods of measuring serum total blood cholesterol and total LDL cholesterol are well known to those skilled in the art and for example include those disclosed in WO 99/38498 at p. 11, incorporated by reference herein. Methods of determining levels of other sterols in serum are disclosed in H. Gylling, et al., "Serum Sterols During Stanol Ester Feeding in a Mildly Hypercholesterolemic Population", *J. Lipid Res.* 40: 593-600 (1999).

In another alternative embodiment, the subject has an elevated serum total blood cholesterol level. In another embodiment, the serum total cholesterol level is at least about 200 mg/dL, or at least about 220 mg/dL and can range from about 200 to about 1000 mg/dL. In another alternative embodiment, the subject has an elevated total LDL cholesterol level. In another embodiment, the total LDL cholesterol level is greater than about 100 mg/dL, or even greater than about 110 mg/dL and can range from about 100 to about 1000 mg/dL.

In another alternative embodiment, the human is at least about 40 years of age. In another alternative embodiment, the human is at least about 60 years of age. In another embodiment, the human is at least about 70 years of age. In yet another embodiment, the human is at least about 80 years of age. In one embodiment, the human is between about 60 and 100 years of age.

In still a further embodiment, the subject is shown to be at risk by a diagnostic brain imaging technique, for example, that measures brain activity, plaque deposition, or brain atrophy. For example, positron emission tomography ("PET") may be used to measure brain activity and plaque deposition, while magnetic resonance imaging ("MRI") may be used to measure the brain volume of a subject.

In another embodiment, the subject exhibits no symptoms of Alzheimer's Disease. In another embodiment, the subject is a human who is at least 40 years of age and exhibits no symptoms of Alzheimer's Disease. In another embodiment, the subject is a human who is at least 40 years of age and exhibits one or more symptoms of Alzheimer's Disease.

In another embodiment, the subject has mild cognitive impairment ("MCI"), which is a condition characterized by a state of mild but measurable impairment in thinking skills, but is not necessarily associated with the presence of dementia. MCI frequently, but not necessarily, precedes Alzheimer's disease. It is a diagnosis that has most often been associated with mild memory problems, but it can also be characterized by mild impairments in other thinking skills, such as language or planning skills. However, in general, an individual with MCI will have more significant memory lapses than would be expected for someone of their age or educational background. As the condition progresses, a physician may change the diagnosis to Mild-to-Moderate Cognitive Impairment or to Alzheimer's disease, as is well understood in the art.

By using the methods of the present invention, the levels of amyloid β peptides in a subject's brain or blood can be reduced from levels prior to treatment from about 10 to about 100 percent, or even about 50 to about 100 percent. Alternatively, the levels of amyloid-β peptides in a subject's blood or plasma may be increased from levels prior to treatment due to, for example, a "sink" effect (i.e., facilitating clearance of amyloid-β out of the brain).

In an alternative embodiment, the subject can have an elevated level of amyloid $A\beta_{40}$ and $A\beta_{42}$ peptide in the blood and CSF prior to treatment, according to the present methods, of greater than about 10 pg/mL, or greater than about 20 pg/mL, or greater than about 35 pg/mL, or even greater than about 40 pg/mL. In another embodiment, the elevated level of amyloid $A\beta_{42}$ peptide can range from about 30 pg/mL to about 200 pg/mL, or even to about 500 pg/mL. One skilled in the art would understand that as Alzheimer's disease progresses, the measurable levels of amyloid-β peptide in the CSF may decrease slightly from elevated levels present before onset of the disease. This effect is attributed to increased deposition, i.e., trapping of Aβ peptide in the brain instead of normal clearance from the brain into the CSF.

In an alternative embodiment, the subject can have an elevated level of amyloid $A\beta_{40}$ peptide in the blood and CSF prior to treatment, according to the present methods, of greater than about 5 pg $A\beta_{40}$/mL or greater than about 50 pg $A\beta_{40}$/mL, or greater than about 400 pg/mL. In another embodiment, the elevated level of amyloid $A\beta_{40}$ peptide can range from about 200 pg/mL to about 800 pg/mL, to even about 1000 pg/mL.

In another embodiment, the subject can have an elevated level of amyloid $A\beta_{42}$ peptide in the CSF prior to treatment, according to the present methods, of greater than about 5 pg/mL, or greater than about 10 pg/mL, or greater than about 200 pg/mL, or greater than about 500 pg/mL. In another embodiment, the level of amyloid-β peptide can range from about 10 pg/mL to about 1,000 pg/mL, or even about 100 pg/mL to about 1,000 pg/mL.

In another embodiment, the subject can have an elevated level of amyloid $A\beta_{40}$ peptide in the CSF prior to treatment according to the present methods of greater than about 10 pg/mL, or greater than about 50 pg/mL, or even greater than about 100 pg/mL. In another embodiment, the level of amyloid β peptide can range from about 10 pg/mL to about 1,000 pg/mL.

The amount of amyloid β peptide in the brain or blood of a subject can be evaluated by enzyme-linked immunosorbent assay ("ELISA") or quantitative immunoblotting test methods or by quantitative SELDI-TOF which are well known to those skilled in the art, such as is disclosed by Zhang, et al., *J. Biol. Chem.* 274, 8966-72 (1999) and Zhang, et al., *Biochemistry* 40, 5049-55 (2001). See also, A. K. Vehmas, et al., *DNA Cell Biol.* 20(11), 713-21 (2001), P. Lewczuk, et al., *Rapid Commun. Mass Spectrom.* 17(12), 1291-96 (2003); B. M. Austen, et al., *J. Peptide Sci.* 6, 459-69 (2000); and H. Davies, et al., *BioTechniques* 27, 1258-62 (1999). These tests are performed on samples of the brain or blood which have been prepared in a manner well known to one skilled in the art. Another example of a useful method for measuring levels of amyloid β peptides is by Europium immunoassay (EIA). See, e.g., WO 99/38498 at p. 11.

In another embodiment, the amount of total ApoE in the bloodstream or brain of a subject can be reduced from levels prior to treatment by about 5 to about 75 percent, or, in another embodiment, by about 5 to about 50 percent. The amount of total ApoE can be measured in a manner well known to one skilled in the art, for example using an ELISA test kit such as Apo-Tek ApoE test kit that is available from Organon Teknica.

The methods of the invention may be applied as a therapy for a subject having Alzheimer's disease or a dementia, or the methods of the invention may be applied as a prophylaxis against Alzheimer's disease or dementia for subject with such a predisposition, as in a subject, e.g., with a genomic mutation in the APP gene, the ApoE gene, or a presenilin gene. The subject may have (or may be predisposed to developing or may be suspected of having) vascular dementia, or senile dementia, or Mild Cognitive Impairment. In addition to Alzheimer's disease, the subject may have another amyloid-β related disease such as cerebral amyloid angiopathy, or the subject may have amyloid deposits, especially amyloid-β amyloid deposits in the subject's brain.

The essential features of a dementia are multiple cognitive deficits that include memory impairment and at least one of the following: aphasia, apraxia, agnosia, or a disturbance in executive functioning (the ability to think abstractly and to plan, initiate, sequence, monitor, and stop complex behavior). The order of onset and relative prominence of the cognitive disturbances and associated symptoms vary with the specific type of dementia, as discussed in the following.

Memory impairment is generally a prominent early symptom. Individuals with dementia have difficulty learning new material and may lose valuables, such as wallets and keys, or forget food cooking on the stove. In more severe dementia, individuals also forget previously learned material, including the names of loved ones. Individuals with dementia may have difficulty with spatial tasks, such as navigating around the house or in the immediate neighborhood (where difficulties with memory are unlikely to play a role). Poor judgment and poor insight are common as well. Individuals may exhibit little or no awareness of memory loss or other cognitive abnormalities. They may make unrealistic assessments of their abilities and make plans that are not congruent with their deficits and prognosis (e.g., planning to start a new business). They may underestimate the risks involved in activities (e.g., driving).

In order to make a diagnosis of dementia, the cognitive deficits must be sufficiently severe to cause impairment in occupational or social functioning and must represent a decline from a previous level of functioning. The nature and degree of impairment are variable and often depend on the particular social setting of the individual. For example, Mild Cognitive Impairment may significantly impair an individual's ability to perform a complex job but not a less demanding one.

Cognitive or degenerative brain disorders are characterized clinically by progressive loss of memory, cognition, reasoning, judgment and emotional stability that gradually leads to profound mental deterioration and ultimately death.

It is generally believed that the disease begins a number of years before it manifests itself in the mild cognitive changes that are the early signs of Alzheimer's disease. "Dementia of the Alzheimer's Type" begins gradually, and is usually diagnosed after other specific causes have been ruled out. Diagnostic criteria for Dementia of the Alzheimer's Type include the development of multiple cognitive deficits manifested by both memory impairment (anterograde or retrograde, i.e., impaired ability to learn new information or to recall previously learned information); and one or more of the following cognitive disturbances: aphasia (language disturbance), apraxia (impaired ability to carry out motor activities despite intact motor function), agnosia (failure to recognize or identify objects despite intact sensory function), disturbance in executive functioning (i.e., planning, organizing, sequencing, and abstracting); where these cognitive deficits each cause significant impairment in social or occupational functioning and represent a significant decline from a previous level of functioning. The course is characterized by gradual onset and continuing cognitive decline, and the cognitive deficits are not due to another condition that causes progressive deficits in memory and cognition (e.g., cerebrovascular disease, brain tumor, hypothyroidism, vitamin B or folic acid deficiency, niacin deficiency, hypercalcemia, neurosyphilis, HIV infection, or chemical exposure). The cognitive disturbance may be accompanied by a behavioral disturbance, such as wandering, aggression, or agitation, or a psychological disturbance, such as depression or psychosis. See "Diagnostic and Statistical Manual of Mental Disorders," $4^{th}$ Ed., Text Revision, by American Psychiatric Association (2000). For example, the National Institute of Neuro-logical and Communicative Disorders and Stroke-Alzheimer's Disease and the Alzheimer's Disease and Related Disorders Association (NINCDS-ADRDA) criteria can be used to diagnose Alzheimer's Disease (McKhann et al., 1984, *Neurology* 34: 939-944). The patient's cognitive function can be assessed by the Alzheimer's Disease Assessment Scale-cognitive subscale (ADAS-cog; Rosen, et al., 1984, *Am. J. Psychiatry* 141: 1356-1364).

Alzheimer's Disease is the prototype of a cortical degenerative disease. A major component of the presenting symptoms is usually subjective complaints of memory difficulty, language impairment, dyspraxia, at which point diagnosis is primarily based on exclusion of other possible etiologies for dementia. No features of the physical examination or laboratory evaluation are pathognomonic for dementia of the Alzheimer's type. Some studies have apparently discriminated patients with dementia of the Alzheimer's type from patients with dementia of other etiologies and from normal controls by using techniques such as EEG, MRI, and SPECT, but these studies have been difficult to replicate consistently, and at present, brain-imaging studies are best used to exclude other identifiable causes.

A variety of diagnostic tests have been developed for Alzheimer's disease. Clinical criteria have been verified prospectively in autopsy studies and have been found to be highly specific although only moderately sensitive. Implementation of the criteria requires extensive evaluation, including an informant-based history, neurological examination, neuropsychological testing, and laboratory, and neuroimaging data. Alzheimer's disease is characterized pathologically by generalized atrophy of the cerebral cortex and by neurofibrillary tangles, neuritic (amyloid) plaques, and granulovacuolar degeneration. Although plaques and tangles may be detected in the brains of the elderly without Alzheimer's disease, they are more numerous in patients with dementia. Controversy remains whether brains with plaques from individuals without Alzheimer's disease were "normal variations" or early pathological signs of incipient disease.

"Treatment" of a subject includes the application or administration of a composition of the invention to a subject, or application or administration of a composition of the invention to a cell or tissue from a subject, who has a amyloid-β related disease or condition, has a symptom of such a disease or condition, or is at risk of (or susceptible to) such a disease or condition, with the purpose of curing, healing, alleviating, relieving, altering, remedying, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination or a psychiatric evaluation. For example, the methods of the invention successfully treat a subject's dementia by slowing the rate of or extent of cognitive decline.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl, etc.), alkyl substituted cycloalkyl groups, and cycloalkyl substituted alkyl groups. Unless otherwise specified, the term alkyl further includes alkyl groups, which can further include oxygen, nitrogen, sulfur or phosphorous atoms replacing one or more carbons of the hydrocarbon backbone.

In certain embodiments, a straight chain or branched chain alkyl has 6 or fewer carbon atoms in its backbone (e.g., $C_1$-$C_6$ for straight chain, $C_3$-$C_6$ for branched chain), or 4 or fewer. Likewise, cycloalkyls may have from 3-8 carbon atoms in their ring structure, or 5 or 6 carbons in the ring structure. The term $C_1$-$C_6$ includes alkyl groups containing 1 to 6 carbon atoms. An "alkylene" group is a divalent moiety derived from the corresponding alkyl group.

Moreover, unless otherwise specified the term alkyl includes both "unsubstituted alkyls" and "substituted alkyls," the latter of which refers to alkyl moieties having substituents replacing one or more hydrogens on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls may be further substituted, e.g., with the substituents described above.

An "arylalkyl" moiety is an alkyl group substituted with an aryl (e.g., phenylmethyl (i.e., benzyl)). An "alkylaryl" moiety is an aryl group substituted with an alkyl group (e.g., p-methylphenyl (i.e., p-tolyl)). The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclobutenyl, cyclopentenyl, cyclohexenyl, cycloheptenyl, cyclooctenyl, etc.), alkyl or alkenyl substituted cycloalkenyl groups, and cycloalkyl or cycloalkenyl substituted alkenyl groups. The term alkenyl may further include alkenyl groups which include oxygen, nitrogen, sulfur or phosphorous atoms replacing one or more carbons of the hydrocarbon backbone.

In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, or 5 or 6 carbons in the ring structure. The term $C_2$-$C_6$ includes alkenyl groups containing 2 to 6 carbon atoms. An "alkenylene" group is a divalent moiety derived from the corresponding alkenyl group.

Moreover, unless otherwise specified the term alkenyl includes both "unsubstituted alkenyls" and "substituted alkenyls," the latter of which refers to alkenyl moieties having substituents replacing one or more hydrogens on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate (and lower alkyl esters thereof), alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. Unless specified otherwise, the term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms. An "alkynylene" group is a divalent moiety derived from the corresponding alkynyl group.

Moreover, unless otherwise specified the term alkynyl includes both "unsubstituted alkynyls" and "substituted alkynyls," the latter of which refers to alkynyl moieties having substituents replacing one or more hydrogens on one or more carbons of the hydrocarbon backbone.

Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" refers to a carbonyl group that is attached through its carbon atom to a hydrogen (i.e., a formyl), an aliphatic group (e.g., acetyl), an aromatic group (e.g., benzoyl), and the like. The term "substituted acyl" includes acyl groups where one or more of the hydrogen atoms on one or more carbon atoms are replaced by, for example, an alkyl group, alkynyl group, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an amino moiety is bonded to an acyl group. For example, the acylamino group includes alkylcarbonylamino, arylcarbonylamino, carbamoyl and ureido groups.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone.

The terms "alkoxy" or "alkyloxy" include substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups.

The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc., as well as perhalogenated alkyloxy groups.

The term "amine" or "amino" includes compounds or moieties in which a nitrogen atom is covalently bonded to at least one carbon or heteroatom. The term "alkylamino" includes groups wherein the nitrogen is bound to at least one alkyl group. The term "dialkylamino" includes groups wherein the nitrogen atom is bound to at least two alkyl groups. The term "arylamino" and "diarylamino" include groups wherein the nitrogen is bound to at least one or two aryl groups, respectively. The term "alkylarylamino" refers to an amino group which is bound to at least one alkyl group and at least one aryl group. The term "alkaminoalkyl" refers to an alkyl, alkenyl, or alkynyl group substituted with an alkylamino group. The term "amide" or "aminocarbonyl" includes compounds or moieties which contain a nitrogen atom which is bound to the carbon of a carbonyl or a thiocarbonyl group.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "ether" or "ethereal" includes compounds or moieties which contain an oxygen bonded to two carbon atoms. For example, an ether or ethereal group includes "alkoxyalkyl" which refers to an alkyl, alkenyl, or alkynyl group substituted with an alkoxy group.

The term "hydroxy" or "hydroxyl" includes the groups —OH or —O— (with an appropriate counter ion).

The term "halogen" includes fluorine, bromine, chlorine, iodine, etc. The term "perhalogenated" generally refers to a moiety wherein all hydrogens are replaced by halogen atoms.

Arylenedialkylene or arylenedialkyl groups include those groups which have an arylene group to which are bound two other alkylene groups, which may be the same or different, and which two alkylene groups are in turn bound to other moieties. Examples of arylenedialkylene or arylenedialkyl groups include the following:

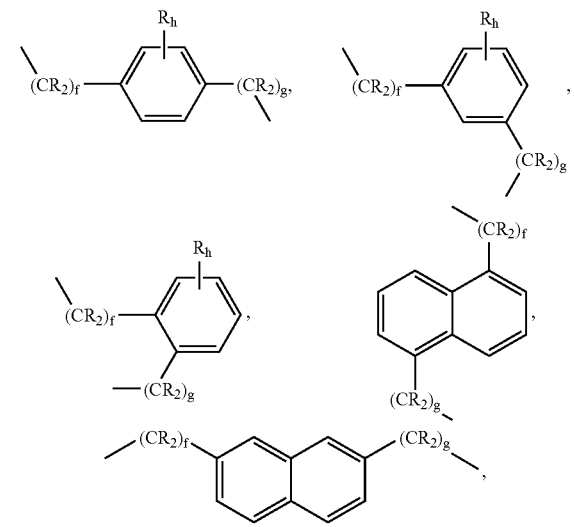

-continued

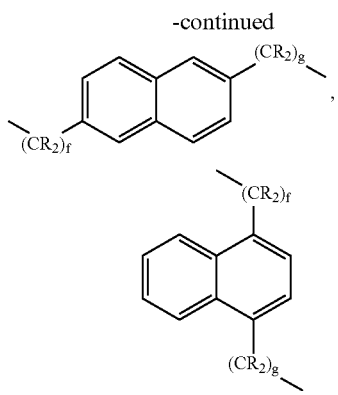

, and

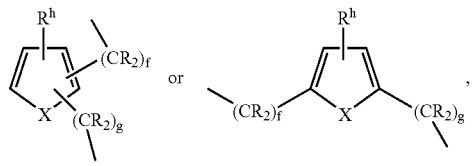

wherein $0 \leq h \leq 2$, and X=NR' (wherein R' is hydrogen, a $C_1$-$C_5$ alkyl, $C_2$-$C_5$ alkenyl, $C_2$-$C_5$ alkynyl, or aryl group), O, or S, $1 \leq f \leq 8$, $1 \leq g \leq 8$, wherein each R group is independently a hydrogen or is selected from the group Z defined above, and $1 \leq f \leq 8$, $1 \leq g \leq 8$, $0 \leq h \leq 4$.

Alkylenediarylene groups include groups which have an alkylene (or cycloalkylene) group to which are bound two other arylene groups, which may be the same or different, and which two alkylene groups are in turn bound to other moieties. Examples of alkylenediarylene groups include the following:

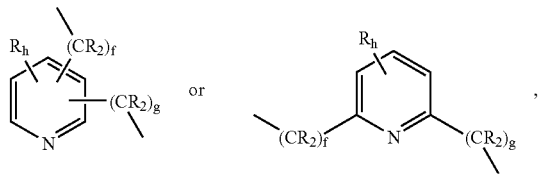

wherein $0 \leq h \leq 3$, $1 \leq f \leq 8$, $1 \leq g \leq 8$, or

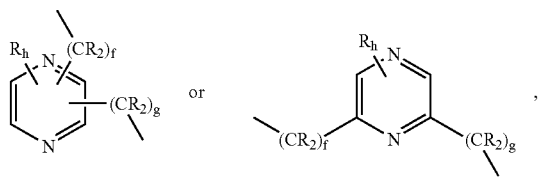

wherein $0 \leq h \leq 2$, wherein each R group is independently a hydrogen or is selected from the group Z defined above, $1 \leq f \leq 8$, $1 \leq g \leq 8$, and h and i are as indicated.

An arylene group is an aromatic group which is capable of being connected covalently to other substituents through at least two positions, including the following examples:

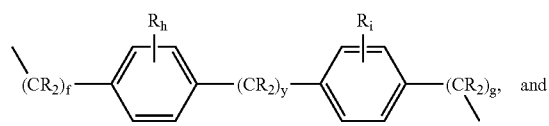

and

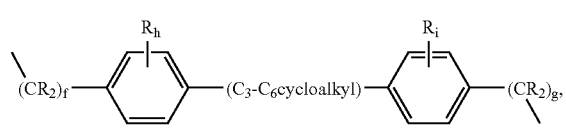

wherein each R group is independently a hydrogen or is selected from the group Z defined above, $1 \leq y \leq 10$ (for example, $1 \leq y \leq 4$), $1 \leq f \leq 8$, $1 \leq g \leq 8$, $0 \leq h \leq 4$, and $0 \leq i \leq 4$.

Heteroarylenedialkylene or heteroarylenedialkyl groups include those groups which have a heteroarylene group to which are bound two other alkylene groups, which may be the same or different, and which two alkylene groups are in turn bound to other moieties. Examples of heteroarylenedialkylene or heteroarylenedialkyl groups include the following:

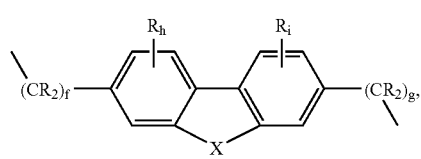

wherein $0 \leq h \leq 3$, and $0 \leq i \leq 3$, and X=NR' (wherein R' is hydrogen, a $C_1$-$C_5$ alkyl, $C_2$-$C_5$ alkenyl, $C_2$-$C_5$ alkynyl, or aryl group), O or S, $1 \leq f \leq 8$, $1 \leq g \leq 8$,

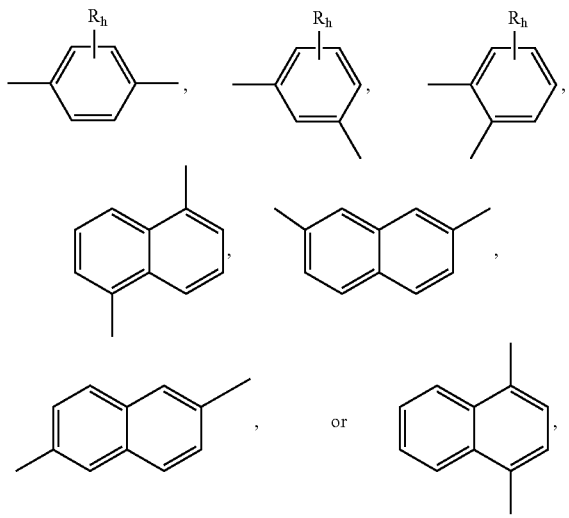

wherein each R group is independently a hydrogen or is selected from the group Z defined above, and $0 \leq h \leq 4$; for example:

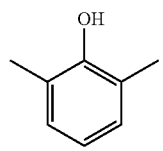

A heteroarylene group is a heteroaromatic group which is capable of being connected covalently to other substituents through at least two positions, including the following examples:

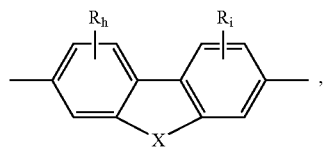

wherein $0 \leq h \leq 3$, and $0 \leq i \leq 3$, and X=NR' (wherein R' is hydrogen, a $C_1$-$C_5$ alkyl, $C_2$-$C_5$ alkenyl, $C_2$-$C_5$ alkynyl, or aryl group), O, or S,

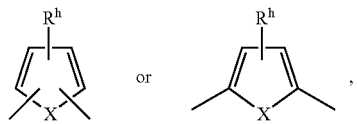

wherein $0 \leq h \leq 2$, and X=NR' (wherein R' is hydrogen, a $C_1$-$C_5$ alkyl, $C_2$-$C_5$ alkenyl, $C_2$-$C_5$ alkynyl, or aryl group), O, or S,

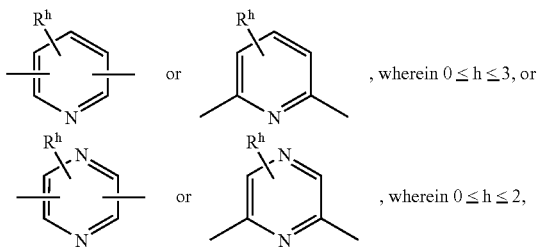

wherein each R group is independently a hydrogen or is selected from the group Z defined above, and h and i are as indicated; for example, the following groups:

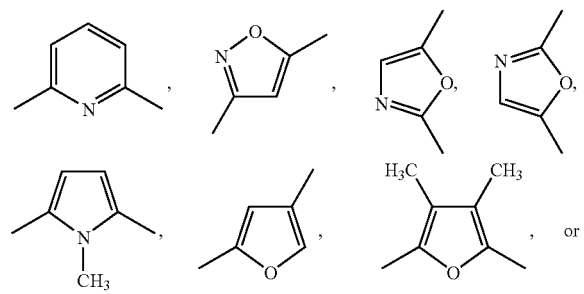

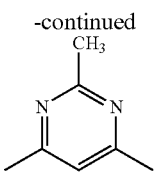

Likewise, the invention relates to the following heteroarylene groups

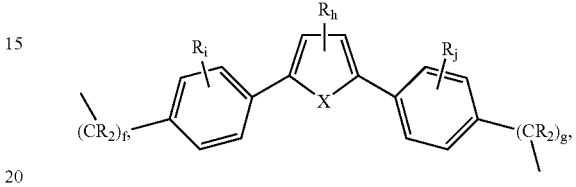

wherein X=NR' (wherein R' is hydrogen, a $C_1$-$C_5$ alkyl, $C_2$-$C_5$ alkenyl, $C_2$-$C_5$ alkynyl, or aryl group), O, or S; $0 \leq f \leq 8$, $0 \leq g \leq 8$; and each R group is independently a hydrogen or is selected from the group Z defined above.

In general, the term "aryl" includes groups, including 5- and 6-membered single-ring aromatic groups that may include from zero to four heteroatoms, for example, groups derived from benzene, pyrrole, furan, thiophene, thiazole, isothiaozole, imidazole, triazole, tetrazole, pyrazole, oxazole, isooxazole, pyridine, pyrazine, pyridazine, and pyrimidine, and the like.

Furthermore, the term "aryl" includes multicyclic aryl groups, e.g., groups derived from tricyclic, bicyclic, e.g., naphthalene, benzoxazole, benzodioxazole, benzothiazole, benzoimidazole, benzothiophene, methylenedioxyphenyl, quinoline, isoquinoline, napthyridine, indole, benzofuran, purine, benzofuran, deazapurine, or indolizine.

Those aryl groups having heteroatoms in the ring structure may also be referred to as "aryl heterocycles," "heterocycles," "heteroaryls" or "heteroaromatics".

An aromatic ring can be substituted at one or more ring positions with such substituents as described above, as for example, halogen, hydroxyl, alkyl (e.g. tolyl), alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Aryl groups can also be fused or bridged with alicyclic or heterocyclic rings which are not aromatic so as to form a polycycle (e.g., tetralin).

The term "heterocyclic" or "heterocycle" includes heteroaryls as well as any ring formed which incorporate a heteroatom or an atom which is not carbon. The ring may be saturated or unsaturated and may contain one or more double bonds. Examples of heterocyclic groups include pyridyl, furanyl, thiophenyl, morpholinyl, and indolyl groups. The term "heteroatom" includes atoms of any element other than carbon or hydrogen. Heteroatoms may be nitrogen, oxygen, sulfur and phosphorus.

An "arylene" group is a divalent moiety derived from an aryl group.

Examples of heterocycles include, but are not limited to, acridinyl; azocinyl; benzimidazolyl; benzofuranyl; benzothiofuranyl; benzothiophenyl; benzoxazolyl; benzthiazolyl; benztriazolyl; benztetrazolyl; benzisoxazolyl; benzisothiazolyl; benzimidazolinyl; carbazolyl; 4aH-carbazolyl; carbolinyl; chromanyl; chromenyl; cinnolinyl; decahydroquinolinyl; 2H,6H-1,5,2-dithiazinyl; dihydrofuro[2,3-b]tetrahydrofuran; furanyl; furazanyl; imidazolidinyl; imidazolinyl; imidazolyl; 1H-indazolyl; indolenyl; indolinyl; indolizinyl; indolyl; 3H-indolyl; isobenzofuranyl; isochromanyl; isoindazolyl; isoindolinyl; isoindolyl; isoquinolinyl; isothiazolyl; isoxazolyl; methylenedioxyphenyl; morpholinyl; naphthyridinyl; octahydroisoquinolinyl; oxadiazolyl; 1,2,3-oxadiazolyl; 1,2,4-oxadiazolyl; 1,2,5-oxadiazolyl; 1,3,4-oxadiazolyl; oxazolidinyl; oxazolyl; oxazolidinyl; pyrimidinyl; phenanthridinyl; phenanthrolinyl; phenazinyl; phenothiazinyl; phenoxathiinyl; phenoxazinyl; phthalazinyl; piperazinyl; piperidinyl; piperidonyl; 4-piperidonyl; piperonyl; pteridinyl; purinyl; pyranyl; pyrazinyl; pyrazolidinyl; pyrazolinyl; pyrazolyl; pyridazinyl; pyridooxazole; pyridoimidazole; pyridothiazole; pyridinyl; pyridyl; pyrimidinyl; pyrrolidinyl; pyrrolinyl; 2H-pyrrolyl; pyrrolyl; quinazolinyl; quinolinyl; 4H-quinolizinyl; quinoxalinyl; quinuclidinyl; tetrahydrofuranyl; tetrahydroisoquinolinyl; tetrahydroquinolinyl; tetrazolyl; 6H-1,2,5-thiadiazinyl; 1,2,3-thiadiazolyl; 1,2,4-thiadiazolyl; 1,2,5-thiadiazolyl; 1,3,4-thiadiazolyl; thianthrenyl; thiazolyl; thienyl; thienothiazolyl; thienooxazolyl; thienoimidazolyl; thiophenyl; triazinyl; 1,2,3-triazolyl; 1,2,4-triazolyl; 1,2,5-triazolyl; 1,3,4-triazolyl; and xanthenyl. Heterocycles include, but are not limited to, pyridinyl; furanyl; thienyl; pyrrolyl; pyrazolyl; pyrrolidinyl; imidazolyl; indolyl; benzimidazolyl; 1H-indazolyl; oxazolidinyl; benzotriazolyl; benzisoxazolyl; oxindolyl; benzoxazolinyl; and isatinoyl groups. Also included are fused ring and spiro compounds containing, for example, the above heterocycles.

An oligoethereal group, such as an oligo(alkyleneoxide) group, includes polyethyleneglycol (PEG) and short chain analogs thereof including $-[(CR_2)_sO]_t(CR_2)_s-$, wherein $1 \leq t \leq 6$ and $1 \leq s \leq 6$, and each R group is independently a hydrogen or is selected from the group Z defined above.

An arylene-di(oligoalkyleneoxide) group is an aryl group which has two oligoalkyleneoxide groups bound to it which in turn are bound to other moieties, and include the following examples:

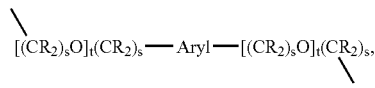

wherein "Aryl" is an arylene moiety, $1 \leq t \leq 6$, $0 \leq s \leq 6$, and each R group is independently a hydrogen or is selected from the group Z defined above. Example arylene-di(oligoalkyleneoxide) groups include:

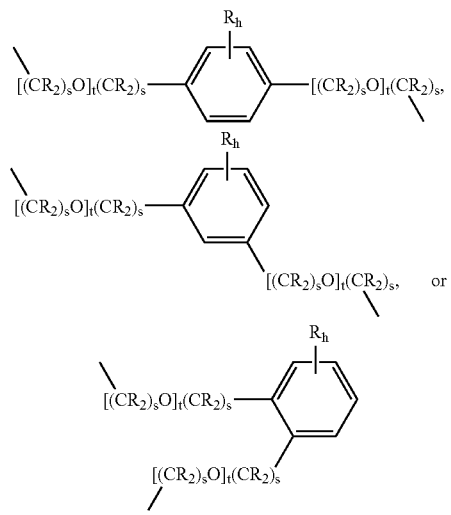

wherein $1 \leq t \leq 6$, $0 \leq s \leq 6$, $0 \leq h \leq 4$, and each R group is independently a hydrogen or is selected from the group Z defined above.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds.

In some embodiments, a "substituent" may be, selected from the group consisting of, for example, halogeno, trifluoromethyl, nitro, cyano, $C_1$-$C_6$ alkyl, $C_2$-$C_6$ alkenyl, $C_2$-$C_6$ alkynyl, $C_1$-$C_6$ alkylcarbonyloxy, arylcarbonyloxy, $C_1$-$C_6$ alkoxycarbonyloxy, aryloxycarbonyloxy, $C_1$-$C_6$ alkylcarbonyl, $C_1$-$C_6$ alkoxycarbonyl, $C_1$-$C_6$ alkoxy, $C_1$-$C_6$ alkylthio, arylthio, heterocyclyl, aralkyl, and aryl (including heteroaryl) groups.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds.

In some embodiments, a "substituent" may be, selected from the group consisting of, for example, halogeno, trifluoromethyl, nitro, cyano, $C_1$-$C_6$ alkyl, $C_2$-$C_6$ alkenyl, $C_2$-$C_6$ alkynyl, $C_1$-$C_6$ alkylcarbonyloxy, arylcarbonyloxy, $C_1$-$C_6$ alkoxycarbonyloxy, aryloxycarbonyloxy, $C_1$-$C_6$ alkylcarbonyl, $C_1$-$C_6$ alkoxycarbonyl, $C_1$-$C_6$ alkoxy, $C_1$-$C_6$ alkylthio, arylthio, heterocyclyl, aralkyl, and aryl (including heteroaryl) groups.

In some embodiments, the term "substituted" means that the moiety has substituents placed on the moiety other than hydrogen which allow the molecule to perform its intended function. Examples of substituents include moieties selected from straight or branched alkyl (for example, $C_1$-$C_5$), cycloalkyl (for example, $C_3$-$C_8$), alkoxy (for example, $C_1$-$C_6$), thioalkyl (for example, $C_1$-$C_6$), alkenyl (for example, $C_2$-$C_6$), alkynyl (for example, $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., $-NH_2$), $(CR'R'')_{0-3}CN$ (e.g., $-CN$), $NO_2$, halogen (e.g., F, Cl, Br, or I), $(CR'R'')_{0-3}C(halogen)_3$ (e.g., $-CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $-SO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g., $-OH$), $(CR'R'')_{0-3}COR'$, $(CR'R'')_{0-3}$(substituted or unsubstituted phenyl), $(CR'R'')_{0-3}(C_3$-$C_8$ cycloalkyl), $(CR'R'')_{0-3}CO_2R'$ (e.g., $-CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a $-(CH_2)_2O(CH_2)_2-$ group. For example, substitutions enhance the ability of the compounds of the invention to perform its intended function, e.g., inhibit formation of amyloid deposits. In some embodiments, a Z group may be a substituent as defined in this paragraph.

In one example group of compounds of the invention, m=1 and that n=0, 1, or 2. In compounds of Formula I, for example, p=0, 1, or 2, and q=1. Molecules according to Formula I may be symmetric, thus $R^{a1}=R^{a2}$, $R^{b1}=R^{b2}$, $R^{c1}=R^{c2}$, m=q, n=p, and $Y^1=Y^2$. Likewise, $R^1=R^2$ and $X^1=X^2$ are examples of molecules of Formula I.

One group of compounds of the invention are those of Formula Ia:

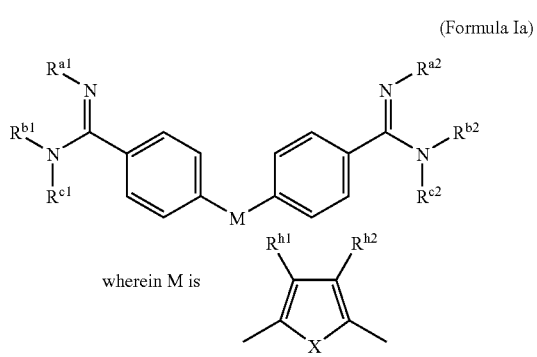

(Formula Ia)

wherein, in a one aspect, $R^{a1}$ and $R^{b1}$ together, or $R^{a2}$ and $R^{b2}$ together, represent a $C_2$ to $C_3$ alkylene; $R^{c1}$ and $R^{c2}$ are H; $R^{h1}$ is H; and $R^{h2}$ is $OCH_3$ or $O(C_6H_4)R$, wherein R is H or lower-alkyl, and X is O, NR' (wherein R' is hydrogen, a $C_1$-$C_5$ alkyl, $C_2$-$C_5$ alkenyl, $C_2$-$C_5$ alkynyl, or aryl group), or S.

In another group of compounds of Formula Ia, $R^{a1}$ and $R^{b1}$ together, or $R^{a2}$ and $R^{b2}$ together, represent a $C_2$ linear, saturated alkylene; $R^{c1}$ and $R^{c2}$ are -(lower alkyl)-OH; and $R^{h1}$ and $R^{h2}$ are each H. The "lower alkyl" group of $R^{c1}$ and $R^{c2}$ may be ethylene.

In yet another group of compounds of Formula Ia, $R^{a1}$ and $R^{b1}$ together, or $R^{a2}$ and $R^{b2}$ together, represent a $C_4$ alkylene; $R^{c1}$ and $R^{c2}$ are H, lower alkyl, cycloalkyl, aryl, hydroxyalkyl, aminoalkyl or alkylaminoalkyl; $R^{h1}$ and $R^{h2}$ are independently selected from the group consisting of H, lower alkyl, halogen, alkoxy, aryloxy, or arylalkoxy.

In still yet another group of compounds of Formula Ia, $R^{a1}$, $R^{a2}$, $R^{b1}$ and $R^{b2}$ are H; $R^{c1}$ and $R^{c2}$ are isopropyl or $-(CH_2)_3N(CH_3)_2$; and $R^{h1}$ and $R^{h2}$ are H.

In a further group of compounds of Formula Ia, $R^{a1}$ and $R^{b1}$ together, or $R^{a2}$ and $R^{b2}$ together, represent a phenylene group which is optionally substituted with up to three $-CONHR^dNR^eR^f$ groups where $R^d$ is lower alkyl and $R^e$ and $R^f$ are each independently selected from the group consisting of H or lower alkyl; and $R^{c1}$, $R^{c2}$, $R^{h1}$, and $R^{h2}$ are H.

An example compound of Formula Ia has $R^{h1}$, $R^{h2}$, $R^{b1}$, $R^{c1}$, $R^{b2}$, and $R^{c2}$ being H, and $R^{a1}$ and $R^{a2}$ groups being hydroxy or methoxy.

Another group of compounds are those of Formula Ib:

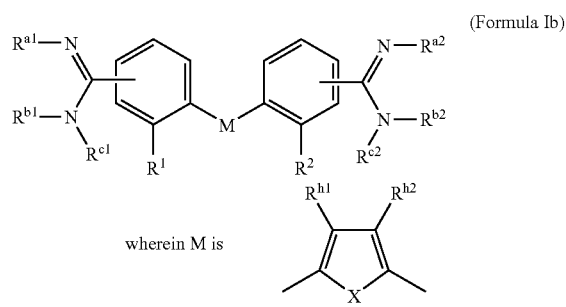

(Formula Ib)

wherein M is wherein X is O, NR' (wherein R' is hydrogen, a $C_1$-$C_5$ alkyl, $C_2$-$C_5$ alkenyl, $C_2$-$C_5$ $$ alkynyl, or aryl group), or S; $R^{h1}$ and $R^{h2}$ are each independently selected from the group consisting of H, loweralkyl, aryl, alkylaryl, aminoalkyl, aminoaryl, halogen, alkoxy, aryloxy, or oxyarylalkyl; $R^1$ and $R^2$ are each independently selected from the group consisting of H, loweralkyl, alkoxy, alkylaryl, aryl, aryloxy, aminoalkyl, aminoaryl, or halogen; and each $R^{a1}$, $R^{a2}$, $R^{b1}$, and $R^{b2}$ group is independently selected from the group consisting of H, loweralkyl, alkoxyalkyl, hydroxyalkyl, aminoalkyl, alkylaminoalkyl, cycloalkyl, aryl, hydroxy, or alkylaryl; or $R^{a1}$ and $R^{b1}$ together, or $R^{a2}$ and $R^{b2}$ together, represent $C_2$-$C_{10}$ alkyl, hydroxyalkyl, or alkylene; and each $R^{c1}$ and $R^{c2}$ group is independently H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl.

Another group of compounds are those of Formula Ic:

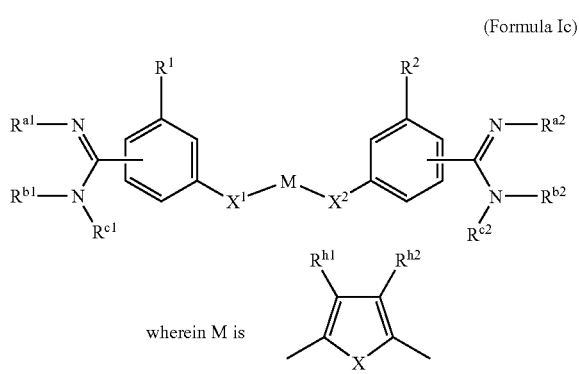
(Formula Ic)

wherein M is wherein X is S, O, or NR' (wherein R' is hydrogen, a $C_1$-$C_5$ alkyl, $C_2$-$C_5$ alkenyl, $C_2$-$C_5$ alkynyl, or aryl group); $R^{b1}$, $R^{b2}$, $R^{c1}$, and $R^{c2}$ are each independently selected from the group consisting of H, loweralkyl, alkoxy, alkoxyalkyl, cycloalkyl, aryl, hydroxyalkyl, aminoalkyl or alkylaminoalkyl; $R^1$ and $R^2$ are H, lower alkyl, alkoxy, alkoxyalkyl, hydroxyalkyl, cycloalkyl, aryl, aminoalkyl, alkylaminoalkyl or halogen; $R^{a1}$ and $R^{a2}$ are —OY, or $R^{a1}$ and $R^{b1}$ together, or $R^{a2}$ and $R^{b2}$ together represent

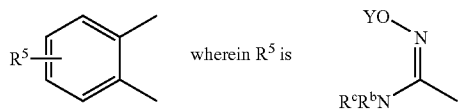
wherein $R^5$ is

Y is H or lower alkyl; each of $X^1$ and $X^2$ are —$(CH_2)_n$—, where n is an integer from 0 to 2; and $R^{h1}$ and $R^{h2}$ are each independently selected from the group consisting of H, lower alkyl, halogen, alkoxy, aryloxy, or oxyarylalkyl.

Yet another group of compounds are those of Formula Ic, wherein M is —$(CH_2)_n$— where n is an integer from 2 to 16 (or 2 to 12, or 2 to 10); each of $X^1$ and $X^2$ is O, NH, or S; $R^{a1}$, $R^{a2}$, $R^{b1}$, and $R^{b2}$ are H; or $R^{a1}$ and $R^{b1}$ together, or $R^{a2}$ and $R^{b2}$ together represent —$(CH_2)_m$—, wherein m is 2, 3, or 4; each of $R^1$ and $R^2$ are H, $OCH_3$, $NO_2$ or $NH_2$; $R^{c1}$ and $R^{c2}$ are H, $CH_3$ or $CH_2CH_3$. In another embodiment, when $X^1$ is O or S, both $R^1$ and $R^{c1}$ cannot be H; and when $X^2$ is O or S, both $R^2$ and $R^{c2}$ cannot be H.

Another group of compounds are those of Formula Id:

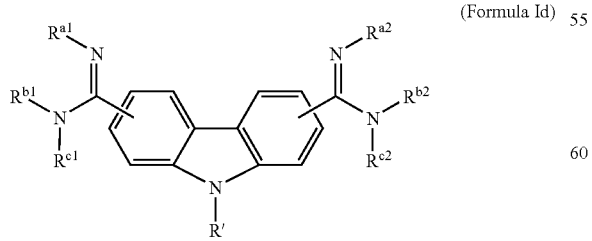
(Formula Id)

wherein each $R^{a1}$, $R^{a2}$, $R^{b1}$, and $R^{b2}$ are independently selected from the group consisting of H, loweralkyl, alkoxy- alkyl, hydroxyalkyl, aminoalkyl, alkylaminoalkyl, cycloalkyl, aryl, or alkylaryl; or two $R^{a1}$ and $R^{b1}$ together, or $R^{a2}$ and $R^{b2}$ together represent $C_2$-$C_{10}$ alkylene; $R^{c1}$ and $R^{c2}$ are independently H, hydroxy, loweralkyl, alkoxyalkyl, hydroxyalkyl, aminoalkyl, alkylaminoalkyl, cycloalkyl, aryl, or alkylaryl; and R' is H, loweralkyl, alkoxyalkyl, hydroxyalkyl, aminoalkyl, alkylaminoalkyl, cycloalkyl, aryl, or alkylaryl.

Another group of compounds are those of Formula Ie:

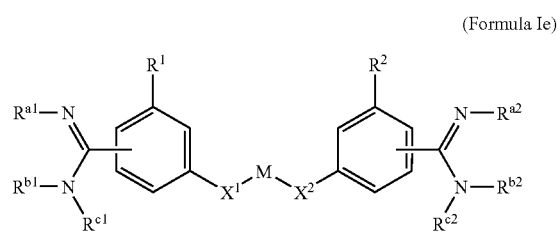
(Formula Ie)

wherein M is an alkylene group (e.g., $C_2$ to $C_{16}$), and $X^1$ and $X^2$ are oxygen.

In another group of compounds of Formula Ie, $R^{a1}$ and $R^{b1}$ together, or $R^{a2}$ and $R^{b2}$ together, represent a $C_2$ linear, saturated alkylene; $R^{c1}$ and $R^{c2}$ are H.

Another group of compounds of the invention are those of Formula IIa:

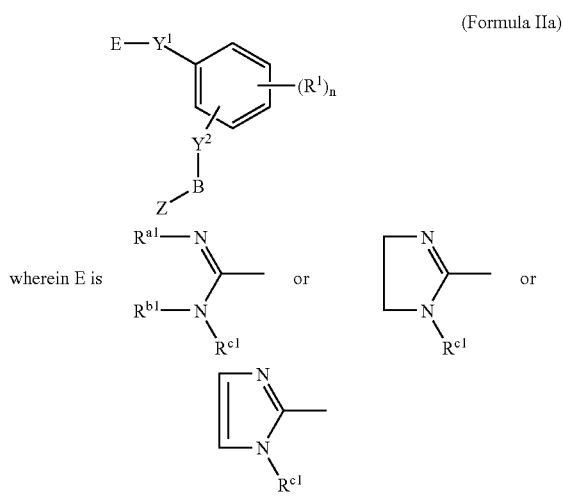
(Formula IIa)

wherein E is wherein $Y^1$, $Y^2$, Z, and $R^1$ are as defined above; n is 0-4; example $Y^2$ groups are O, NH, S, a substituted or unsubstituted methylene group, or a direct bond; Z may be a hydrogen atom, or Z may be alkyl, aryl, alkoxy, aryloxy, hydroxy, a substituted or unsubstituted amino, nitro, sulfo, or halogen group; $R^{a1}$, $R^{b1}$, and $R^{c1}$ are independently hydrogen, lower alkyl, aromatic, hydroxyl, or alkoxy; and B is a direct bond or a substituted or unsubstituted alkylene group containing from 1 to 16 carbon atoms, or a biphenylene group, or a combination biphenylene-alkylene group, the group —[(CH$_2$)$_n$O]$_m$(CH$_2$)$_n$— where m is 1 to 6 and n is 2 to 6, or a heterocyclic group.

Compounds of Formula IIb are also within the invention:

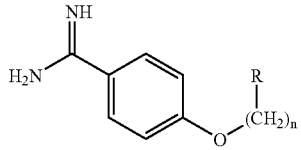
(Formula IIb)

wherein n=2, 3, 4, 5, 6, 7, 8, 9, or 10; and R=hydrogen, hydroxy, halogen, phenyl, biphenyl, naphthyl, alkoxy, carboxy, alkoxycarbonyl, aryloxycarbonyl, or aryloxy.

Another group of compounds are of Formula IIIa:

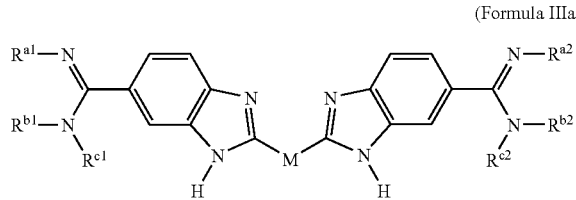
(Formula IIIa)

wherein M is

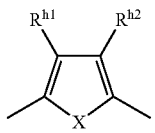

wherein X is S, O, or NR' (wherein R' is hydrogen, a C$_1$-C$_5$ alkyl, C$_2$-C$_5$ alkenyl, C$_2$-C$_5$ alkynyl, or aryl group); R$^{a1}$, R$^{a2}$, R$^{b1}$, and R$^{b2}$ are each independently selected from the group consisting of H, lower alkyl, alkoxyalkyl, cycloalkyl, aryl, alkylaryl, hydroxyalkyl, aminoalkyl, or alkylaminoalkyl; or R$^{a1}$ and R$^{b1}$ together, or R$^{a2}$ and R$^{b2}$ together represent a C$_2$ to C$_{10}$ alkyl, hydroxyalkyl, or alkylene; or R$^{a1}$ and R$^{b1}$ together, or R$^{a2}$ and R$^{b2}$ together are:

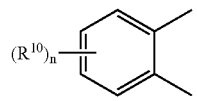

wherein n is a number from 1 to 3, and R$^{10}$ is H or —CONHR$^{11}$NR$^{15}$R$^{16}$, wherein R$^{11}$ is lower alkyl and R$^{15}$ and R$^{16}$ are each independently selected from the group consisting of H and lower alkyl; and R$^{c1}$ and R$^{c2}$ are H, hydroxy, lower alkyl, cycloalkyl, aryl, alkylaryl, alkoxyalkyl, hydroxycycloalkyl, alkoxycycloalkoxy, hydroxyalkyl, aminoalkyl or alkylaminoalkyl; and R$^{h1}$ and R$^{h2}$ are each independently selected from the group consisting of H, lower alkyl, halogen, aryl, arylalkyl, aminoalkyl, aminoaryl, alkoxy, aryloxy, or oxyarylalkyl.

Yet another group of compounds are of Formula IIIb:

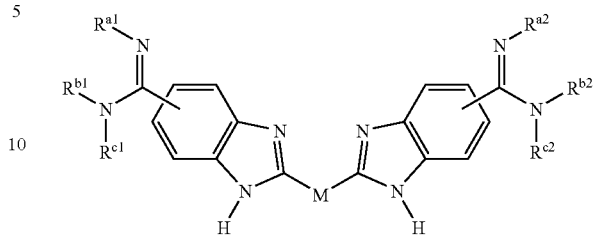
(Formula IIIb)

wherein each pair of R$^{a1}$ with R$^{b1}$ and R$^{a2}$ with R$^{b2}$ together represent —(CH$_2$)$_m$— wherein m is from two to four; R$^{c1}$ and R$^{c2}$ are independently H or loweralkyl; and M, which may be substituted with a lower alkyl group, is selected from the group consisting of —CH=CH—CH$_2$—CH$_2$—, —CH$_2$—CH=CH—CH$_2$—, and —CH=CH—CH=CH—.

Another group of compounds are those of Formula IIIc:

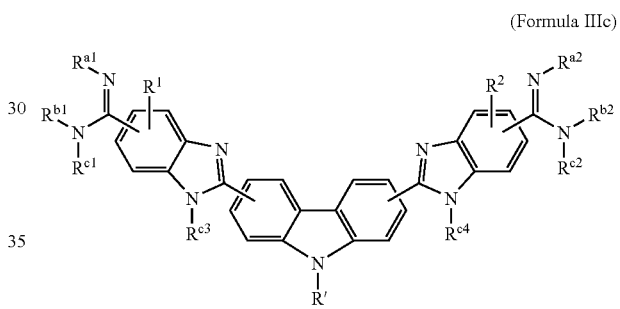
(Formula IIIc)

wherein R$^1$ and R$^2$ are independently H or —CONHR$^5$NR$^6$R$^7$, wherein R$^5$ is lower alkyl, R$^6$ and R$^7$ are each independently selected from the group consisting of H and lower alkyl; R$^{a1}$, R$^{a2}$, R$^{b1}$, and R$^{b2}$ are independently selected from the group consisting of H, lower alkyl, alkoxyalkyl, hydroxyalkyl, aminoalkyl, alkylaminoalkyl, cycloalkyl, aryl, or alkylaryl, or R$^{a1}$ and R$^{b1}$ together, or R$^{a2}$ and R$^{b2}$ together represent C$_2$-C$_{10}$ alkylene; R$^{c1}$ and R$^{c2}$ are independently H, hydroxy, lower alkyl, alkoxyalkyl, hydroxyalkyl, aminoalkyl, alkylaminoalkyl, cycloalkyl, aryl, or alkylaryl; R$^{c3}$ and R$^{c4}$ are independently H, hydroxy, loweralkyl, alkoxyalkyl, hydroxyalkyl, aminoalkyl, alkylaminoalkyl, cycloalkyl, aryl, or alkylaryl; and R' is H, loweralkyl, alkoxyalkyl, hydroxyalkyl, aminoalkyl, alkylaminoalkyl, cycloalkyl, aryl, alkylaryl, or halogen.

In another embodiment, the present invention relates to pharmaceutical compositions comprising compounds according to any of the Formulae herein for the treatment of an amyloid-related disease. The invention also pertains to the use of compounds in the manufacture of pharmaceutical compositions, as well as methods of manufacturing such pharmaceutical compositions. Such pharmaceutical compositions may be useful in the treatment or prevention of an amyloid-related disease.

The compositions of the invention may be supplied in a solution with an appropriate solvent or in a solvent-free form (e.g., lyophilized). In another aspect of the invention, the agents and buffers necessary for carrying out the methods of the invention may be packaged as a kit. The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The compositions of the invention may be administered therapeutically or prophylactically to treat diseases associated with amyloid-β fibril formation, aggregation, or deposition. The compositions of the invention may act to ameliorate the course of an amyloid-β related disease by a variety of mechanisms. In one embodiment, the pharmaceutical compositions disclosed herein prevent or inhibit amyloid protein assembly into insoluble fibrils which, in vivo, are deposited in various organs, or it favors plaque clearance or slows deposition in subjects already having deposits. In another embodiment, the pharmaceutical compositions may also prevent the amyloid protein, in its soluble, oligomeric form or in its fibrillar form, from binding or adhering to a cell surface and causing cell damage or toxicity. In yet another embodiment, the pharmaceutical compositions may block amyloid toxicity. In other embodiments, the compound may act by slowing the rate of amyloid-β fibril formation or deposition. In yet another embodiment, the compound may lessen the degree of amyloid-β deposition. Still other examples include inhibiting, reducing, or preventing amyloid-β fibril formation; inhibiting neurodegeneration or cellular toxicity induced by amyloid-β; inhibiting amyloid-β induced inflammation; or enhancing the clearance of amyloid-β from the brain brain or enhancing its degradation rate in the brain or in the peripheral organs.

The compounds of the invention can be formulated to ensure proper distribution in vivo. For example, the blood-brain barrier (BBB) excludes many highly hydrophilic compounds. To ensure that the more hydrophilic therapeutic compounds of the invention cross the BBB, they can be formulated, for example, in liposomes. For methods of manufacturing liposomes, see, e.g., U.S. Pat. Nos. 4,522, 811; 5,374,548; and 5,399,331. The liposomes may comprise one or more moieties which are selectively transported into specific cells or organs ("targeting moieties"), thus providing targeted drug delivery (see, e.g., V. V. Ranade (1989) J. Clin. Pharmacol. 29: 685).

Exemplary targeting moieties include folate or biotin (see, e.g., U.S. Pat. No. 5,416,016 to Low et al.); mannosides (Umezawa et al. (1988) Biochem. Biophys. Res. Commun. 153: 1038); antibodies (P. G. Bloeman et al. (1995) FEBS Lett. 357: 140; M. Owais et al. (1995) Antimicrob. Agents Chemother. 39: 180); surfactant protein A receptor (Briscoe et al. (1995) Am. J. Physiol. 1233: 134); gp120 (Schreier et al. (1994) J. Biol. Chem. 269: 9090); see also K. Keinanen; M. L. Laukkanen (1994) FEBS Lett. 346: 123; J. J. Killion; I. J. Fidler (1994) Immunomethods 4: 273. In an embodiment, the therapeutic compounds of the invention are formulated in liposomes; in another embodiment, the liposomes include a targeting moiety.

To ensure that compounds of the invention cross the BBB, they may be coupled to a BBB transport vector (for review of BBB transport vectors and mechanisms, see Bickel, et al., Adv. Drug Delivery Reviews, vol. 46, pp. 247-279, 2001). Exemplary transport vectors include cationized albumin or the OX26 monoclonal antibody to the transferrin receptor; these proteins undergo absorptive-mediated and receptor-mediated transcytosis through the BBB, respectively.

Examples of other BBB transport vectors that target receptor-mediated transport systems into the brain include factors such as insulin, insulin-like growth factors (IGF-I, IGF-II), angiotensin II, atrial and brain natriuretic peptide (ANP, BNP), interleukin I (IL-1) and transferrin. Monoclonal antibodies to the receptors which bind these factors may also be used as BBB transport vectors. BBB transport vectors targeting mechanisms for absorptive-mediated transcytosis include cationic moieties such as cationized LDL, albumin or horseradish peroxidase coupled with polylysine, cationized albumin or cationized immunoglobulins. Small basic oligopeptides such as the dynorphin analogue E-2078 and the ACTH analogue ebiratide can also cross the brain via absorptive-mediated transcytosis and are potential transport vectors.

Other BBB transport vectors target systems for transporting nutrients into the brain. Examples of such BBB transport vectors include hexose moieties, e.g. glucose, monocarboxylic acids, e.g. lactic acid, neutral amino acids, e.g. phenylalanine, amines, e.g. choline, basic amino acids, e.g. arginine, nucleosides, e.g. adenosine, purine bases, e.g. adenine, and thyroid hormone, e.g. triiodothyridine. Antibodies to the extracellular domain of nutrient transporters can also be used as transport vectors. Other possible vectors include angiotensin II and ANP, which may be involved in regulating BBB permeability.

In some cases, the bond linking the therapeutic compound to the transport vector may be cleaved following transport into the brain in order to liberate the biologically active compound. Exemplary linkers include disulfide bonds, ester-based linkages, thioether linkages, amide bonds, acid-labile linkages, and Schiff base linkages. Avidin/biotin linkers, in which avidin is covalently coupled to the BBB drug transport vector, may also be used. Avidin itself may be a drug transport vector.

To administer the therapeutic compound by other than parenteral administration, it may be necessary to coat the compound with, or co-administer the compound with, a material to prevent its inactivation. For example, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) J. Neuroimmunol. 7: 27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi.

The vehicle can be a solvent or dispersion medium containing, for example, water, ethanol, polyol (for example, glycerol, propylene glycol, and liquid polyethylene glycol, and the like), suitable mixtures thereof, and vegetable oils.

The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of amyloid deposition in subjects.

The present invention therefore includes pharmaceutical formulations comprising the compounds of the Formulae described herein, including pharmaceutically acceptable salts thereof, in pharmaceutically acceptable carriers for aerosol, oral and parenteral administration. Also, the present invention includes such compounds, or salts thereof, which have been lyophilized and which may be reconstituted to form pharmaceutically acceptable formulations for administration, as by intravenous, intramuscular, or subcutaneous injection. Administration may also be intradermal or transdermal.

In accordance with the present invention, a compound of the Formulae described herein, and pharmaceutically acceptable salts thereof, may be administered orally or through inhalation as a solid, or may be administered intramuscularly or intravenously as a solution, suspension or emulsion. Alternatively, the compounds or salts may also be administered by inhalation, intravenously or intramuscularly as a liposomal suspension.

Pharmaceutical formulations are also provided which are suitable for administration as an aerosol, by inhalation. These formulations comprise a solution or suspension of the desired compound of any Formula herein, or a salt thereof, or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid compound of any Formula described herein, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble compound of any Formula described herein, or a salt thereof, in a carrier which comprises water. A surfactant may be present which lowers the surface tension of the formulation sufficiently to result in the formation of droplets within the desired size range when subjected to nebulization.

Active compounds are administered at a therapeutically effective dosage sufficient to inhibit amyloid deposition in a subject. A "therapeutically effective" dosage preferably inhibits amyloid deposition by at least about 20%, or by at least about 40%, or even by at least about 60%, or by at least about 80% relative to untreated subjects. In the case of an Alzheimer's patient, a "therapeutically effective" dosage stabilizes cognitive function or prevents a further decrease in cognitive function (i.e., preventing, slowing, or stopping disease progression). The present invention accordingly provides therapeutic drugs. By "therapeutic" or "drug" is meant an agent having a beneficial ameliorative or prophylactic effect on a specific disease or condition in a living human or non-human animal.

Furthermore, active compounds are administered at a therapeutically effective dosage sufficient to decrease deposition in a subject of amyloid protein, e.g., Aβ40 or Aβ42. A therapeutically effective dosage inhibits amyloid deposition by, for example, at least about 15%, or by at least about 40%, or even by at least 60%, or at least by about 80% relative to untreated subjects.

In another embodiment, active compounds are administered at a therapeutically effective dosage sufficient to increase or enhance amyloid protein levels, e.g., Aβ40 or Aβ42, in the plasma or CSF of a subject. A therapeutically effective dosage increases the concentration by, for example, at least about 15%, or by at least about 40%, or even by at least 60%, or at least by about 80% relative to untreated subjects.

In another embodiment, active compounds are administered at a therapeutically effective dosage sufficient to decrease or reduce amyloid protein levels, e.g., Aβ40 or Aβ42, in the plasma or CSF of a subject. A therapeutically effective dosage decreases the concentration by, for example, at least about 15%, or by at least about 40%, or even by at least 60%, or at least by about 80% relative to untreated subjects.

In yet another embodiment, active compounds are administered at a therapeutically effective dosage sufficient to improve ADAS-cog (Alzheimer's Disease Assessment Scale-cognitive subscale) test scores by, e.g., at least about 1 point, at least about 2 points, at least about 3 points, at least about 4 points, at least about 5 points, at least about 10 points, at least about 12 points, at least about 15 points, or at least about 20 points relative to untreated subjects. (ADAS-cog; Rosen, et al., 1984, *Am. J. Psychiatry* 141: 1356-1364).

The ability of a compound to inhibit amyloid deposition can be evaluated in an animal model system that may be predictive of efficacy in inhibiting amyloid deposition in human diseases, such as a transgenic mouse expressing human APP or other relevant animal models where Aβ deposition is seen. Likewise, the ability of a compound to prevent or reduce cognitive impairment in a model system may be indicative of efficacy in humans. Alternatively, the ability of a compound can be evaluated by examining the ability of the compound to inhibit amyloid fibril formation in vitro, e.g., using a fibrillogenesis assay including a ThT, CD, or EM assay as described in, e.g., WO 2003/017,994. Also the binding of a compound to amyloid fibrils may be measured using a MS assay as described herein.

The present invention is also related to prodrugs of the compounds of the Formulae disclosed herein. Prodrugs are compounds which are converted in vivo to active forms (see, e.g., R. B. Silverman, 1992, "The Organic Chemistry of Drug Design and Drug Action," Academic Press, Chp. 8). Prodrugs can be used to alter the biodistribution (e.g., to allow compounds which would not typically enter the reactive site of the protease) or the pharmacokinetics for a particular compound. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound. The prodrug moieties may be metabolized in vivo by esterases or by other mechanisms to carboxylic acids.

Examples of prodrugs and their uses are well known in the art (See, e.g., Berge et al. (1977) "Pharmaceutical Salts", *J. Pharm. Sci.* 66: 1-19). The prodrugs can be prepared in situ during the final isolation and purification of the compounds, or by separately reacting the purified compound in its free acid form with a suitable derivatizing agent. Carboxylic acids can be converted into esters via treatment with an alcohol in the presence of a catalyst.

Examples of cleavable carboxylic acid prodrug moieties include substituted and unsubstituted, branched or unbranched lower alkyl ester moieties, (e.g., ethyl esters, propyl esters, butyl esters, pentyl esters, cyclopentyl esters, hexyl esters, cyclohexyl esters), lower alkenyl esters, dilower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, dilower alkyl amides, and hydroxy amides.

Certain embodiments of the present compounds can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed.

Representative salts include the hydrohalide (including hydrobromide and hydrochloride), sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, 2-hydroxyethylsulfonate, and laurylsulphonate salts and the like. (See, e.g., Berge et al. (1977) "Pharmaceutical Salts", *J. Pharm. Sci.* 66: 1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention.

These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Some selected compounds of the present invention are illustrated in Table 2, below. Although particular salts are depicted (such as the hydrochloride), the free base or non-salt form, as well as other pharmaceutically acceptable salts are within the present invention.

Those skilled in the art will recognize, or be able to ascertain using no more than routine experimentation, many equivalents to the specific embodiments and methods described herein. Such equivalents are intended to be encompassed by the scope of the following claims. All patents, patent applications, and literature references cited herein are hereby expressly incorporated by reference in their entirety. This invention is further illustrated by the following examples, which should not be construed as limiting.

EXAMPLES

The synthesis of amidine compounds of the invention is described in U.S. Pat. Nos. 5,428,051, 4,963,589, 5,202,320, 5,935,982, 5,521,189, 5,686,456, 5,627,184, 5,622,955, 5,606,058, 5,668,167, 5,667,975, 6,025,398, 6,214,883, 5,817,687, 5,792,782, 5,939,440, 6,017,941, 5,972,969, 6,046,226, 6,294,565 (B1), 6,156,779, 6,326,395, 6,008,247, 6,127,554, 6,172,104, 4,940,723, 5,206,236, 5,843,980, 4,933,347, 5,668,166, 5,817,686, 5,723,495, 4,619,942, 5,792,782, 5,639,755, 5,643,935, 5,602,172, 5,594,138, and 5,578,631. Additional synthesis protocols may be found in PCT Patent Application Publication No. WO 2003/017,994. Many of the compounds may also be purchased from Sigma-Aldrich Co. (Milwaukee, USA). The compounds may also be synthesized according to art-recognized techniques.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here. Functional and structural equivalents of the compounds described herein and which have the same general properties (e.g., functioning as anti-amyloid compounds), wherein one or more simple variations of substituents are made which do not adversely affect the essential nature or the utility of the compound.

The compounds of the present invention may be readily prepared in accordance with the synthesis schemes and protocols described herein, as illustrated in the specific procedures provided. However, those skilled in the art will recognize that other synthetic pathways for forming the compounds of this invention may be used, and that the following is provided merely by way of example, and is not limiting to the present invention. See, e.g., "Comprehensive Organic Transformations" by R. Larock, VCH Publishers (1989). It will be further recognized that various protecting and deprotecting strategies will be employed that are standard in the art (See, e.g., "Protective Groups in Organic Synthesis" by Greene and Wuts). Those skilled in the relevant arts will recognize that the selection of any particular protecting group (e.g., amine and carboxylprotecting groups) will depend on the stability of the protected moiety with regards to the subsequent reaction conditions and will understand the appropriate selections.

Further illustrating the knowledge of those skilled in the art is the following sampling of the extensive chemical literature: "Chemistry of the Amino Acids" by J. P. Greenstein and M. Winitz, John Wiley & Sons, Inc., New York (1961); "Comprehensive Organic Transformations" by R. Larock, VCH Publishers (1989); T. D. Ocain, et al., J. Med. Chem. 31, 2193-99 (1988); E. M. Gordon, et al., J. Med. Chem. 31, 2199-10 (1988); "Practice of Peptide Synthesis" by M. Bodansky and A. Bodanszky, Springer-Verlag, New York (1984); "Protective Groups in Organic Synthesis" by T. Greene and P. Wuts (1991); "Asymmetric Synthesis: Construction of Chiral Molecules Using Amino Acids" by G. M. Coppola and H. F. Schuster, John Wiley & Sons, Inc., New York (1987); "The Chemical Synthesis of Peptides" by J. Jones, Oxford University Press, New York (1991); and "Introduction of Peptide Chemistry" by P. D. Bailey, John Wiley & Sons, Inc., New York (1992).

Test compounds were purchased from commercial sources or synthesized and screened by mass spectroscopy ("MS") assay, which gives data on the ability of compounds to bind to an amyloid protein.

Samples were prepared as aqueous solutions containing 20% ethanol, 200 μM of a test compound and 20 μM of solubilized Aβ40. The pH value of each sample was adjusted to 7.4 (±0.2) by addition of 0.1% aqueous sodium hydroxide. The solutions were then analyzed by electrospray ionization mass spectroscopy using a Waters ZQ 4000 mass spectrometer. Samples were introduced by direct infusion at a flow-rate of 25 μL/min within 2 hr. after sample preparation. The source temperature was kept at 70° C. and the cone voltage was 20 V for all the analysis. Data were processed using Masslynx 3.5 software. The MS assay gives data on the ability of compounds to bind to Aβ, whereas the ThT, EM and CD assays give data on inhibition of fibrillogenesis.

Some selected compounds of the present invention are presented in Table 2 below. Although particular salts are depicted (such as the hydrochloride), the free base and other pharmaceutically acceptable salts, as well as the non-salt forms, are within the present invention.

TABLE 2

Structures and Activities of Some Compounds of the Invention in Soluble Aβ Assays

| Structure and Name | Code No. | MS Assay |
|---|---|---|
| 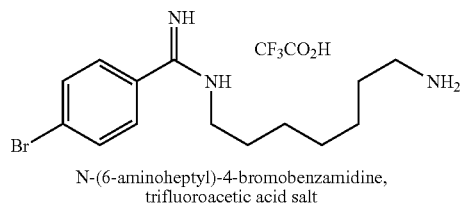 N-(6-aminoheptyl)-4-bromobenzamidine, trifluoroacetic acid salt | 145 | + |
| 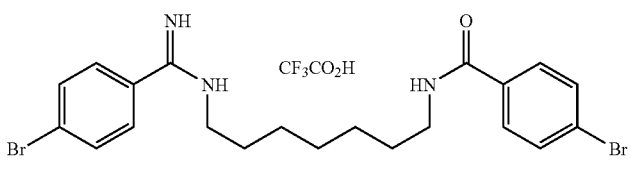 4-bromo-N-{7-[(4-bromobenzimidoyl)-amino]-heptyl}-benzamide, trifluoroacetic acid salt | 146 | + |

TABLE 2-continued

Structures and Activities of Some Compounds of
the Invention in Soluble Aβ Assays

| Structure and Name | Code No. | MS Assay |
|---|---|---|
| 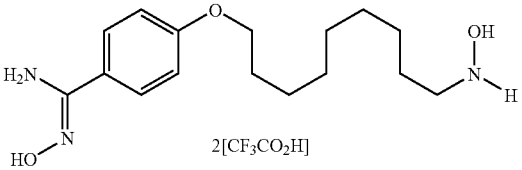 N-hydroxy-4-(9-hydroxyaminononyloxy)-benzamidine, trifluoroacetic acid salt | 147 | − |
| 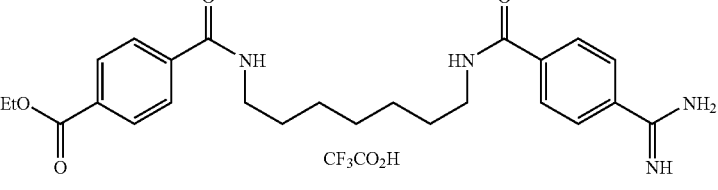 N-[7-(4-carbamimidoylbenzoylamino)-heptyl]-terephthalamic acid ethyl ester, trifluoroacetic acid salt | 148 | + |
| 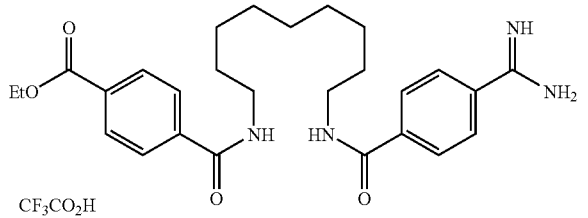 N-[9-(4-carbamimidoyl-benzoylamino)-nonyl]-terephthalamic acid ethyl ester, trifluoroacetic acid salt | 149 | + |
| 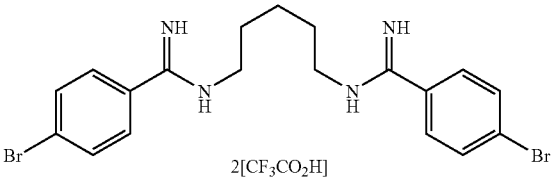 4,4'-(pentamethylenediamidino)di(p-bromobenzene), trifluoroacetic acid salt | 150 | + |
| 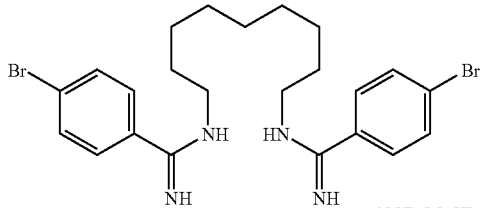 4,4'-(nonamethylenediamidino)di(p-bromobenzene), trifluoroacetic acid salt | 151 | + |

TABLE 2-continued

Structures and Activities of Some Compounds of the Invention in Soluble Aβ Assays

| Structure and Name | Code No. | MS Assay |
|---|---|---|
| 4,4'-(nonamethylenediamidino)di(p-methoxybenzene), trifluoroacetic acid salt | 152 | − |
| 4-methoxy-N-{2-[2-(4-methoxyphenyl)-4,5-dihydroimidazol-1-yl]-ethyl}-benzamidine, trifluoroacetic acid salt | 153 | + |
| 4,4'-(pentamethylenediamidino)di(p-methoxybenzene), hydrochloride salt | 154 | + |
| 2,2'-(p-amidinophenylcarboxamido)-N,N-diethyl-p-amidinobenzamide | 155 | − |
| {4-[5-(p-aminophenoxy)-pentyloxy]-phenyl}-(4,5-dihydro-1H-imidazol-2-yl)-amine, trifluoroacetic acid salt | 156 | − |

TABLE 2-continued

Structures and Activities of Some Compounds of the Invention in Soluble Aβ Assays

| Structure and Name | Code No. | MS Assay |
|---|---|---|
| 4,4'-(nonamethylenedisulfamyl)di(amidinobenzene), trifluoroacetic acid salt | 158 | – |
| 3,3'-(pentamethylenediaminocarbonyl)di(amidinobenzene), trifluoroacetic acid salt | 159 | nd |
| 4,4'-(tetramethylenediaminocarbonyl)di(amidinobenzene), trifluoroacetic acid salt | 160 | nd |

In each indicated assay, "+" = active; "–" = inactive; "nd" = not determined.

The present invention also relates to novel compounds and the synthesis thereof. Accordingly, the following examples are presented to illustrate how some of those compounds may be prepared.

General Aspects

Chemicals were purchased from Aldrich. The compounds were identified and characterized according to methods well known in the art, and the chemical structures depicted herein are consistent with those findings. Analytical thin-layer chromatography (TLC) was performed on silica gel 60 $F_{254}$ plastic-backed plates. Solvents were reagent grade unless otherwise specified. The $^1H$ (500 MHz) and $^{13}C$ (125 MHz) were recorded on a Varian Inova 500. The chemical shifts are reported on the δ scales in parts per million (ppm). The infra-red (IR) spectra were carried out on a Perkin-Elmer Spectra One spectrometer (neat compound on NaCl plate).

Preparation of the Starting Material for Compounds #145, #146, #150, and #151

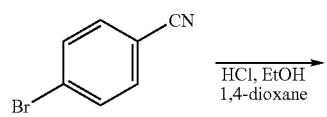

A cold solution (0° C.) of 4-bromobenzonitrile (1 g, 5.5 mmol) in ethanol (25 mL) was saturated with dry $HCl_{(g)}$. The mixture was then stirred at room temperature for 18 hours, after which FT-IR showed complete disappearance of the nitrile. The solution was concentrated to dryness, and further dried in vacuo. The ethyl 4-bromobenzimidate hydrochloride thus obtained was used in the synthesis of compounds 145, 146, 150, and 151.

Compound #145 and 146

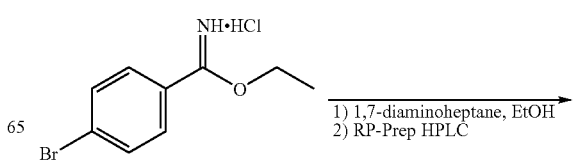

-continued

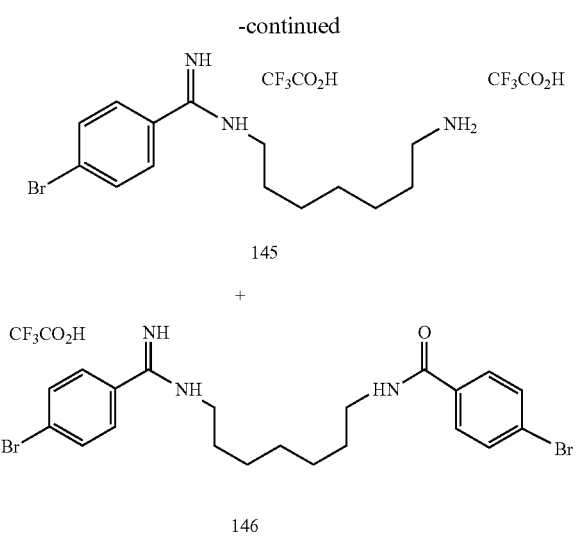

145

146

A solution of 1,7-diaminoheptane (257 mg, 1.97 mmol) in ethanol (10 mL) was added to a suspension of the ethyl 4-bromobenzimidate hydrochloride (1.21 g, 4.57 mmol) in ethanol (5 mL). The mixture was stirred at room temperature for 24 h. The mixture was concentrated to dryness. The crude products were separated by preparative RP-HPLC (Vydac C18, 215 nm, 50 mL/min, 0% to 90% MeCN in H$_2$O containing 0.1% TFA) to give compound # 145 as a waxy solid (29.2 mg, 0.054 mmol, 3% yield) and compound #146 as a waxy solid (18.7 mg, 0.031 mmol, 1.6% yield).

Compound #147

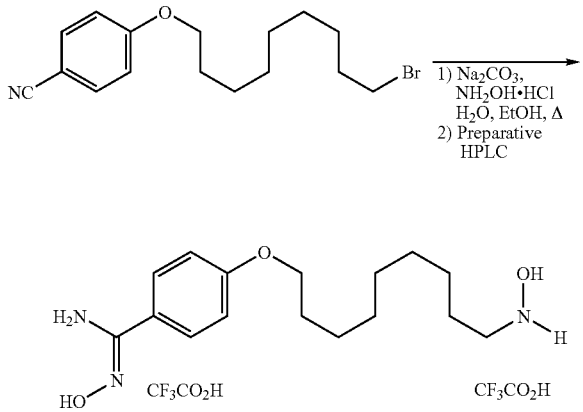

A mixture of 9-(4-cyanophenoxy)heptylbromide (181 mg, 0.5 mmol), sodium carbonate (180 mg, 1.7 mmol) and hydroxylamine hydrochloride (280 mg, 4 mmol) in 80% ethanol (10 mL) was heated at reflux for 2 h. The mixture was cooled to room temperature. A solid precipitated and was removed by filtration. The filtrate was concentrated to dryness under reduced pressure. The crude product was purified by preparative RP-HPLC (Vydac C18, 215 nm, 50 mL/min, 0% to 90% MeCN in H$_2$O containing 0.1% TFA) and lyophilized to give the title compound as a clear oil (48.8 mg, 0.091 mmol, 18% yield).

Compound #148

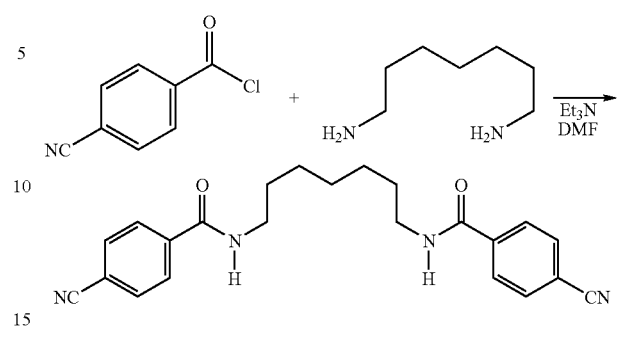

Step 1: To a cold solution (0° C.) of 1,7-diaminopentane (248 mg, 1.9 mmol) and triethylamine (0.65 mL, 4.6 mmol) in DMF (8 mL) was added 4-cyanobenzoyl chloride (685 mg, 4.1 mmol). The mixture was stirred overnight at room temperature, and then diluted with water. The beige solid that precipitated was collected by filtration and dried in vacuo, giving the corresponding amide (0.64 g, 1.65 mmol, 87% yield).

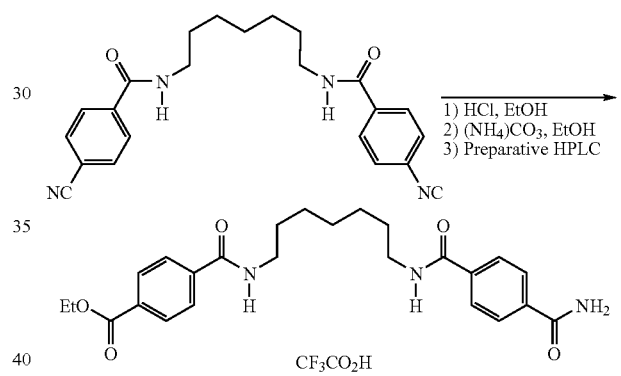

Step 2: A suspension of 1,7-bis-(4-cyanobenzamido)heptane (389 mg, 1 mmol) in a mixture of absolute ethanol (12 mL) and 1,4-dioxane (16 mL), was cooled to 0° C., saturated with dry HCl, and the resulting mixture was stirred for 4 days at room temperature. The solvent was evaporated under reduced pressure. A brownish solid was obtained. A mixture of the solid and ammonium carbonate (2 g, 20 mmol) in ethanol (25 mL) was stirred overnight at room temperature. Then, the mixture was filtered. The filtrate was concentrated to dryness. The crude product was purified by preparative RP-HPLC (Vydac C18, 215 nm, 50 mL/min, 0% to 90% MeCN in H$_2$O containing 0.1% TFA) and lyophilized to give the title compound as a white solid (79.9 mg, 0.141 mmol, 14% yield).

Compound #149

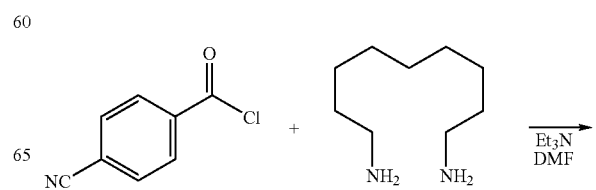

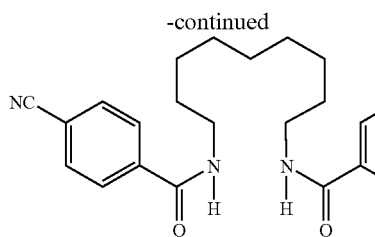

Step 1: To a cold solution (0° C.) of 1,9-diaminononane (296 mg, 1.9 mmol) and triethylamine (0.65 mL, 4.6 mmol) in DMF (8 mL) was added 4-cyanobenzoyl chloride (685 mg, 4.1 mmol). The mixture was stirred overnight at room temperature, and then diluted with water. The beige solid that precipitated was collected by filtration and dried in vacuo, giving the corresponding amide (0.64 g, 1.54 mmol, 81% yield).

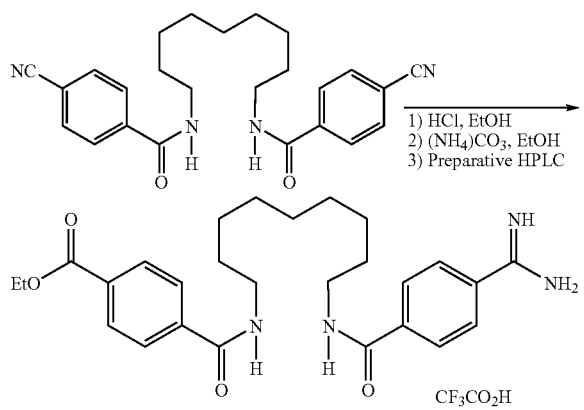

Step 2: A suspension of 1,9-bis-(4-cyanobenzamido) nonane (417 mg, 1 mmol), in a mixture of absolute ethanol (12 mL) and 1,4-dioxane (16 mL), was cooled to 0° C., saturated with dry HCl, and the resulting mixture was stirred for 4 days at room temperature. The solvent was evaporated under reduced pressure. A brownish solid was obtained. A mixture of the solid and ammonium carbonate (2 g, 20 mmol) in ethanol (25 mL) was stirred overnight at room temperature. Then, the mixture was filtered. The filtrate was concentrated to dryness. The crude product was purified by preparative RP-HPLC (Vydac C18, 215 nm, 50 mL/min, 0% to 90% MeCN in H$_2$O containing 0.1% TFA) and lyophilized to give the title compound as a white solid (96.5 mg, 0.132 mmol, 16% yield).

Compound #150

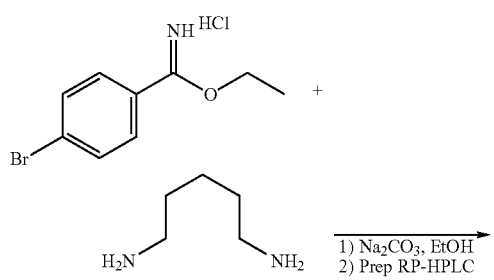

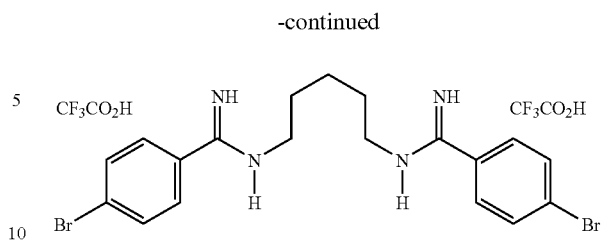

Sodium carbonate (1.3 g) was loaded into a dry 25 mL round bottom flask. The 1,5-diaminopentane (0.65 mmol, 0.077 mL) was added, followed by the ethyl 4-bromobenzimidate hydrochloride (465 mg, 1.7 mmol) and finally the ethanol (10 mL). The mixture was stirred vigorously at room temperature for 22 hours then filtered to remove solids. The solids were washed with methanol (20 mL). The filtrate was concentrated to dryness under reduced pressure. The crude product was purified by preparative RP-HPLC (Vydac C18, 215 nm, 50 mL/min, 0% to 90% MeCN in H$_2$O containing 0.1% TFA) and lyophilized to give the title compound as a white solid (246.6 mg, 0.355 mmol, 54% yield).

Compound #151

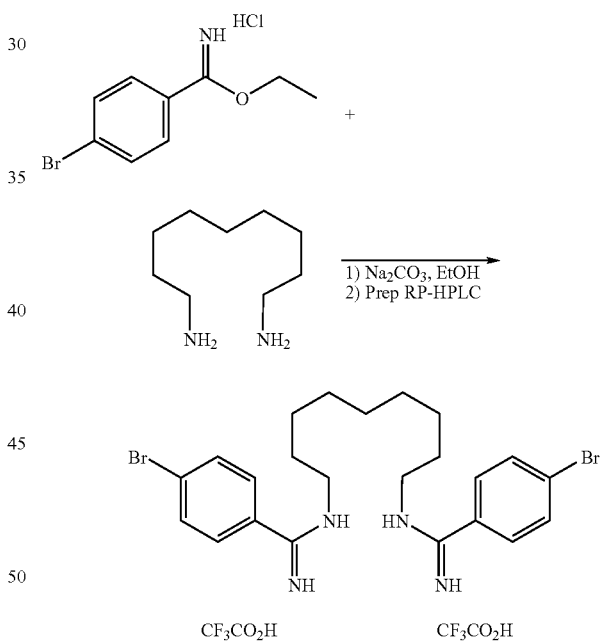

Sodium carbonate (1.3 g) was loaded into a dry 25 mL round bottom flask. The 1,9-diaminononatane (0.68 mmol, 108 mg) was added, followed by ethyl 4-bromobenzimidate hydrochloride (500 mg, 1.89 mmol) and finally the ethanol (14 mL). The mixture was stirred vigorously at room temperature for 22 hours then filtered to remove solids. The solids were washed with methanol (20 mL). The filtrate was concentrated to dryness under reduced pressure. The crude product was purified by preparative RP-HPLC (Vydac C18, 215 nm, 50 mL/min, 0% to 90% MeCN in H$_2$O containing 0.1% TFA) and lyophilized to give the title compound as a white solid (231.3 mg, 0.308 mmol, 47% yield).

Preparation of the Starting Material for Compounds #152, #153, and # 154

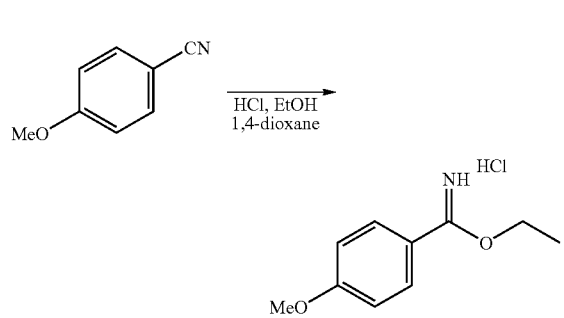

A cold solution (0° C.) of 4-methoxybenzonitrile (1.29 g, 9.59 mmol) in ethanol (30 mL) was saturated with dry $HCl_{(g)}$. The mixture was then stirred at room temperature for 2 days, after which FT-IR showed complete disappearance of the nitrile. The solution was concentrated to dryness, and further dried in vacuo. The ethyl 4-methoxybenzimidate hydrochloride thus obtained was used in the synthesis of compounds 152, 153 and 154.

Compound # 152

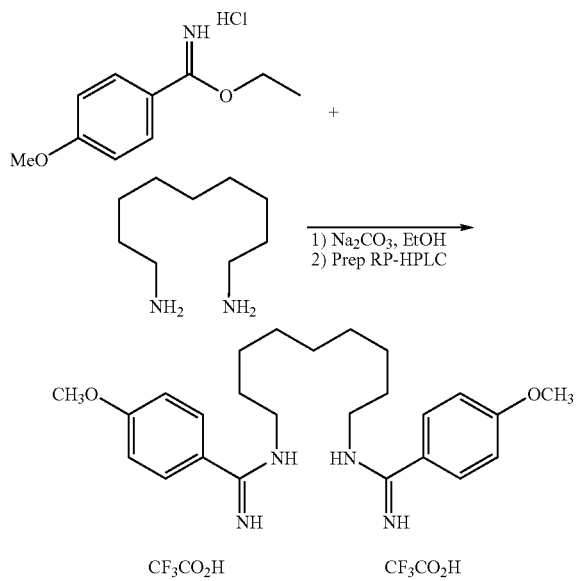

Sodium carbonate (1.50 g) was loaded into a dry 25 mL round bottom flask. The 1,7-diaminoheptane (1 mmol, 159 mg) was added, followed by the ethyl 4-methoxybenzimidate hydrochloride (550 mg, 2.50 mmol) and finally the ethanol (10 mL). The mixture was stirred vigorously at room temperature for a day, and then solids were removed by filtration. The solids were washed with methanol (20 mL). The filtrate was concentrated to dryness under reduced pressure. The crude product was purified by preparative RP-HPLC (Vydac C18, 215 nm, 50 mL/min, 0% to 90% MeCN in $H_2O$ containing 0.1% TFA) and lyophilized to give the title compound as a white solid (249.3 mg, 0.382 mmol, 38% yield).

Compound # 153

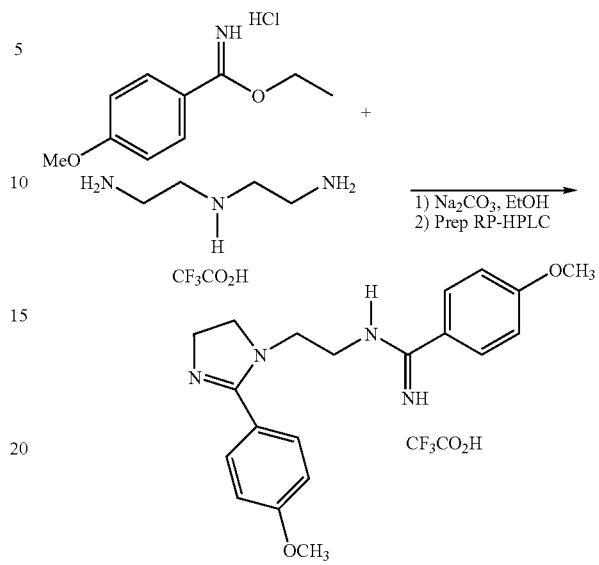

Sodium carbonate (1.45 g) was loaded into a dry 25 mL round bottom flask. The diethylenetriamine (1 mmol, 0.090 mL) was added, followed by the ethyl 4-methoxybenzimidate hydrochloride (430 mg, 2.0 mmol) and finally the ethanol (10 mL). The mixture was stirred vigorously at room temperature for a day, and then solids were removed by filtration. The solids were washed with methanol (20 mL). The filtrate was concentrated to dryness under reduced pressure. The crude product was purified by preparative RP-HPLC (Vydac C18, 215 nm, 50 mL/min, 0% to 90% MeCN in $H_2O$ containing 0.1% TFA) and lyophilized to give the title compound as a white solid (177.4 mg, 0.306 mmol, 31% yield).

Compound #154

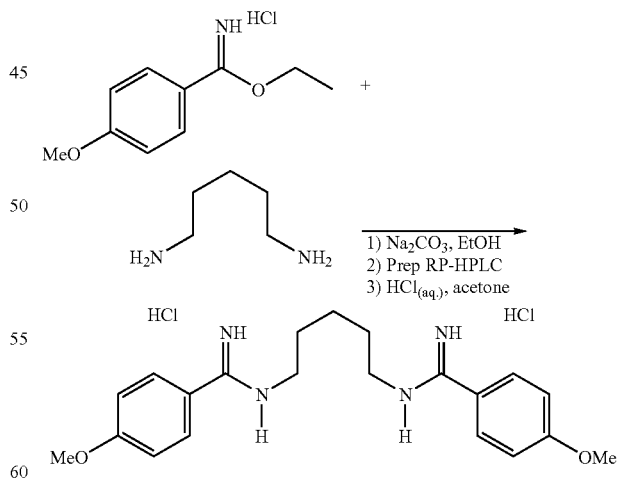

Sodium carbonate (1.45 g) was loaded into a dry 25 mL round bottom flask. The 1,5-diaminopentane (0.84 mmol, 0.10 mL) was added, followed by the ethyl 4-methoxybenzimidate hydrochloride (400 mg, 2.23 mmol) and finally the ethanol (10 mL). The mixture was stirred vigorously at room temperature for a day, and then solids were removed by filtration. The solids were washed with methanol (20 mL). The filtrate was concentrated to dryness under reduced pressure. The crude product was purified by preparative RP-HPLC (Vydac C18, 215 nm, 50 mL/min, 0% to 90% MeCN in H$_2$O containing 0.1% TFA). It still contained traces of impurities after two purifications by preparative HPLC. The Product was recrystallized from 0.5 mL of 2 N HCl in acetone (4.5 mL). The crystals slowly formed at −20° C. The crystals were collected by filtration, rinsed with acetone and dried in vacuo. The title compound was obtained as a white solid (37.6 mg, 0.085 mmol, 10% yield).

Compound #155

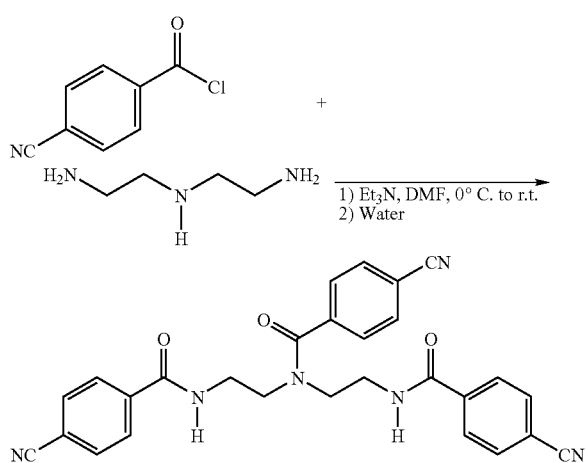

Step 1: To a cold solution (0° C.) of diethylenetriamine (0.110 mL, 1.0 mmol) and triethylamine (0.41 mL, 3.0 mmol) in DMF (5.5 mL) was added 4-cyanobenzoyl chloride (365 mg, 2.2 mmol). The mixture was stirred overnight for 4 hours, and then diluted with water (40 mL). The aqueous layer was extracted with ethyl acetate (4×25 mL).

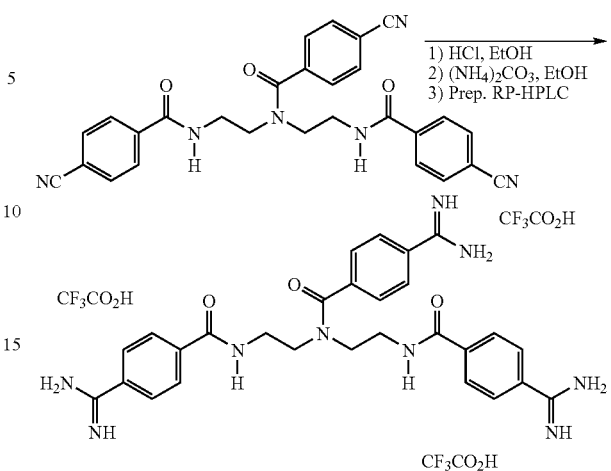

Step 2: A suspension of the crude tris-nitrile (296.7 mg, 0.605 mmol) in a mixture of absolute ethanol (10 mL) and 1,4-dioxane (5 mL), was cooled to 0° C., saturated with dry HCl, and the resulting mixture was stirred for one day at room temperature. The volume of the solution was reduced to about 4 mL and ether was added. The crude amidate was collected by filtration and dried in vacuo. A mixture of the solid and ammonium carbonate (1.20 g, 12.0 mmol) in ethanol (10 mL) was stirred overnight at room temperature. The mixture was filtered, then the filtrate was concentrated to dryness. The crude product was purified by preparative RP-HPLC (Vydac C18, 215 nm, 50 mL/min, 0% to 90% MeCN in H$_2$O containing 0.1% TFA). A white solid formed upon concentration of the preparative HPLC fractions. The solid was collected by filtration and dried in vacuo. The title compound was obtained as a white solid (129.1 mg, 0.146 mmol, 24% yield).

Compound #156

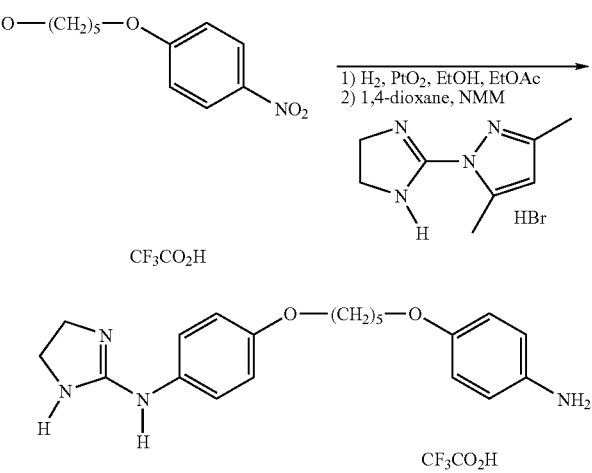

The combined organic layers were washed with water (2×10 mL), brine (1×15 mL) then dried over magnesium sulfate. The solvent was evaporated under reduced pressure and the residue was dried in-vacuo to give the compound as a tan solid (296.7 mg, 0.605 mmol, 61% yield).

The 1,5-bis(4-nitrophenoxy)pentane (176 mg, 0.508 mmol) was reduced under H$_2$ (55 psi) with platinum (W) oxide (14 mg) in a mixture of ethanol (3 mL) and ethyl acetate (3 mL) for 4 hours. The mixture was filtered over Celite and the pad was washed with methanol (5 mL). The filtrate was concentrated to dryness under reduced pressure and the residue was dried in vacuo for 30 minutes. The residue was then dissolved in a mixture of 1,4-dioxane (5 mL) and dichloromethane (1.5 mL). N-Methylmorpholine (0.13 mL, 1.13 mmol) was added, followed by the 1-(4,5-dihydro-1H-imidazol-2-yl)-3,5-dimethyl-1H-pyrazole hydrobromide (270 mg, 1.08 mmol). The suspension was stirred for a day at room temperature. Dichloromethane was evaporated and the mixture was heated by an oil bath at 60° C. for 2 days. The reaction was monitored by mass spectrometry. The solids were removed by filtration and the filtrate was acidified with 2 N HCl (2 mL) then concentrated to dryness under reduced pressure. The crude product was purified by preparative RP-HPLC (Vydac C18, 215 nm, 50 mL/min, 0% to 90% MeCN in H₂O containing 0.1% TFA). The title compound was isolated as an oil (25.1 mg, 0.043 mmol, 8.5% yield).

Compound #158

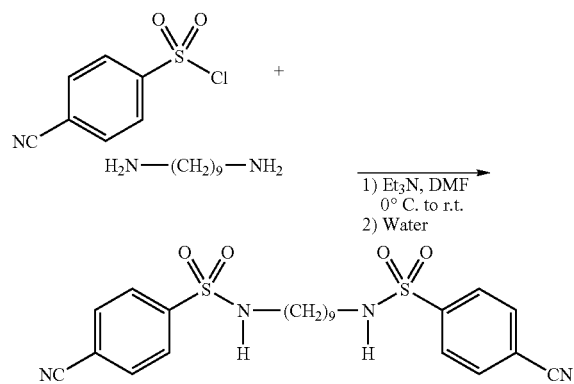

Step 1: To a cold solution (0° C.) of 1,9-diaminononane (480 mg, 3.0 mmol) and triethylamine (2.05 mL, 14.5 mmol) in DMF (9.0 mL) was added 4-cyanobenzenesulfonyl chloride (1.25 g, 6.3 mmol). The mixture was stirred overnight for 4 hours, and then diluted with water (40 mL). The beige solid that precipitated was collected by filtration and dried in vacuo, giving the corresponding sulfonamide (1.28 g, 2.62 mmol, 87% yield).

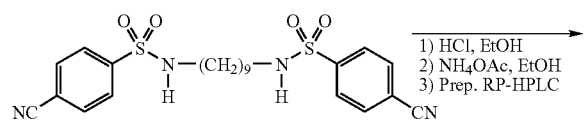

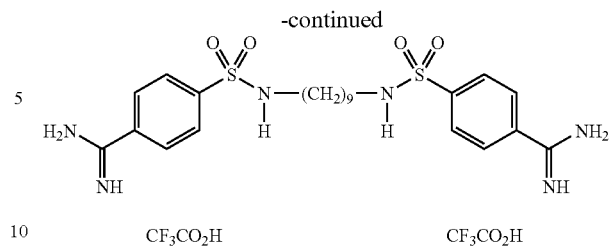

Step 2: A suspension of 1,9-bis(4-cyanobenzesulfonamidoamido)nonane (318 mg, 0.651 mmol), in a mixture of absolute ethanol (10.0 mL) and 1,4-dioxane (4.0 mL), was cooled to 0° C., saturated with dry HCl, and the resulting mixture was stirred 24 hours at room temperature. The solvent was evaporated under reduced pressure. A tan solid was obtained. A mixture of the solid and ammonium acetate (1.05 g, 13.6 mmol) in ethanol (10 mL) was stirred 24 hours at room temperature. The mixture had turned to a gel. Addition of methanol (10 mL) produced a solution. The addition of concentrated HCl (1.5 mL) precipitated some of the ammonium chloride. The mixture was filtered, then filtrate was concentrated to dryness and dried in vacuo. The crude product was purified by preparative RP-HPLC (Vydac C18, 215 nm, 50 mL/min, 0% to 90% MeCN in H₂O containing 0.1% TFA) and lyophilized to give the title compound as a white solid (205.2 mg, 0.273 mmol, 42% yield).

Compound # 159

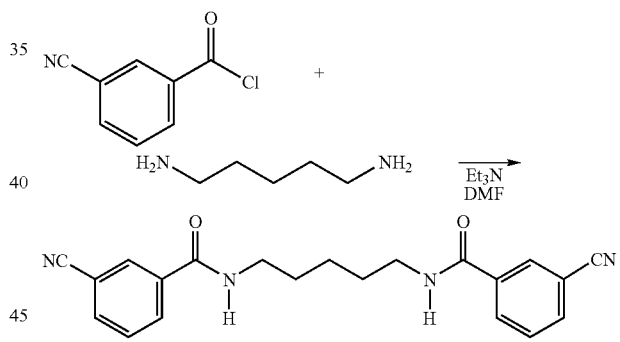

Step 1: To a cold solution (0° C.) of 1,5-diaminopentane (0.35 mL, 3 mmol) and triethylamine (0.49 mL, 3.5 mmol) in DMF (6 mL) was added 3-cyanobenzoyl chloride (550 mg, 3.3 mmol). The mixture was stirred overnight at room temperature, and then diluted with water (40 mL). The beige solid that precipitated was collected by filtration and dried in vacuo, giving the corresponding amide, 500 mg, 1.39 mmol, 90% yield.

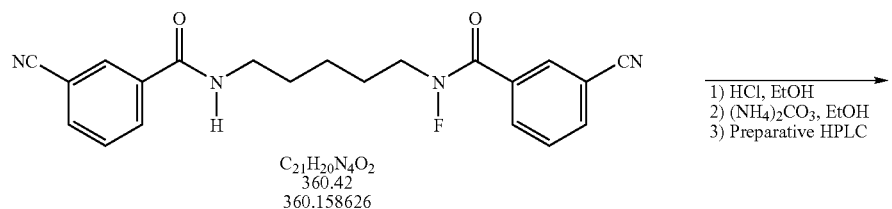

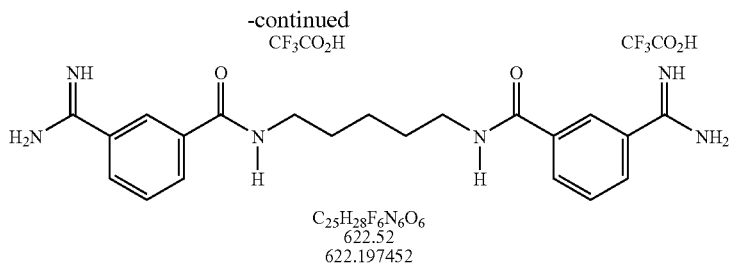

$C_{25}H_{28}F_6N_6O_6$
622.52
622.197452

Step 2: A suspension of 1,5-bis-(3-cyanobenzamido)pentane (480 mg, 1.33 mmol), in a mixture of absolute ethanol (10 mL) and 1,4-dioxane (10 mL), was cooled to 0° C., saturated with dry HCl, and the resulting mixture was stirred for a days at room temperature. The solvent was evaporated under reduced pressure. A brownish solid was obtained. A mixture of the solid and ammonium carbonate (2.55 g, 20 mmol) and 4 Å molecular sieves (175 mg) in ethanol (20 mL) was stirred overnight at room temperature. Then, the mixture was filtered, the solids were rinsed with methanol (2×10 mL). TFA (1.5 mL) was added and the filtrate was concentrated to dryness. The crude product was purified by preparative RP-HPLC (Vydac C18, 215 nm, 50 mL/min, 0% to 90% MeCN in $H_2O$ containing 0.1% TFA) and lyophilized to give the title compound as a white solid, 180.2 mg, 0.289 mmol, 25% yield.

Compound # 160

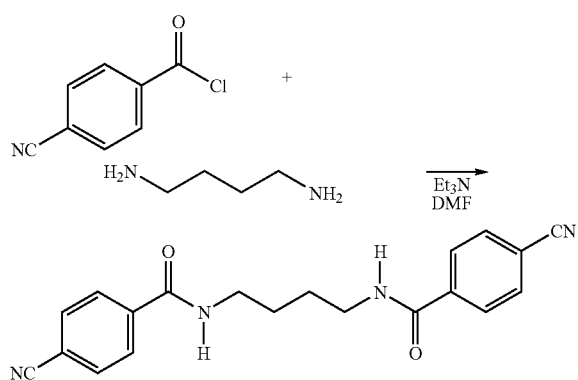

Step 1: To a cold solution (0° C.) of 1,4-diaminobutane (0.3 mL, 3 mmol) and triethylamine (0.49 mL, 3.5 mmol) in DMF (9 mL) was added 4-cyanobenzoyl chloride (550 mg, 3.3 mmol). The mixture was stirred overnight at room temperature, and then diluted with water (20 mL). The beige solid that precipitated was collected by filtration and dried in vacuo, giving the corresponding amide, 0.48 g, 1.39 mmol, 90% yield.

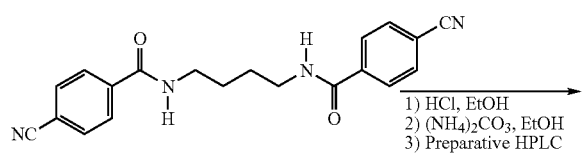

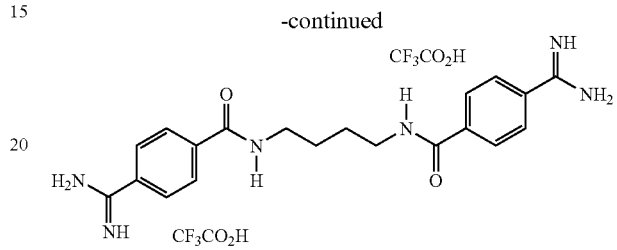

Step 2: A suspension of 1,4-bis-(4-cyanobenzamido)butane (460 mg, 1.33 mmol), in a mixture of absolute ethanol (10 mL) and 1,4-dioxane (10 mL), was cooled to 0° C., saturated with dry HCl, and the resulting mixture was stirred for a week at room temperature with 3 saturation with HCl. The solvent was evaporated under reduced pressure. A brownish solid was obtained. A mixture of the solid and ammonium carbonate (2.55 g, 20 mmol) and 4 Å molecular sieves (175 mg) in ethanol (20 mL) was stirred overnight at room temperature. Then, the mixture was concentrated to dryness. The crude product was re-suspended in water and the suspension centrifuged. The supernatant was purified by preparative RP-HPLC (Vydac C18, 215 nm, 50 mL/min, 0% to 90% MeCN in $H_2O$ containing 0.1% TFA) and lyophilized to give the title compound as a white solid, 191 mg, 0.307 mmol, 23% yield.

The invention claimed is:

1. A method of treating a disease selected from the group consisting of Alzheimer's disease, Down's syndrome, Mild Cognitive Impairment, age-related macular degeneration, and cerebral amyloid angiopathy in a subject in need thereof comprising administering to a subject a therapeutically effective amount of a compound, wherein said compound is selected from the group consisting of N-(6-aminoheptyl)-4-bromobenzamidine (compound #145),
4-bromo-N-{7-[(4-bromobenzimidoyl)-amino]-heptyl}-benzamide (compound #146),
N-hydroxy-4-(9-hydroxyaminononyloxy)-benzamidine (compound #147),
N-[7-(4-carbamimidoylbenzoylamino)-heptyl]-terephthalamic acid ethyl ester (compound #148),
N-[9-(4-carbamimidoyl-benzoylamino)-nonyl]-terephthalamic acid ethyl ester (compound #149),
4,4'-(pentamethylenediamidino)di(p-bromobenzene) (compound #150),
4,4'-(nonamethylenediamidino)di(p-bromobenzene) (compound #151),
4,4'-(nonamethylenediamidino)di(p-methoxybenzene) (compound #152),
4-methoxy-N-{2-[2-(4-methoxyphenyl)-4,5-dihydroimidazol-1-yl]-ethyl}-benzamidine (compound #153), 4,4'-(pentamethylenediamidino)di(p-methoxybenzene) (compound #154), 2,2'-(p-amidinophenylcarboxamido)-N,N-diethyl-p-amidinobenzamide (compound #155), {4-[5-(p-aminophenoxy)-pentyloxy]-phenyl}-(4,5-dihydro-1H-imidazol-2-yl)-amine (compound #156), 4,4'-(nonamethylenedisulfamyl)di(amidinobenzene) (compound #158), 3,3'-(pentamethylenediaminocarbonyl)di(amidinobenzene) (compound #159), 4,4'-(tetramethylenediaminocarbonyl)di(amidinobenzene) (compound #160), and pharmaceutically acceptable salts thereof.

2. The method according to claim 1, wherein said compound is adapted to be administered orally.

3. The method according to claim 1, where said subject is a human.

4. A chemical compound selected from the group consisting of:

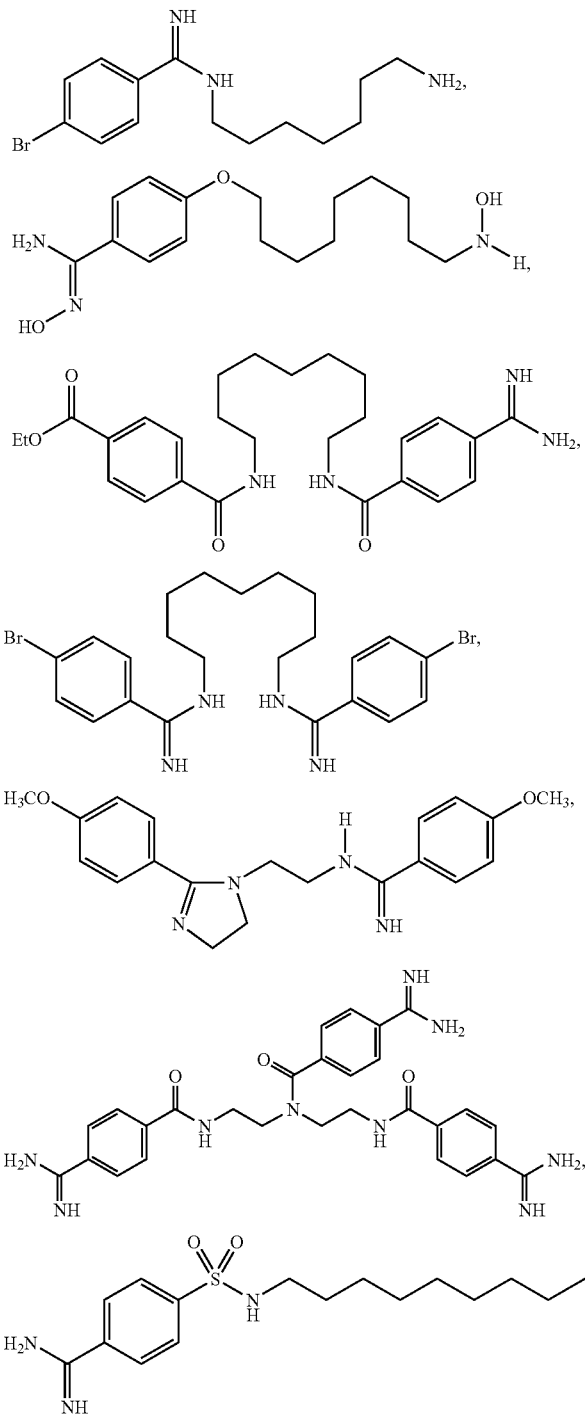
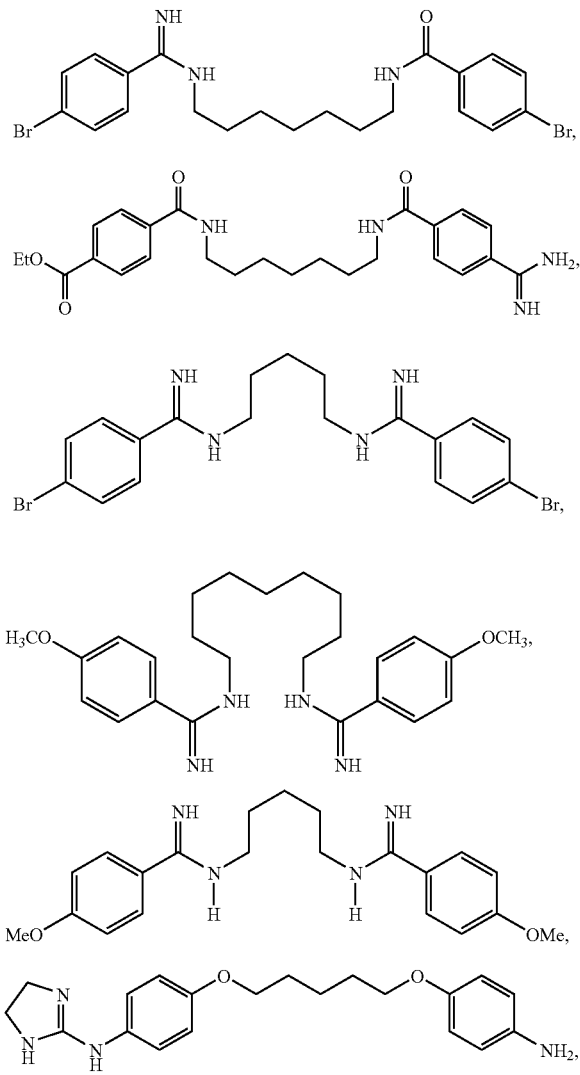

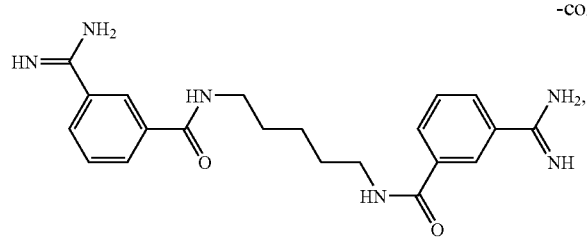

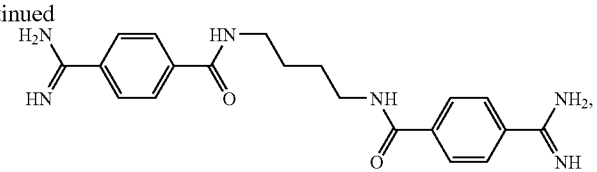

and pharmaceutically acceptable salts thereof.

5. A pharmaceutical composition comprising a compound according to claim 4, and a pharmaceutically acceptable vehicle.

6. A pharmaceutical composition for the treatment of a disease selected from the group consisting of Alzheimer's disease, Down's syndrome, Mild Cognitive Impairment, age-related macular degeneration, and cerebral amyloid angiopathy comprising a therapeutically effective amount of a compound according to claim 4.

7. A method for the treatment of Alzheimer's disease in a subject comprising administering to a subject a therapeutically effective amount of a compound, wherein said compound is selected from the group consisting of

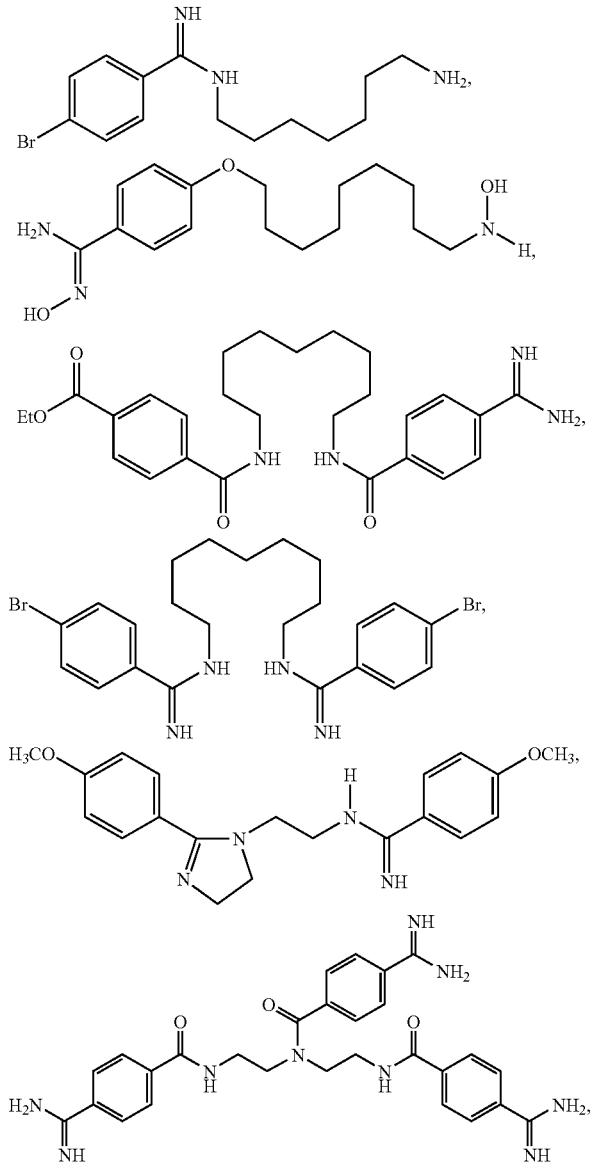

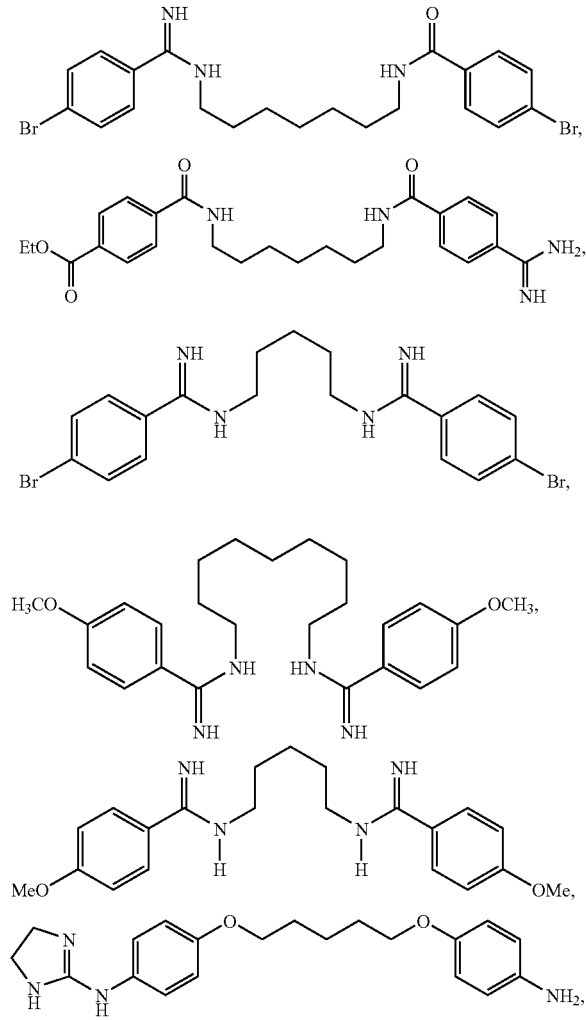

-continued
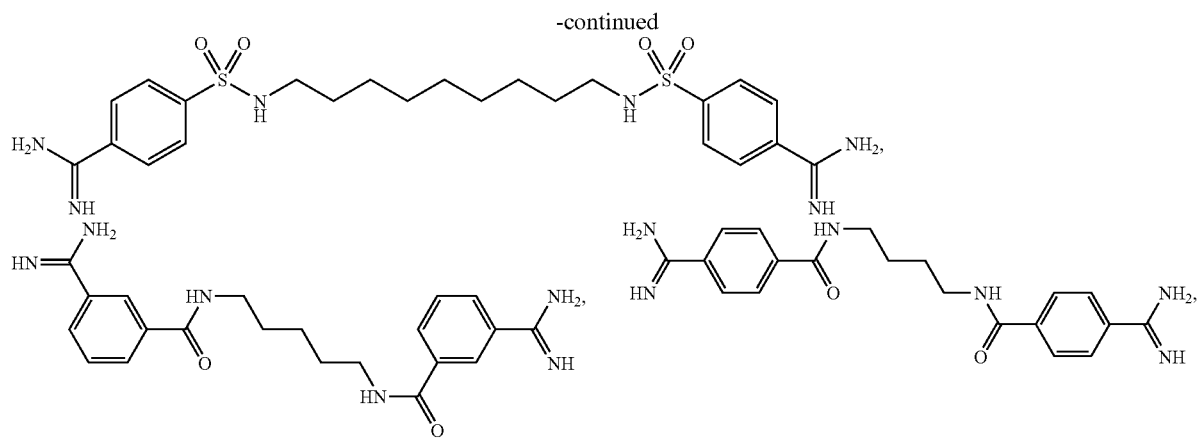
and pharmaceutically acceptable salts thereof.
* * * * *